(12) United States Patent
Panitch et al.

(10) Patent No.: US 8,846,003 B2
(45) Date of Patent: Sep. 30, 2014

(54) COLLAGEN-BINDING SYNTHETIC PEPTIDOGLYCANS, PREPARATION, AND METHODS OF USE

(75) Inventors: Alyssa Panitch, West Lafayette, IN (US); John E. Paderi, Lafayette, IN (US); Kinam Park, West Lafayette, IN (US); Katherine Stuart, Lafayette, IN (US); Steve Higbee, Lafayette, IN (US)

(73) Assignee: Symic Biomedical, Inc., San Francisco, CA (US)

( * ) Notice: Subject to any disclaimer, the term of this patent is extended or adjusted under 35 U.S.C. 154(b) by 701 days.

(21) Appl. No.: 12/934,551

(22) PCT Filed: Mar. 27, 2009

(86) PCT No.: PCT/US2009/038624
§ 371 (c)(1),
(2), (4) Date: Sep. 24, 2010

(87) PCT Pub. No.: WO2009/120995
PCT Pub. Date: Oct. 1, 2009

(65) Prior Publication Data
US 2011/0020298 A1     Jan. 27, 2011

Related U.S. Application Data

(60) Provisional application No. 61/081,984, filed on Jul. 18, 2008, provisional application No. 61/039,933, filed on Mar. 27, 2008.

(51) Int. Cl.
| | |
|---|---|
| *A61L 27/54* | (2006.01) |
| *C07K 14/78* | (2006.01) |
| *A61L 27/38* | (2006.01) |
| *A61L 27/24* | (2006.01) |
| *C07K 14/47* | (2006.01) |
| *A61K 38/00* | (2006.01) |

(52) U.S. Cl.
CPC ............ *C07K 14/78* (2013.01); *A61L 2300/42* (2013.01); *A61L 27/54* (2013.01); *A61K 38/00* (2013.01); *A61L 2300/25* (2013.01); *A61L 27/3804* (2013.01); *A61L 27/24* (2013.01); *C07K 14/4725* (2013.01)
USPC ......... 424/1.73; 424/418; 424/461; 514/17.2; 514/1.1; 514/20.9; 530/356

(58) Field of Classification Search
CPC ............................................ A61K 2039/55583
See application file for complete search history.

(56) References Cited

U.S. PATENT DOCUMENTS

| | | | | |
|---|---|---|---|---|
| 4,683,298 A | * | 7/1987 | Yalpani | 536/45 |
| 5,271,929 A | * | 12/1993 | Hashiguchi et al. | 424/9.35 |
| 8,304,388 B2 | * | 11/2012 | Chettibi et al. | 514/17.2 |
| 2002/0098153 A1 | * | 7/2002 | Allen et al. | 424/9.364 |
| 2005/0043221 A1 | * | 2/2005 | Fallon et al. | 514/8 |
| 2006/0252692 A1 | * | 11/2006 | Lasser et al. | 514/12 |

OTHER PUBLICATIONS

Bhide et al. (2005) Collagen Phagocytosis by Fibroblasts Is Regulated by Decorin, J. Biol. Chem., vol. 280, No. 24, pp. 23103-23113.*
Svensson et al. (1995) Decorin-binding sites for collagen type I are mainly located in leucine-rich repeats 4-5, J. Biol. Chem., vol. 270, No. 35, pp. 20712-20716.*
Business Wire (2003) "ZymoGenetics Reports New Findings on Anti-thrombotic Activities of CTRP1; Novel Protein Prevents Platelet Thrombosis without Causing Bleeding", www.thefreelibrary.com/ZymoGenetics+Reports+New+Findings+on+Anti-thrombotic+Activities+of-a0105542135, pp. 1-3.*
Chiang, Thomas M., et al., "Cloning, Characterization, and Functional Studies of a 47-kDa Platelet Receptor for Type III Collagen", Jul. 10, 2002, The Journal of Biological Chemistry, vol. 277, No. 38, pp. 34896-34901.
Chiang, Thomas M., et al., "Peptides Derived From Platelet Non-Integrin Collagen-Receptors or Types I and III Collagen Inhibit Collagen-Platelet Interaction", 2007, Cardiovascular & Haematological Disorders-Drug Targets, vol. 7, No. 1, pp. 71-75.
Fulzele, S.V., et al., "Study of the Biodegradation and In Vivo Biocompatibility of Novel Biomaterials", 2003 European Journal of Pharmaceutical Sciences, vol. 20, pp. 53-61.
Griffey, Sy, et al., "Particulate Dermal Matrix as an Injectable Soft Tissue Replacement Material", 2001 J. Biomed. Mater. Res., vol. 58, pp. 10-15.
Hermanson G.T., "Zero-Length Cross-Linkers", 1996, Academic Press, pp. 169-186.
Huizinga, Eric G., et al., "Crystal Structure of the A3 Domain of Human Von Willebrand Factor: Implications for Collagen Binding", Sep. 15, 1997, Structure, vol. 5, pp. 1147-1156.
Hunt, Thomas K., et al., Respiratory Gas Tensions and pH in Healing Wounds, Feb. 19-22, 1967, American Journal of Surgery, vol. 114, pp. 302-307.
Pizzo, A. M., et al., "Extracellular Matrix (ECM) Microstructural Composition Regulates Local Cell-ECM Biomechanics and Fundamental Fibroblast Behavior: A Multidimensional Perspective", Dec. 23, 2004, Journal Appl. Physiol, vol. 98, pp. 1909-1921.

(Continued)

*Primary Examiner* — Manjunath Rao
*Assistant Examiner* — Samuel Liu
(74) *Attorney, Agent, or Firm* — Sheppard Mullin Richter & Hampton LLP

(57) ABSTRACT

This invention relates to collagen-binding synthetic peptidoglycans and engineered collagen matrices comprising a collagen matrix and a collagen-binding synthetic peptidoglycan where the collagen-binding synthetic peptidoglycan can be aberrant or can have amino acid homology with a portion of the amino acid sequence of a protein or a proteoglycan that regulates collagen fibrillogenesis. The invention also relates to kits, compounds, compositions, and engineered graft constructs comprising such collagen-binding synthetic peptidoglycans or engineered collagen matrices and methods for their preparation and use.

16 Claims, 55 Drawing Sheets

(56) References Cited

OTHER PUBLICATIONS

Roeder, Blayne A., et al., "Tensile Mechanical Properties of Three-Dimensional Type I Collagen Extracellular Matrices With Varied Microstructure", Apr. 2002, Transactions of the ASME, vol. 124, pp. 214-222.

Romijn, Roland A., et al., "Mapping the Collagen-Binding Site in the Von Willebrand Factor-A3 Domain", Apr. 25, 2003,The Journal of Biological Chemistry, vol. 278, No. 17, pp. 15035-15039.

Schilling, John A., et al., "Wound Healing: A Comparative Study of the Histochemical Changes in Granulation Tissue Contained in Stainless Steel Wire Mesh and Polyvinyl Sponge Cylinders", 1959, Surgery, vol. 46, No. 4, pp. 702-710.

International Search Report/Written Opinion for PCT/US2009/038624 mailed Dec. 7, 2009.

Bierbaum, Susanne, et al , "Collageneous Matrix Coatings on Titanium Implants Modified with Decorin and Chondroitin Sulfate: Characterization and Influence on Osteoblastic Cells", 2006, Journal of Biomedical Materials Research, pp. 551-562.

Kalamajski, Sebastian, et al. "The Decorin Sequence SYIRIADTNIT Binds Collagen Type I", Jun. 1, 2007, Journal of Biological Chemistry, vol. 282, No. 22, pp. 16062-16067.

Pieper J. S., et al., "Development of Tailor Made Collagen-Glycosaminoglycan Matrices: EDC/NHS Crosslinking, and Ultrastructural Aspects", 2000, Biomaterials, No. 21, pp. 581-593.

Schonherr, et al., "Decorin Core Protein Fragment LEU 155-Val260 Interacts with TGF-Beta But Does Not Compete for Decorin Binding to Type I Collagen", Jul. 15, 1998, Arch. Biochem. Biophys., vol. 355, No. 2, pp. 241-248, Abstract Only.

Tenni, Ruggero, et al., "Interaction of Decorin with CNBr Peptides from Collagens I and II Evidence for Multiple Binding Sites and Essential Lysyl Residues in Collagen", 2002, Eur. J. Biochem., vol. 269, pp. 1428-1437.

UniProtKB, "Decorin Precursor—*Bos Taurus* (Bovine)", Last Modified Sep. 1, 2009, Available on the Internet <URL: http://www.uniprot.org/uniprot/P21793.

UniProt/TrEMBL Q7Z4J1, "Nonintegrin Platelet Receptor for Type I Collagen", Last Modified Feb. 10, 2009, Available on the Internet <URL: http://www.uniprot.org/uniprotQ7Z4J1&format=html.

Grassl, E. D., et al., Fibrin as an Alternative Biopolymer to Type-I Collagen for the Fabrication of a Media Equivalent, 2002, Journal of Biomedical Materials Research, vol. 60, No. 4, pp. 607-612.

\* cited by examiner

SEQUENCE LISTING

```
<160> NUMBER OF SEQ ID NOS: 17

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Ala Asn Ala Ala Leu Lys Ala Gly Glu Leu Tyr Lys Ser Ile
1               5                   10                  15

Leu Tyr Gly Cys
            20
```

```
<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Leu Asp Gly Asn Glu Ile Lys Arg Gly Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala His Glu Glu Ile Ser Thr Thr Asn Glu Gly Val Met Gly Cys
1               5                   10                  15

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln Gly Cys
            20                  25                  30

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Gln Asp Ser Glu Thr Arg Thr Phe Tyr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Lys Lys Thr Leu Arg Thr Gly Cys
1               5

<210> SEQ ID NO 7
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Gly Leu Arg Ser Lys Ser Lys Phe Arg Arg Pro Asp Ile Gln Tyr
1               5                   10                  15

Pro Asp Ala Thr Asp Glu Asp Ile Thr Ser His Met Gly Cys
            20                  25                  30

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Asn Pro Val Gln Pro Gly Cys
1               5

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Tyr Ile Arg Ile Ala Asp Thr Asn Ile Thr Gly Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Ile Arg Ile Ala Asp Thr Asn Ile Thr
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Glu Leu Asn Leu Val Tyr Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Lys Glu Leu Asn Leu Val Tyr Thr Gly Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Ile Thr Thr Ile Asp Val Pro Trp Asn Val
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Ile Thr Thr Ile Asp Val Pro Trp Asn Val Gly Cys
1               5                   10

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Arg Arg Ala Asn Ala Ala Leu Lys Ala Gly Glu Leu Tyr Lys Ser
1               5                   10                  15

Ile Leu Tyr Gly Cys
            20

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ser Tyr Ile Arg Ile Ala Asp Thr Asn Ile Thr
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Tyr Ile Arg Ile Ala Asp Thr Asn Ile Thr Gly Cys
1               5                   10
```

US 8,846,003 B2

COLLAGEN-BINDING SYNTHETIC PEPTIDOGLYCANS, PREPARATION, AND METHODS OF USE

CROSS-REFERENCE TO RELATED APPLICATIONS

This application is a U.S. national application filed under 37 C.F.R. §371(b) of International Application Serial No. PCT/US2009/038624 filed Mar. 27, 2009, which claims priority to U.S. Provisional Patent Application Ser. No. 61/039,933 filed on Mar. 27, 2008, and U.S. Provisional Patent Application Ser. No. 61/081,984 filed on Jul. 18, 2008, the entire disclosures of which are hereby incorporated by reference.

GOVERNMENT RIGHTS

Part of the work during the development of this invention was made with government support from the National Institutes of Health under grant application number K25HL074968. The U.S. Government has certain rights in the invention.

TECHNICAL FIELD

This invention pertains to the field of collagen-binding synthetic peptidoglycans and methods of forming and using the same.

BACKGROUND AND SUMMARY OF THE INVENTION

Collagen is the most abundant protein in the body, presenting many biological signals and maintaining the mechanical integrity of many different tissues. Its molecular organization determines its function, which has made collagen fibrillogenesis a topic of interest in many research fields. Collagen has the ability to self-associate in vitro, forming gels that can act as a 3-dimensional substrate, and provide mechanical and biological signals for cell growth. Research on collagen fibrillogenesis with and without additional extracellular matrix components has raised many questions about the interplay between collagen and other extracellular matrix molecules. There are more than 20 types of collagen currently identified, with type I being the most common Many tissues are composed primarily of type I collagen including tendon, ligament, skin, and bone. While each of these structures also contains other collagen types, proteoglycans and glycosaminoglycans, and minerals in the case of bone, the principle component is type I collagen. The dramatic difference in mechanical integrity each of these structures exhibits is largely due to the intricate organization of collagen and the interplay with other non-collagen type I components.

Decorin is a proteoglycan that is known to influence collagen fibrillogenesis, which consequently can modify the mechanical and biological information in a collagen gel. The signals resulting from structural changes in collagen organization, as well as the unique signals contained in the glycosaminoglycan chains that are part of proteoglycans, alter cellular behavior and offer a mechanism to design collagen matrices to provide desired cellular responses. Consequently, we have developed collagen-binding synthetic peptidoglycans which influence collagen organization at the molecular level. These collagen-binding synthetic peptidoglycans are designed based on collagen binding peptides attached to, for example, a glycan, such as a glycosaminoglycan or a polysaccharide, and can be tailored with respect to these components for specific applications. The collagen-binding synthetic peptidoglycans described herein influence the morphological, mechanical, and biological characteristics of collagen matrices, and consequently alter cellular behavior, making these molecules useful for tissue engineering applications.

In one embodiment, an engineered collagen matrix comprising a collagen matrix and a collagen-binding synthetic peptidoglycan is provided. In this embodiment, the 1) collagen can be crosslinked or uncrosslinked, 2) the collagen-binding synthetic peptidoglycan can have amino acid homology with a portion of the amino acid sequence of a protein or a proteoglycan that regulates collagen fibrillogenesis or the collagen-binding synthetic peptidoglycan can be an aberrant collagen-binding synthetic peptidoglycan, 3) the engineered collagen matrix can further comprise an exogenous population of cells, 4) the exogenous population of cells can be selected from non-keratinized or keratinized epithelial cells or a population of cells selected from the group consisting of endothelial cells, mesodermally derived cells, mesothelial cells, synoviocytes, neural cells, glial cells, osteoblast cells, fibroblasts, chondrocytes, tenocytes, smooth muscle cells, skeletal muscle cells, cardiac muscle cells, multi-potential progenitor cells (e.g., stem cells, including bone marrow progenitor cells), and osteogenic cells, 5) the engineered collagen matrix can further comprise at least one polysaccharide, 6) the collagen-binding synthetic peptidoglycan can be a compound of formula $P_nG_x$ wherein n is 1 to 10, wherein x is 1 to 10, wherein P is a synthetic peptide of about 5 to about 40 amino acids comprising a sequence of a collagen-binding domain, and wherein G is a glycan (e.g. a glycosaminoglycan or a polysaccharide), 7) the collagen-binding synthetic peptidoglycan can be a compound of formula $(P_nL)_xG$ wherein n is 1 to 5, wherein x is 1 to 10, wherein P is a synthetic peptide of about 5 to about 40 amino acids comprising a sequence of a collagen-binding domain, wherein L is a linker, and wherein G is a glycan, 8) the collagen-binding synthetic peptidoglycan can be a compound of formula $P(LG_n)_x$ wherein n is 1 to 5, wherein x is 1 to 10, wherein P is a synthetic peptide of about 5 to about 40 amino acids comprising a sequence of a collagen-binding domain, wherein L is a linker, and wherein G is a glycan, 9) the synthetic peptide can have amino acid homology with the amino acid sequence of a small leucine-rich proteoglycan or a platelet receptor sequence, 10) the synthetic peptide can have amino acid homology with the amino acid sequence of a platelet collagen receptor sequence, 11) the peptide can comprise an amino acid sequence selected from the group consisting of RRANAALKAGELYKSILYGC [SEQ ID NO: 1], RLDGNEIKRGC [SEQ ID NO: 2], AHEEISTTNEGVMGC [SEQ ID NO: 3], NGVFKYRPRYFLYKHAYFYPPLKRFPVQGC [SEQ ID NO: 4], CQDSETRTFY [SEQ ID NO: 5], TKKTLRTGC [SEQ ID NO: 6], GLRSKSKKFRRPDIQYPDATDEDITSHMGC [SEQ ID NO: 7], SQNPVQPGC [SEQ ID NO: 8], SYIRIADTNITGC [SEQ ID NO: 9], SYIRIADTNIT [SEQ ID NO: 10], KELNLVYT [SEQ ID NO: 11], KELNLVYTGC [SEQ ID NO: 12], GSITTIDVPWNV [SEQ ID NO: 13], and GSITTIDVPWNVGC [SEQ ID NO: 14], 12) the glycan can be selected from the group consisting of alginate, agarose, dextran, chondroitin, dermatan, dermatan sulfate, heparan, heparin, keratin, and hyaluronan, 13) the glycan can be selected from the group consisting of dermatan sulfate, dextran, and heparin, 14) the collagen can be selected from the group consisting of type I collagen, type II collagen, type III collagen, type IV collagen, and combinations thereof, 15) the glycan can be a glycosaminoglycan or a polysaccharide, or 16) the invention can include any combination of the features described in this paragraph.

In another illustrative embodiment, a method of preparing an engineered collagen matrix is provided. The method comprises the steps of providing a collagen solution, providing a collagen-binding synthetic peptidoglycan, and polymerizing the collagen in the presence of the collagen-binding synthetic peptidoglycan to form the engineered collagen matrix. This embodiment can include any of the features described in the preceding paragraph. Also, in this embodiment, the amount of collagen in the collagen solution can be from about 0.4 mg/mL to about 6 mg/mL, and the molar ratio of the collagen to the collagen-binding synthetic peptidoglycan can be from about 1:1 to about 40:1.

In yet another embodiment a compound of formula $P_nG_x$ is provided wherein n is 1 to 10, wherein x is 1 to 10, wherein P is a synthetic peptide of about 5 to about 40 amino acids comprising a sequence of a collagen-binding domain, and wherein G is a glycan.

In a further embodiment, a compound is provided of formula $(P_nL)_xG$ wherein n is 1 to 5, wherein x is 1 to 10, wherein P is a synthetic peptide of about 5 to about 40 amino acids comprising a sequence of a collagen-binding domain, wherein L is a linker, and G is a glycan.

In still another illustrative embodiment, a compound is provided of formula $P(LG_n)_x$ wherein n is 1 to 5, wherein x is 1 to 10, wherein P is a synthetic peptide of about 5 to about 40 amino acids comprising a sequence of a collagen-binding domain, wherein L is a linker, and wherein G is a glycan. In any of these compound embodiments the linker can comprise the formula —SCH$_2$CH$_2$C(O)NHN=, the glycan can be a glycosaminoglycan or a polysaccharide, and any applicable features described above can also be included.

In another aspect, a method of altering the structure or mechanical characteristics of an engineered collagen matrix is provided. The method comprises the steps of providing a collagen solution, providing a collagen-binding synthetic peptidoglycan, and polymerizing the collagen in the presence of the collagen-binding synthetic peptidoglycan to form the altered, engineered collagen matrix. Any applicable features described above can also be included.

In another embodiment, a kit is provided. The kit can comprise any of the engineered collagen matrices described above. In this embodiment, the engineered collagen matrix can be sterilized, and the kit can further comprise cells wherein the cells can be selected from the group consisting of mesothelial cells, synoviocytes, progenitor cells, fibroblasts, neural cells, glial cells, osteoblast cells, chondrocytes, tenocytes, endothelial cells, and smooth muscle cells. The engineered collagen matrix can comprise any of the compounds described above.

In one embodiment, a method for inhibiting activation of platelets is described, the method comprising the step of providing a collagen-binding synthetic peptidoglycan for contacting collagen wherein the collagen-binding synthetic peptidoglycan binds to the collagen and wherein activation of the platelets is inhibited. In another embodiment, a method for inhibiting adhesion of platelets to collagen is described, the method comprising the step of providing a collagen-binding synthetic peptidoglycan for contacting collagen wherein the collagen-binding synthetic peptidoglycan binds to the collagen, and wherein adhesion of the platelets to collagen is inhibited. In another embodiment, either of the above methods wherein the glycan is selected from the group consisting of hyaluronan, heparin, and dextran is provided. In still another embodiment, the collagen-binding synthetic peptidoglycan used in any of the above methods comprises a peptide selected from the group consisting of RRANAALK-AGELYKSILYGC [SEQ ID NO: 1], GSITTIDVPWNV [SEQ ID NO: 13], and GSITTIDVPWNVGC [SEQ ID NO: 14].

In yet another embodiment, a graft construct is provided. The graft construct comprises any of the engineered collagen matrices described above.

DETAILED DESCRIPTION OF THE ILLUSTRATIVE EMBODIMENTS

Figure 1:
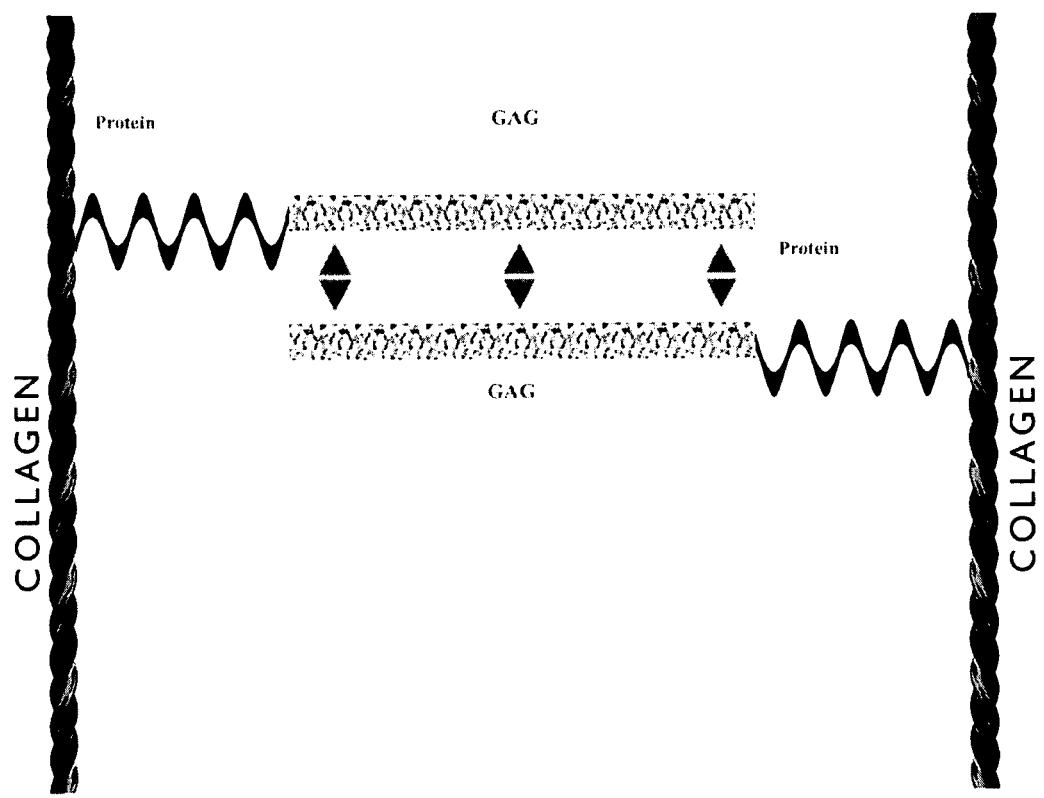
FIG. 1 shows a schematic representation of the interaction between neighboring proteoglycans on adjacent tropocollagen strands which is important in determining the mechanical and alignment properties of collagen matrices.

As used in accordance with this invention, a "collagen-binding synthetic peptidoglycan" means a collagen-binding conjugate of a glycan with a synthetic peptide. The "collagen-binding synthetic peptidoglycans" can have amino acid homology with a portion of a protein or a proteoglycan not normally involved in collagen fibrillogenesis. These collagen-binding synthetic peptidoglycans are referred to herein as "aberrant collagen-binding synthetic peptidoglycans". The aberrant collagen-binding synthetic peptidoglycans may or may not affect collagen fibrillogenesis. Other collagen-binding synthetic peptidoglycans can have amino acid homology to a portion of a protein or to a proteoglycan normally involved in collagen fibrillogenesis. These collagen-binding synthetic peptidoglycans are referred to herein as "fibrillogenic collagen-binding synthetic peptidoglycans".

As used herein an "engineered collagen matrix" means a collagen matrix where the collagen is polymerized in vitro in combination with a collagen-binding synthetic peptidoglycan under predetermined conditions that can be varied and are selected from the group consisting of, but not limited to, pH, phosphate concentration, temperature, buffer composition, ionic strength, and composition and concentration of the collagen.

As used herein an "engineered graft construct" means a graft construct comprising an "engineered collagen matrix."

In one aspect of the invention, an engineered collagen matrix is provided. The engineered collagen matrix comprises collagen and a collagen-binding synthetic peptidoglycan. In one embodiment, the engineered collagen matrix may be uncrosslinked. In another embodiment, the matrix may be crosslinked. In various illustrative embodiments, crosslinking agents, such as carbodiimides, aldehydes, lysl-oxidase, N-hydroxysuccinimide esters, imidoesters, hydrazides, and maleimides, as well as various natural crosslinking agents, including genipin, and the like, can be added before, during, or after polymerization of the collagen in solution.

In various illustrative embodiments, the collagen used herein to prepare an engineered collagen matrix may be any type of collagen, including collagen types I to XXVIII, alone or in any combination, for example, collagen types I, II, III, and/or IV may be used. In one embodiment, the engineered collagen matrix is formed using commercially available collagen (e.g., Sigma, St. Louis, Mo.). In an alternative embodiment, the collagen can be purified from submucosa-containing tissue material such as intestinal, urinary bladder, or stomach tissue. In a further embodiment, the collagen can be purified from tail tendon. In an additional embodiment, the collagen can be purified from skin. In various aspects, the collagen can also contain endogenous or exogenously added non-collagenous proteins in addition to the collagen-binding synthetic peptidoglycans, such as fibronectin or silk proteins, glycoproteins, and polysaccharides, or the like. The engineered graft constructs or engineered collagen matrices prepared by the methods described herein can serve as constructs for the regrowth of endogenous tissues at the implantation site (e.g., biological remodeling) which can assume the characterizing features of the tissue(s) with which they are associated at the site of implantation or injection.

In various illustrative aspects, the collagen-binding synthetic peptidoglycans used to form the engineered graft constructs or engineered collagen matrices in accordance with the invention comprise synthetic peptides of about 5 to about 40 amino acids. In some embodiments, these peptides have homology to the amino acid sequence of a small leucine-rich proteoglycan or a platelet receptor sequence. In various embodiments the synthetic peptide comprises an amino acid sequence selected from the group consisting of RRANAALKAGELYKSILYGC [SEQ ID NO: 1], RLDGNEIKRGC [SEQ ID NO: 2], AHEEISTTNEGVMGC [SEQ ID NO: 3], NGVFKYRPRYFLYKHAYFYPPLKRFPVQGC [SEQ ID NO: 4], CQDSETRTFY [SEQ ID NO: 5], TKKTLRTGC [SEQ ID NO: 6], GLRSKSKKFRRPDIQYPDATDEDITSHMGC [SEQ ID NO: 7], SQNPVQPGC [SEQ ID NO: 8], SYIRIADTNITGC [SEQ ID NO: 9], SYIRIADTNIT [SEQ ID NO: 10], KELNLVYT [SEQ ID NO: 11], KELNLVYTGC [SEQ ID NO: 12], GSITTIDVPWNV [SEQ ID NO: 13], and GSITTIDVPWNVGC [SEQ ID NO: 14]. In another embodiment, the synthetic peptide can comprise or can be an amino acid sequence selected from the group consisting of RRANAALKAGELYKSILYGC [SEQ ID NO: 1], RLDGNEIKRGC [SEQ ID NO: 2], AHEEISTTNEGVMGC [SEQ ID NO: 3], NGVFKYRPRYFLYKHAYFYPPLKRFPVQGC [SEQ ID NO: 4], CQDSETRTFY [SEQ ID NO: 5], TKKTLRTGC [SEQ ID NO: 6], GLRSKSKKFRRPDIQYPDATDEDITSHMGC [SEQ ID NO: 7], SQNPVQPGC [SEQ ID NO: 8], SYIRIADTNITGC [SEQ ID NO: 9], SYIRIADTNIT [SEQ ID NO: 10], KELNLVYT [SEQ ID NO: 11], KELNLVYTGC [SEQ ID NO: 12], GSITTIDVPWNV [SEQ ID NO: 13], GSITTIDVPWNVGC [SEQ ID NO: 14], and an amino acid sequence with 80%, 85%, 90%, 95%, or 98% homology with to any of these fourteen amino acid sequences. The synthetic peptide can also be any peptide of 5 to 40 amino acids selected from peptides that have collagen-binding activity and that are 80%, 85%, 90%, 95%, 98%, or 100% homologous with the collagen-binding domain(s) of the von Willebrand factor or a platelet collagen receptor as described in Chiang, et al. $J.$ $Biol.$ $Chem.$ 277: 34896-34901 (2002), Huizing a, et al., $Structure$ 5: 1147-1156 (1997), Romijn, et al., $J.$ $Biol.$ $Chem.$ 278: 15035-15039 (2003), and Chiang, et al., $Cardio.$ $\&$ $Haemato.$ $Disorders-Drug$ $Targets$ 7: 71-75 (2007), each incorporated herein by reference.

The glycan (e.g. glycosaminoglycan, abbreviated GAG, or polysaccharide) attached to the synthetic peptide can be selected from the group consisting alginate, agarose, dextran, chondroitin, dermatan, dermatan sulfate, heparan, heparin, keratin, and hyaluronan. In one embodiment, the glycan is selected from the group consisting of dermatan sulfate, dextran, and heparin.

In one illustrative aspect, the engineered collagen matrix or the engineered graft construct may be sterilized. As used herein "sterilization" or "sterilize" or "sterilized" means disinfecting the matrix or graft construct by removing unwanted contaminants including, but not limited to, endotoxins, nucleic acid contaminants, and infectious agents.

In various illustrative embodiments, the engineered collagen matrix or engineered graft construct can be disinfected and/or sterilized using conventional sterilization techniques including glutaraldehyde tanning, formaldehyde tanning at acidic pH, propylene oxide or ethylene oxide treatment, gas plasma sterilization, gamma radiation, electron beam, and/or sterilization with a peracid, such as peracetic acid. Sterilization techniques which do not adversely affect the structure and biotropic properties of the matrix or construct can be used. Illustrative sterilization techniques are exposing the engineered graft construct or engineered collagen matrix, to peracetic acid, 1-4 Mrads gamma irradiation (or 1-2.5 Mrads of gamma irradiation), ethylene oxide treatment, or gas plasma sterilization. In one embodiment, the engineered graft construct can be subjected to one or more sterilization processes. In illustrative embodiments, the collagen in solution can also be sterilized or disinfected. The engineered collagen matrix or engineered graft construct may be wrapped in any type of container including a plastic wrap or a foil wrap, and may be further sterilized.

In any of these embodiments the engineered graft construct or engineered collagen matrix may further comprise an added population of cells. The added population of cells may comprise one or more cell populations. In various embodiments, the cell populations comprise a population of non-keratinized or keratinized epithelial cells or a population of cells selected from the group consisting of endothelial cells, mesodermally derived cells, mesothelial cells, synoviocytes, neural cells, glial cells, osteoblasts, fibroblasts, chondrocytes, tenocytes, smooth muscle cells, skeletal muscle cells, cardiac muscle cells, multi-potential progenitor cells (e.g., stem cells, including bone marrow progenitor cells), and osteogenic cells. In various embodiments, the engineered graft construct or engineered collagen matrix can be seeded with one or more cell types in combination.

In various aspects, the engineered collagen matrices or engineered graft constructs of the present invention can be combined with nutrients, including minerals, amino acids, sugars, peptides, proteins, vitamins (such as ascorbic acid), or laminin, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic. In other illustrative embodiments, cross-linking agents, such as carbodiimides, aldehydes, lysl-oxidase, N-hydroxysuccinimide esters, imidoesters, hydrazides, and maleimides, as well as natural crosslinking agents, including genipin, and the like can be added before, concurrent with, or after the addition of cells.

As discussed above, in accordance with one embodiment, cells can be added to the engineered collagen matrices or engineered graft constructs after polymerization of the collagen or during collagen polymerization. The engineered collagen matrices comprising the cells can be subsequently injected or implanted in a host for use as engineered graft constructs. In another embodiment, the cells on or within the engineered collagen matrices can be cultured in vitro, for a predetermined length of time, to increase the cell number or to induce desired remodeling prior to implantation or injection into a host.

In accordance with one embodiment, a kit is provided comprising the engineered collagen matrix or engineered graft construct. The kit itself can be within a container of any type, and the kit can contain instructions for use of the components of the kit. In one embodiment, cells may constitute a component of the kit. In various embodiments, the characteristics of the engineered collagen matrices may vary. In various illustrative embodiments, the engineered collagen matrix or engineered graft construct in the kit may comprise various other components, including non-collagenous proteins and polysaccharides, in addition to the collagen-binding synthetic peptidoglycan(s). In one embodiment, the kit comprises a vessel, vial, container, bag, or wrap, for example, containing an engineered collagen matrix or an engineered graft construct. In another embodiment, the kit comprises separate vessels (e.g., a vial, container, bag, or wrap), each containing one of the following components: a collagen solution or lyophilized collagen and one or more types of collagen-binding synthetic peptidoglycans. In another embodiment, the kit comprises separate vessels, each containing one of the following components: a collagen solution or lyophilized collagen, a buffer, and one or more types of collagen-binding synthetic peptidoglycans. In any of these embodiments, the kits can further comprise a buffer, a sterilizing or disinfecting agent, non-collagenous proteins or polysaccharides, and/or instructional materials describing methods for using the kit reagents or describing methods for using the engineered collagen matrices or the engineered graft construct. The kit can also contain one or more types of collagen-binding synthetic peptidoglycans for use as pharmacological agents in the absence of an engineered collagen matrix or an engineered graft construct. In this embodiment, the kit can be within a container of any type, and the kit can contain instructions for use of the collagen-binding synthetic peptidoglycans.

In yet another embodiment, the kit further comprises a container (e.g. a flask, an ampule, a vial, a tube, or a bottle, for example) of cells, including but not limited to, a population of non-keratinized or keratinized epithelial cells or a population of cells selected from the group consisting of endothelial cells, mesodermally derived cells, mesothelial cells, synoviocytes, neural cells, glial cells, osteoblasts, fibroblasts, chondrocytes, tenocytes, smooth muscle cells, skeletal muscle cells, cardiac muscle cells, multi-potential progenitor cells (e.g., stem cells, including bone marrow progenitor cells), and osteogenic cells. In another embodiment the cells may be present on a plate. In one embodiment, one or more containers of cells may be included and the kit may comprise one or more cell type and cell culture reagents.

In one illustrative aspect, a method of preparing an engineered collagen matrix is provided. The method comprises the steps of providing a collagen solution, providing a collagen-binding synthetic peptidoglycan, and polymerizing the collagen in the presence of the collagen-binding synthetic peptidoglycan to form the engineered collagen matrix. In various embodiments, the collagen-binding synthetic peptidoglycan can be an aberrant collagen-binding synthetic peptidoglycan or a fibrillogenic collagen-binding synthetic peptidoglycan with amino acid homology to a portion of the amino acid sequence of a proteoglycan that normally regulates collagen fibrillogenesis.

In embodiments where the collagen-binding synthetic peptidoglycan is an aberrant collagen-binding synthetic peptidoglycan or a fibrillogenic collagen-binding synthetic peptidoglycan, a method of altering the structure or mechanical characteristics of a collagen matrix is provided. As used herein, "altering" means changing the mechanical or structural characteristics of a collagen matrix polymerized in vitro in the presence of the collagen-binding synthetic peptidoglycan relative to that of a collagen matrix polymerized in the absence of the collagen-binding synthetic peptidoglycan. The method comprises the steps of providing a collagen solution, providing a collagen-binding synthetic peptidoglycan, and polymerizing the collagen in the presence of the collagen-binding synthetic peptidoglycan (e.g., aberrant or fibrillogenic collagen-binding synthetic peptidoglycan) to form the altered collagen matrix.

In one illustrative embodiment, the collagen solution provided can have a collagen concentration ranging from about 0.4 mg/ml to about 6 mg/ml. In various embodiments, the collagen concentration may range from about 0.5 mg/ml to about 10 mg/ml, about 0.1 mg/ml to about 6 mg/ml, about 0.5 mg/ml to about 3 mg/ml, about 1 mg/ml to about 3 mg/ml, and about 2 mg/ml to about 4 mg/ml.

As discussed above, in various illustrative aspects, the collagen-binding synthetic peptidoglycans used to form the engineered graft constructs or engineered collagen matrices in accordance with the invention comprise peptides of about 5 to about 40 amino acids with homology to the amino acid sequence of a small leucine-rich proteoglycan or a platelet receptor sequence. In various embodiments the synthetic peptide comprises an amino acid sequence selected from the group consisting of RRANAALKAGELYKSILYGC [SEQ ID NO: 1], RLDGNEIKRGC [SEQ ID NO: 2], AHEEISTT-NEGVMGC [SEQ ID NO: 3], CQDSETRTFY [SEQ ID NO: 5], TKKTLRTGC [SEQ ID NO: 6], GLRSKSKKFRRP-DIQYPDATDEDITSHMGC [SEQ ID NO: 7], SQN-PVQPGC [SEQ ID NO: 8], SYIRIADTNITGC [SEQ ID NO: 9], SYIRIADTNIT [SEQ ID NO: 10], KELNLVYT [SEQ ID NO: 11], KELNLVYTGC [SEQ ID NO: 12], GSITTIDVP-WNV [SEQ ID NO: 13], NGVFKYRPRYFLYKHAYFYP-PLKRFPVQGC [SEQ ID NO: 4], and GSITTIDVPWNVGC [SEQ ID NO: 14]. In another embodiment, the synthetic peptide can comprise or can be an amino acid sequence selected from the group consisting of RRANAALKAGE-LYKSILYGC [SEQ ID NO: 1], RLDGNEIKRGC [SEQ ID NO: 2], AHEEISTTNEGVMGC [SEQ ID NO: 3], NGVFKYRPRYFLYKHAYFYPPLKRFPVQGC [SEQ ID NO: 4], CQDSETRTFY [SEQ ID NO: 5], TKKTLRTGC [SEQ ID NO: 6], GLRSKSKKFRRPDIQYPDATDEDITSH-MGC [SEQ ID NO: 7], SQNPVQPGC [SEQ ID NO: 8], SYIRIADTNITGC [SEQ ID NO: 9], SYIRIADTNIT [SEQ ID NO: 10], KELNLVYT [SEQ ID NO: 11], KELNLVYTGC [SEQ ID NO: 12], GSITTIDVPWNV [SEQ ID NO: 13], GSITTIDVPWNVGC [SEQ ID NO: 14], and an amino acid sequence with 80%, 85%, 90%, 95%, or 98% homology to any of these fourteen amino acid sequences. The synthetic peptide can also be any peptide of 5 to 40 amino acids selected from peptides that have collagen-binding activity and that are 80%, 85%, 90%, 95%, 98%, or 100% homologous to the collagen-binding domain(s) of the von Willebrand factor or a platelet collagen receptor as described in Chiang, et al. *J. Biol. Chem.* 277: 34896-34901 (2002), Huizing a, et al., *Structure* 5: 1147-1156 (1997), Romijn, et al., *J. Biol. Chem.* 278: 15035-15039 (2003), and Chiang, et al., *Cardio. & Haemato. Disorders-Drug Targets* 7: 71-75 (2007), each incorporated herein by reference.

The glycan attached to the synthetic peptide can be selected from the group consisting of alginate, agarose, dextran, chondroitin, dermatan, dermatan sulfate, heparan, heparin, keratin, and hyaluronan. In one embodiment, the glycan is selected from the group consisting of dermatan sulfate, dextran, and heparin. The collagen-binding synthetic peptidoglycan can be lyophilized prior to polymerization, for example, in a buffer or in water or in an acid, such as hydrochloric acid or acetic acid. In one illustrative aspect, the molar ratio of the collagen to the collagen-binding synthetic peptidoglycan can be from about 1:1 to about 40:1.

The polymerizing step can be performed under conditions that are varied where the conditions are selected from the group consisting of pH, phosphate concentration, temperature, buffer composition, ionic strength, the specific components present, and the concentration of the collagen or other components present. In one illustrative aspect, the collagen or other components, including the collagen-binding synthetic peptidoglycan, can be lyophilized prior to polymerization. The collagen or other components can be lyophilized in an acid, such as hydrochloric acid or acetic acid.

In various illustrative embodiments, the polymerization reaction is conducted in a buffered solution using any biologically compatible buffer known to those skilled in the art. For example, the buffer may be selected from the group consisting of phosphate buffer saline (PBS), Tris (hydroxymethyl) aminomethane Hydrochloride (Tris-HCl), 3-(N-Morpholino) Propanesulfonic Acid (MOPS), piperazine-n,n'-bis (2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES), and 1,3-bi[tris (Hydroxymethyl)methylamino]propane (Bis Tris Propane). In one embodiment the buffer is PBS, Tris, or MOPS and in one embodiment the buffer system is PBS.

In various illustrative embodiments, the polymerization step is conducted at a pH selected from the range of about 5.0 to about 11, and in one embodiment polymerization is conducted at a pH selected from the range of about 6.0 to about 9.0, and in one embodiment polymerization is conducted at a pH selected from the range of about 6.5 to about 8.5, and in another embodiment the polymerization step is conducted at a pH selected from the range of about 7.0 to about 8.5, and in another embodiment the polymerization step is conducted at a pH selected from the range of about 7.3 to about 7.4.

In other illustrative aspects, the ionic strength of the buffered solution is also regulated. In accordance with one embodiment, the ionic strength of the buffer is selected from a range of about 0.05 to about 1.5 M, in another embodiment the ionic strength is selected from a range of about 0.10 to about 0.90 M, in another embodiment the ionic strength is selected from a range of about 0.14 to about 0.30 M and in another embodiment the ionic strength is selected from a range of about 0.14 to about 0.17 M.

In still other illustrative embodiments, the polymerization step is conducted at temperatures selected from the range of about 0° C. to about 60° C. In other embodiments, the polymerization step is conducted at temperatures above 20° C., and typically the polymerization is conducted at a temperature selected from the range of about 20° C. to about 40° C., and more typically the temperature is selected from the range of about 30° C. to about 40° C. In one illustrative embodiment the polymerization is conducted at about 37° C.

In yet other embodiments, the phosphate concentration of the buffer is varied. For example, in one embodiment, the phosphate concentration is selected from a range of about 0.005 M to about 0.5 M. In another illustrative embodiment, the phosphate concentration is selected from a range of about 0.01 M to about 0.2 M. In another embodiment, the phosphate concentration is selected from a range of about 0.01 M to about 0.1 M. In another illustrative embodiment, the phosphate concentration is selected from a range of about 0.01 M to about 0.03 M.

The engineered collagen matrices, including collagen-binding synthetic peptidoglycans, of the present invention can be combined, prior to, during, or after polymerization, with nutrients, including minerals, amino acids, sugars, peptides, proteins, vitamins (such as ascorbic acid), or other compounds such as laminin and fibronectin, hyaluronic acid, fibrin, elastin, and aggrecan, or growth factors such as epidermal growth factor, platelet-derived growth factor, transforming growth factor beta, vascular endothelial growth factor, or fibroblast growth factor, and glucocorticoids such as dexamethasone, or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

In accordance with one embodiment, cells can be added as the last step prior to the polymerization or after polymerization of the engineered collagen matrix. In other illustrative embodiments, cross-linking agents, such as carbodiimides, aldehydes, lysl-oxidase, N-hydroxysuccinimide esters, imidoesters, hydrazides, and maleimides, and the like can be added before, during, or after polymerization.

In one embodiment, the engineered collagen matrix is formed using commercially available collagen (e.g., Sigma, St. Louis, Mo.). In an alternative embodiment, the collagen can be purified from submucosa-containing tissue material such as intestinal, urinary bladder, or stomach tissue. In a further embodiment, the collagen can be purified from tail tendon. In a further embodiment, the collagen can be purified from skin.

In one embodiment, the collagen-binding synthetic peptidoglycans with amino acid homology to a portion of the amino acid sequence of a proteoglycan that normally regulates collagen fibrillogenesis or with amino acid homology to a portion of a protein or a peptide that does not normally regulate fibrillogenesis, can be used to form an engineered collagen matrix with desired structural or mechanical characteristics. In another embodiment, the aberrant collagen-binding synthetic peptidoglycans or fibrillogenic collagen-binding synthetic peptidoglycans can be used to form an engineered collagen matrix with desired, but altered structure or mechanical characteristics.

The desired structural, microstructural, nanostructural, or mechanical characteristics can, illustratively, include fibril length, fibril diameter, fibril density, fibril volume fraction, fibril organization, 3-dimensional shape or form, and viscoelastic, tensile, shear, or compressive behavior (e.g., failure stress, failure strain, and modulus), permeability, degradation rate, swelling, hydration properties (e.g., rate and swelling), and in vivo tissue remodeling properties, and desired in vitro and in vivo cell responses. The engineered graft constructs and engineered collagen matrices described herein can have desirable biocompatibility and in vitro and in vivo remodeling properties, among other desirable properties.

As used herein, a "modulus" can be an elastic or linear modulus (defined by the slope of the linear region of the stress-strain curve obtained using conventional mechanical testing protocols; i.e., stiffness), a compressive modulus, a complex modulus, or a shear storage modulus.

As used herein, a "fibril volume fraction" is defined as the percent area of the total area occupied by fibrils in a cross-sectional surface of the matrix in 3 dimensions and "void space fraction" is defined as the percent area of the total area not occupied by fibrils in a cross-sectional surface of the matrix in 3 dimensions.

The engineered collagen matrices described herein comprise collagen fibrils which typically pack in a quarter-staggered pattern giving the fibril a characteristic striated appearance or banding pattern along its axis. In various illustrative embodiments, qualitative and quantitative microstructural characteristics of the engineered collagen matrices can be determined by scanning electron microscopy, transmission electron microscopy, confocal microscopy, second harmonic generation multi-photon microscopy. In another embodiment, tensile, compressive and viscoelastic properties can be determined by rheometry or tensile testing. All of these methods are known in the art or are further described in the Examples section of this application or in Roeder et al., J. Biomech. Eng., vol. 124, pp. 214-222 (2002), in Pizzo et al., J. Appl. Physiol., vol. 98, pp. 1-13 (2004), Fulzele et al., Eur. J. Pharm. Sci., vol. 20, pp. 53-61 (2003), Griffey et al., J. Biomed. Mater. Res., vol. 58, pp. 10-15 (2001), Hunt et al., Am. J. Surg., vol. 114, pp. 302-307 (1967), and Schilling et al., Surgery, vol. 46, pp. 702-710 (1959), incorporated herein by reference.

In any of the above-described engineered collagen matrix, engineered graft construct, kit, or method embodiments, the collagen-binding synthetic peptidoglycan can be a compound of any of the following formulas A) $P_nG_x$ wherein n is 1 to 10;
   wherein x is 1 to 10;
   wherein P is a synthetic peptide of about 5 to about 40 amino acids comprising a sequence of a collagen-binding domain; and
   wherein G is a glycan.
OR
B) $(P_nL)_xG$ wherein n is 1 to 5;
   wherein x is 1 to 10;
   wherein P is a synthetic peptide of about 5 to about 40 amino acids comprising a sequence of a collagen-binding domain;
   wherein L is a linker; and
   wherein G is a glycan.
OR
C) $P(LG_n)_x$ wherein n is 1 to 5;
   wherein x is 1 to 10;
   wherein P is a synthetic peptide of about 5 to about 40 amino acids comprising a sequence of a collagen-binding domain;
   wherein L is a linker; and
   wherein G is a glycan.

In alternative embodiments, a compound of any of the following formulas is provided
A) $P_nG_x$ wherein n is 1 to 10;
   wherein x is 1 to 10;
   wherein P is a synthetic peptide of about 5 to about 40 amino acids comprising a sequence of a collagen-binding domain; and
   wherein G is a glycan.
OR
B) $(P_nL)_xG$ wherein n is 1 to 5;
   wherein x is 1 to 10;
   wherein P is a synthetic peptide of about 5 to about 40 amino acids comprising a sequence of a collagen-binding domain;
   wherein L is a linker; and
   wherein G is a glycan.
OR
C) $P(LG_n)_x$ wherein n is 1 to 5;
   wherein x is 1 to 10;
   wherein P is a synthetic peptide of about 5 to about 40 amino acids comprising a sequence of a collagen-binding domain;
   wherein L is a linker; and
   wherein G is a glycan.

In another embodiment, a collagen-binding synthetic peptidoglycan comprising a synthetic peptide of about 5 to about 40 amino acids with amino acid sequence homology to a collagen binding peptide (e.g. a portion of an amino acid sequence of a collagen binding protein or proteoglycan) conjugated to heparin, dextran, or hyaluronan can be used to inhibit platelet activation, to inhibit platelet binding to collagen, or to limit thrombosis or to form an engineered collagen matrix. In any of these embodiments, any of the above-described compounds can be used.

In another embodiment, a collagen-binding synthetic peptidoglycan comprising a synthetic peptide of about 5 to about 40 amino acids with amino acid sequence homology to a collagen binding peptide (e.g. a portion of an amino acid sequence of a collagen binding protein or proteoglycan) conjugated to heparin, dextran, or hyaluronan can be used to inhibit platelet binding to collagen, platelet activation, or both. In any of these embodiments, any of the above-described compounds can be used.

In another embodiment, the synthetic peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts as the side chain of the amino acid which has been replaced.

Non-conservative substitutions are possible provided that these do not excessively affect the collagen binding activity of the peptide and/or reduce its effectiveness in altering the structure or mechanical characteristics of a collagen matrix, in inhibiting platelet activation, or in inhibiting platelet adhesion (e.g. binding) to collagen.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in TABLE 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In another embodiment, a collagen-binding synthetic peptidoglycan comprising a synthetic peptide of about 5 to about 40 amino acids with amino acid sequence homology to a portion of a collagen binding peptide conjugated to heparin can be used to inhibit platelet activation, inhibit platelet binding (e.g. adhesion) to collagen, or to limit thrombosis or to form an engineered collagen matrix. In another embodiment, the collagen-binding synthetic peptidoglycan conjugated to dextran can be used to inhibit platelet activation, inhibit platelet binding to collagen, or to limit thrombosis or to form an engineered collagen matrix. In yet another embodiment, the collagen-binding synthetic peptidoglycan conjugated to hyaluronan can be used to inhibit platelet activation, inhibit platelet binding to collagen, or to limit thrombosis or to form an engineered collagen matrix. In any of these embodiments, any of the above-described compounds can be used.

In another embodiment, a collagen-binding synthetic peptidoglycan comprising a synthetic peptide of about 5 to about 40 amino acids with amino acid sequence homology to a collagen binding peptide (e.g. a portion of an amino acid sequence of a collagen binding protein or a proteoglycan) conjugated to any glycan, such as, for example, heparin, dextran, or hyaluronan can be used to inhibit platelet binding to collagen, to inhibit platelet activation, or to limit thrombosis. In any of these embodiments, any of the above-described compounds can be used.

In one embodiment the synthetic peptide is synthesized according to solid phase peptide synthesis protocols that are well known by persons of skill in the art. In one embodiment a peptide precursor is synthesized on a solid support according to the well-known Fmoc protocol, cleaved from the support with trifluoroacetic acid and purified by chromatography according to methods known to persons skilled in the art.

In another embodiment the synthetic peptide is synthesized utilizing the methods of biotechnology that are well known to persons skilled in the art. In one embodiment a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium according to methods known by persons skilled in the art (e.g., by affinity purification). Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

In one embodiment the synthetic peptide is conjugated to a glycan by reacting a free amino group of the peptide with an aldehyde function of the glycan in the presence of a reducing agent, utilizing methods known to persons skilled in the art, to yield the peptide glycan conjugate. In one embodiment an aldehyde function of the glycan (e.g. polysaccharide or glycosaminoglycan) is formed by reacting the glycan with sodium metaperiodate according to methods known to persons skilled in the art.

In another embodiment the synthetic peptide is conjugated to a glycan by reacting an aldehyde function of the glycan with 3-(2-pyridyldithio)propionyl hydrazide (PDPH) to form an intermediate glycan and further reacting the intermediate glycan with a peptide containing a free thiol group to yield the peptide glycan conjugate. In yet another embodiment, the sequence of the peptide may be modified to include a glycine-cysteine segment to provide an attachment point for a glycan or a glycan-linker conjugate.

Although specific embodiments have been described in the preceding paragraphs, the collagen-binding synthetic peptidoglycans described herein can be made by using any art-recognized method for conjugation of the peptide to the glycan (e.g. polysaccharide or glycosaminoglycan). This can include covalent, ionic, or hydrogen bonding, either directly or indirectly via a linking group such as a divalent linker. The conjugate is typically formed by covalent bonding of the peptide to the glycan through the formation of amide, ester or imino bonds between acid, aldehyde, hydroxy, amino, or hydrazo groups on the respective components of the conjugate. All of these methods are known in the art or are further described in the Examples section of this application or in Hermanson G. T., Bioconjugate Techniques, Academic Press, pp. 169-186 (1996). The linker typically comprises about 1 to about 30 carbon atoms, more typically about 2 to about 20 carbon atoms. Lower molecular weight linkers (i.e., those having an approximate molecular weight of about 20 to about 500) are typically employed.

In addition, structural modifications of the linker portion of the conjugates are contemplated herein. For example, amino acids may be included in the linker and a number of amino acid substitutions may be made to the linker portion of the conjugate, including but not limited to naturally occurring amino acids, as well as those available from conventional synthetic methods. In another aspect, beta, gamma, and longer chain amino acids may be used in place of one or more alpha amino acids. In another aspect, the linker may be shortened or lengthened, either by changing the number of amino acids included therein, or by including more or fewer beta, gamma, or longer chain amino acids. Similarly, the length and shape of other chemical fragments of the linkers described herein may be modified.

In one aspect, the linker may include one or more bivalent fragments selected independently in each instance from the group consisting of alkylene, heteroalkylene, cycloalkylene, cycloheteroalkylene, arylene, and heteroarylene each of which is optionally substituted. As used herein heteroalkylene represents a group resulting from the replacement of one or more carbon atoms in a linear or branched alkylene group with an atom independently selected in each instance from the group consisting of oxygen, nitrogen, phosphorus and sulfur.

In one aspect, a collagen-binding synthetic peptidoglycan may be administered to a patient (e.g., a patient in need of treatment to inhibit platelet activation such as that involved in thrombosis). In various embodiments, the collagen-binding synthetic peptidoglycan can be administered intravenously, or into muscle, or an internal organ, for example. Suitable routes for parenteral administration include intravenous, intra-arterial, and intramuscular delivery. Suitable means for parenteral administration include needle (including microneedle) injectors and infusion techniques.

In an illustrative embodiment, pharmaceutical formulations for use with collagen-binding synthetic peptidoglycans for parenteral administration comprising: a) a pharmaceutically active amount of the collagen-binding synthetic peptidoglycan; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any combinations of a), b), c) and d) are provided.

In various illustrative embodiments, the pH buffering agents for use in the compositions and methods herein described are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In another illustrative embodiment, the ionic strength modulating agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and non-ionic water soluble polymers; crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or basic agent are employed in order to facilitate achieving the desired pH of the formulation.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

In one embodiment, the solubility of a collagen-binding synthetic peptidoglycan used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a collagen-binding synthetic peptidoglycan may be formulated as a solid, semisolid, or thixotropic liquid for administration as an implanted depot providing modified release of the active compound. Illustrative examples of such formulations include drug-coated stents and copolymeric(dl-lactic, glycolic)acid (PGLA) microspheres. In another embodiment, collagen-binding synthetic peptidoglycans or compositions comprising collagen-binding synthetic peptidoglycan may be continuously administered, where appropriate.

In other embodiments, collagen-binding synthetic peptidoglycans and compositions containing them can be administered topically. A variety of dose forms and bases can be applied to the topical preparations, such as an ointment, cream, gel, gel ointment, plaster (e.g. cataplasm, poultice), solution, powders, and the like. These preparations may be prepared by any conventional method with conventional pharmaceutically acceptable carriers or diluents as described below.

For example, in the preparation of an ointment, vaseline, higher alcohols, beeswax, vegetable oils, polyethylene glycol, etc. can be used. In the preparation of a cream formulation, fats and oils, waxes, higher fatty acids, higher alcohols, fatty acid esters, purified water, emulsifying agents etc. can be used. In the preparation of gel formulations, conventional gelling materials such as polyacrylates (e.g. sodium polyacrylate), hydroxypropyl cellulose, hydroxypropyl methyl cellulose, polyvinyl alcohol, polyvinylpyrrolidone, purified water, lower alcohols, polyhydric alcohols, polyethylene glycol, and the like are used. In the preparation of a gel ointment preparation, an emulsifying agent (preferably nonionic surfactants), an oily substance (e.g. liquid paraffin, triglycerides, and the like), etc. are used in addition to the gelling materials as mentioned above. A plaster such as cataplasm or poultice can be prepared by spreading a gel preparation as mentioned above onto a support (e.g. fabrics, non-woven fabrics). In addition to the above-mentioned ingredients, paraffins, squalane, lanolin, cholesterol esters, higher fatty acid esters, and the like may optionally be used. Moreover, antioxidants such as BHA, BHT, propyl gallate, pyrogallol, tocopherol, etc. may also be incorporated. In addition to the above-mentioned preparations and components, there may optionally be used any other conventional formulations for incorporated with any other additives.

It is also contemplated that any of the formulations described herein may be used to administer the collagen-binding synthetic peptidoglycan (e.g., one or more types)

either in the absence or the presence of the engineered collagen matrices described herein.

In various embodiments, the dosage of the collagen-binding synthetic peptidoglycan, with or without an engineered collagen matrix, can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, an effective dose can range from about 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses can range from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose.

Any effective regimen for administering the collagen-binding synthetic peptidoglycan can be used. For example, the collagen-binding synthetic peptidoglycan can be administered as a single dose, or as a multiple-dose daily regimen. Further, a staggered regimen, for example, one to five days per week can be used as an alternative to daily treatment.

In one embodiment of the invention the patient is treated with multiple injections of the collagen-binding synthetic peptidoglycan. In one embodiment, the patient is injected multiple times (e.g., about 2 up to about 50 times) with the collagen-binding synthetic peptidoglycan, for example, at 12-72 hour intervals or at 48-72 hour intervals. Additional injections of the collagen-binding synthetic peptidoglycan can be administered to the patient at an interval of days or months after the initial injections(s) and the additional injections prevent recurrence of disease. Alternatively, the initial injection(s) of the collagen-binding synthetic peptidoglycan may prevent recurrence of disease.

In any of the embodiments herein described, it is to be understood that a combination of two or more collagen-binding synthetic peptidoglycans, differing in the peptide portion, the glycan portion, or both, can be used in place of a single collagen-binding synthetic peptidoglycan.

It is also appreciated that in the foregoing embodiments, certain aspects of the compounds, compositions and methods are presented in the alternative in lists, such as, illustratively, selections for any one or more of G and P. It is therefore to be understood that various alternate embodiments of the invention include individual members of those lists, as well as the various subsets of those lists. Each of those combinations are to be understood to be described herein by way of the lists.

In the following illustrative examples, the terms "synthetic peptidoglycan" and "conjugate" are used synonymously with the term "collagen-binding synthetic peptidoglycan."

Example 1

Peptide Synthesis

All peptides were synthesized using a Symphony peptide synthesizer (Protein Technologies, Tucson, Ariz.), utililizing an FMOC protocol on a Knorr resin. The crude peptide was released from the resin with TFA and purified by reverse phase chromatography on an AKTAexplorer (GE Healthcare, Piscataway, N.J.) utililizing a Grace-Vydac 218TP C-18 reverse phase column and a gradient of water/acetonitrile 0.1% TFA. Dansyl-modified peptides were prepared by adding an additional coupling step with dansyl-Gly (Sigma) before release from the resin. Peptide structures were confirmed by mass spectrometry. The following peptides were prepared as described above: RRANAALKAGELYKSILYGC [SEQ ID NO: 1], SYIRIADTNIT [SEQ ID NO: 10], Dansyl-GRRANAALKAGELYKSILYGC [SEQ ID NO: 15], and Dansyl-GSYIRIADTNIT [SEQ ID NO: 16]. These peptides are abbreviated SILY, SYIR, Z-SILY, and Z-SYIR. Additional peptides, KELNLVYTGC [SEQ ID NO: 12] (abbreviated KELN) and GSITTIDVPWNVGC [SEQ ID NO: 14] (abbreviated GSIT) were prepared as described above or purchased (Genescript, Piscataway, N.J.).

Example 2

Conjugation of SYIR Peptide to Dermatan Sulfate

SYIR was conjugated to oxDS by a method adapted from Hermanson with slight modifications (Hermanson, 1996). The peptide SYIR was dissolved in 0.05M sodium carbonate, 0.1M sodium citrate buffer, pH 9.5, at a concentration of 0.4 mg/mL for a final volume of 5 mL. To react in 10-fold peptide molar excess, 29 mg of oxDS MW 41,000 (oxidized dermatan sulfate, containing 1.1 aldehydes/DS molecule of 41 kDa is available from Celsus Laboratories, Cincinnati, Ohio) was dissolved into the peptide solution. Under gentle stiffing, 50 µL sodium cyanoborohydride was added, and the reaction allowed to proceed at room temperature overnight.

Excess peptide was separated by gel filtration on an Akta Purifier using an XK 26-40 column packed with Sephadex G-25 medium (GE Health) and equilibrated with deionized water (MilliQ). Eluent was monitored at 215 nm, 254 nm, and 280 nm. The first eluting peak containing DS-SYIR was collected and lyophilized for further testing.

Example 3

Conjugation of SILY to Dermatan Sulfate

PDPH Attachment to oxDS

The bifunctional crosslinker PDPH (Pierce), reactive to sulfhydryl and amine groups, was used to conjugate SILY to oxDS. In the first step of the reaction, oxDS was dissolved in coupling buffer (0.1M sodium phosphate, 0.25M sodium chloride, pH 7.2) to a final concentration of 1.2 mM. PDPH was added in 10-fold molar excess, and the reaction proceeded at room temperature for 2 hours. Excess PDPH (MW 229Da) was separated by gel filtration on an Akta Purifier using an XK 26-40 column packed with Sephadex G-25 medium and equilibrated with MilliQ water. Eluent was monitored at 215 nm, 254 nm, and 280 nm. The first eluting peak containing DS-PDPH was collected and lyophilized for conjugating with SILY.

Determination of PDPH Content

Figure 7:
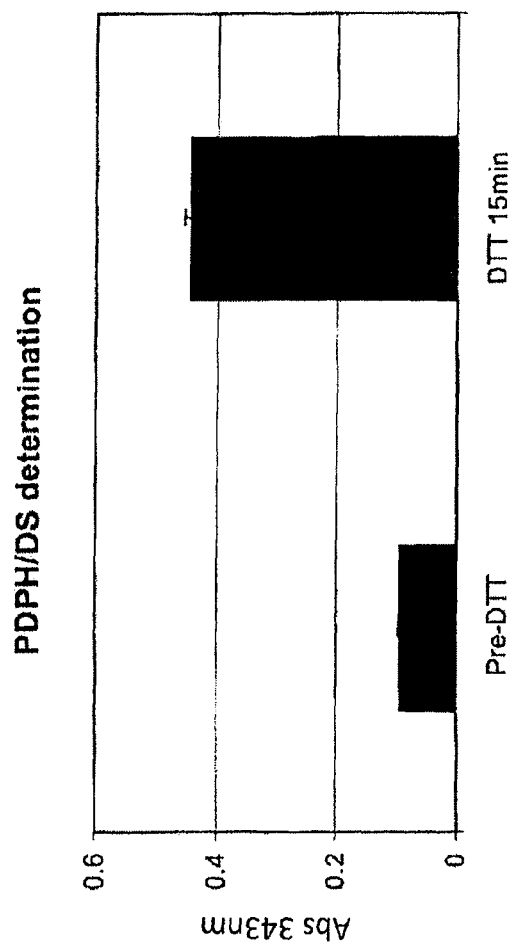
FIG. 7. Measurement of absorbance at 343 nm before DTT treatment of oxidized dermatan sulfate conjugated to PDPH, and after treatment with DTT, which releases 2-pyridylthiol from the conjugate. The measurements allow determination of the ratio of PDPH to oxidized dermatan sulfate. The measured ΔA=0.35, corresponds to 1.1 PDPH molecules/DS.

To determine the number of PDPH molecules conjugated to oxDS. DS-PDPH was dissolved in coupling buffer at 1.6 mg/mL. 10 µL of DTT at 15 mg/mL was added to the DS-PDPH solution, and the reaction proceeded at room temperature for 15 min Reducing the disulfide bond on the cysteine reactive side of PDPH liberates pyridine-2-thione, which is visible at 313 nm Absorbance at 313 nm was measured before and after the addition of DTT, and the difference was used to calculate the number of PDPH molecules/DS molecule using the extinction coefficient of pyridine-2-thione. Results in FIG. 7 show ΔA=0.35, corresponding to 1.1 PDPH molecules/DS.

Conjugation of SILY

Figure 26:
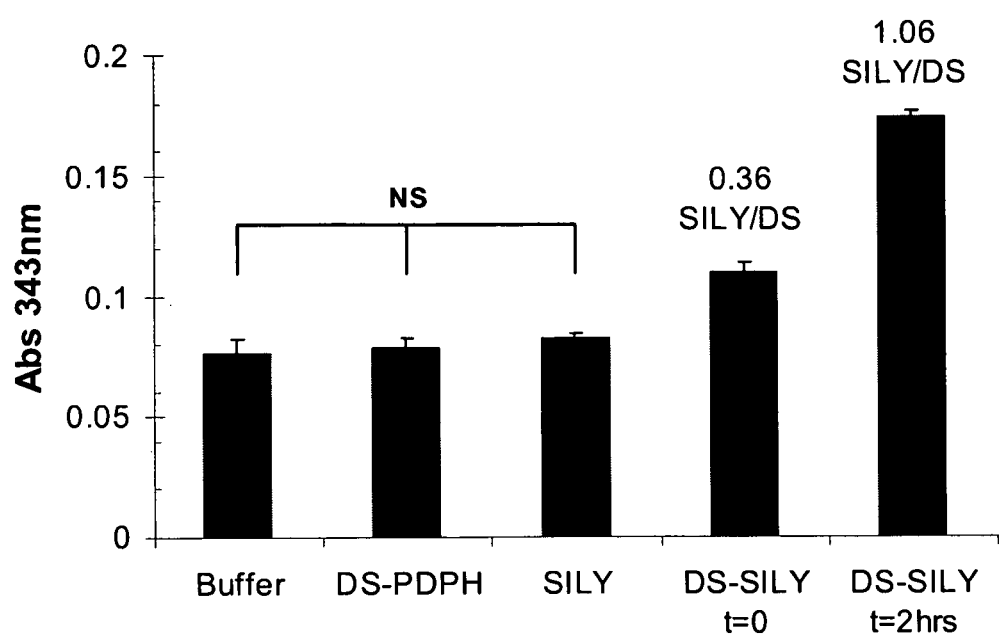
FIG. 26. DS-SILY Conjugation Characterization. After 2 hours, a final $\Delta A_{343\ nm}$ corresponded to 1.06 SILY molecules added to each DS molecule. Note, t=0 is an approximate zero time point due to the slight delay between addition of SILY to the DS-PDPH and measurement of the solution at 343 nm.

The peptide was dissolved in a 5:1 molar excess in coupling buffer at a final peptide concentration of approximately 1mM (limited by peptide solubility). The reaction was allowed to proceed at room temperature overnight, and excess peptide was separated and the DS-SILY conjugate isolated by gel filtration as described above. See FIG. 26 showing a SILY/DS ratio of 1.06 after coupling.

Example 4

Conjugation of Z-SILY to Dermatan Sulfate

Dermatan sulfate was conjugated to Z-SILY according to the method of EXAMPLE 3.

Example 5

Conjugation of KELN to Dermatan Sulfate

Dermatan sulfate was conjugated to KELN according to the method of EXAMPLE 3.

Example 6

Conjugation of GSIT to Dermatan Sulfate

Dermatan sulfate was conjugated to GSIT according to the method of EXAMPLE 3.

Example 7

Conjugation of Z-SYIR to Dermatan Sulfate

Dermatan sulfate was conjugated to Z-SYIR according to the method of EXAMPLE 2.

Example 8

Conjugation of SILY to Heparin

Oxidized Heparin (oxHep) (MW=19.7 kDa) containing 1 aldehyde per molecule (purchased from Celsus Laboratories, Cincinnati, Ohio). Additional aldehydes were formed by further oxidation in sodium meta-periodate as follows. oxHep was dissolved in 0.1M sodium acetate pH 5.5 at a concentration of 10 mg/mL. Sodium meta-periodate was then added at a concentration of 2 mg/mL and allowed to react for 4 hours at room temperature protected from light. Excess sodium meta-periodate was removed by desalting using a HiTrap size exclusion column (GE Healthcare) and oxHep was lyophilized protected from light until conjugation with PDPH.

oxHep was conjugated to PDPH by the method described for DS-PDPH conjugation, EXAMPLE 3. PDPH was reacted in 50-fold molar excess. To achieve a higher PDPH concentration, 10 mg PDPH was dissolved in 75 µL DMSO and mixed with 1 mL coupling buffer containing oxHep. The reaction proceeded at room temperature for 2.5 hours and excess PDPH was removed by desalting. Heparin containing PDPH (Hep-PDPH) was stored as a lyophilized powder until reacted with SILY.

Figure 24:
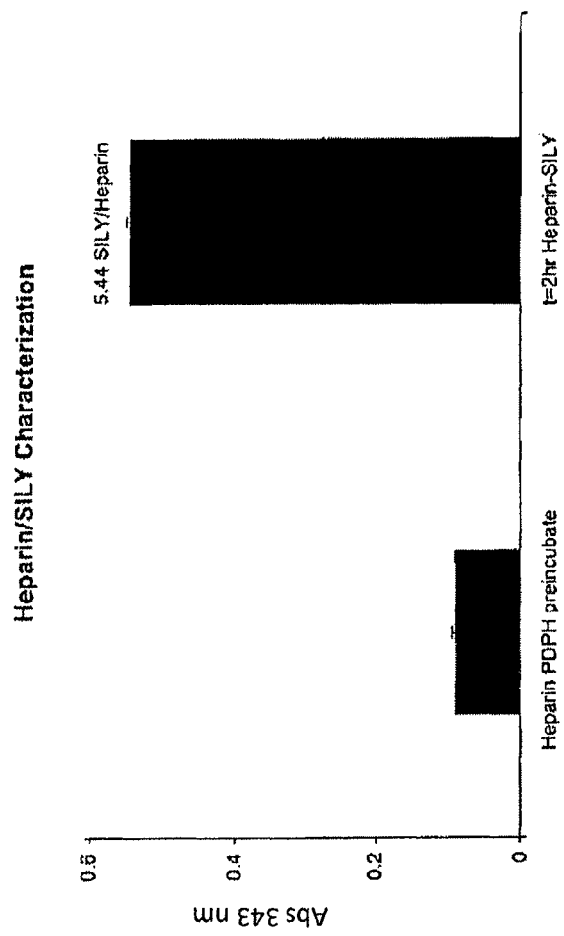
FIG. 24. Measurement of absorbance at 343 nm before treatment of oxidized heparin conjugated to PDPH, and after treatment with SILY, which releases 2-pyridylthiol from the conjugate and allows determination of the ratio of SILY peptide conjugated to oxidized heparin. The measured AA, corresponds to 5.44 SILY molecules/oxidized heparin.

SILY was reacted in 10-fold molar excess with Hep-PDPH as described for DS-SILY conjugation in EXAMPLE 3. The reaction was monitored as described for DS-SILY in EXAMPLE 3 and showed 5.44 SILY peptides conjugated per heparin molecule as shown in FIG. 24.

Example 9

Conjugation of GSIT to Heparin

Heparin was conjugated to GSIT according to the method of EXAMPLE 8 (abbreviated Hep-GSIT).

Example 10

Conjugation of SILY to Dextran

Dextran was conjugated to SILY according to the method of EXAMPLE 8 replacing heparin with dextran. Modification of the conditions for oxidation of dextran with sodium meta-periodate in the first step to allowed preparation of conjugates with different molar ratios of SILY to dextran. For example dextran-SILY conjugates with a molar ratio of SILY to dextran of about 6 and a dextran-SILY conjugate with a molar ratio of SILY to dextran of about 9 were prepared (abbreviated Dex-SILY6 and Dex-SILY9).

Example 11

Conjugation of SILY to Hyaluronan

Hyaluronan was conjugated to SILY according to the method of EXAMPLE 8 (abbreviated IIA-SILY).

Example 12

SILY Binding to Collagen (Biacore)

Biacore studies were performed on a Biacore 2000 using a CM-3 chip (Biacore, Inc., Piscataway, N.J.). The CM-3 chip is coated with covalently attached carboxymethylated dextran, which allows for attachment of the substrate collagen via free amine groups. Flow cells (FCs) 1 and 2 were used, with FC-1 as the reference cell and FC-2 as the collagen immobilized cell. Each FC was activated with EDC-NHS, and 1500 RU of collagen was immobilized on FC-2 by flowing 1 mg/mL collagen in sodium acetate, pH 4, buffer at 5 µL/min for 10 min. Unreacted NHS-ester sites were capped with ethanolamine; the control FC-1 was activated and capped with ethanolamin.

Figure 3:
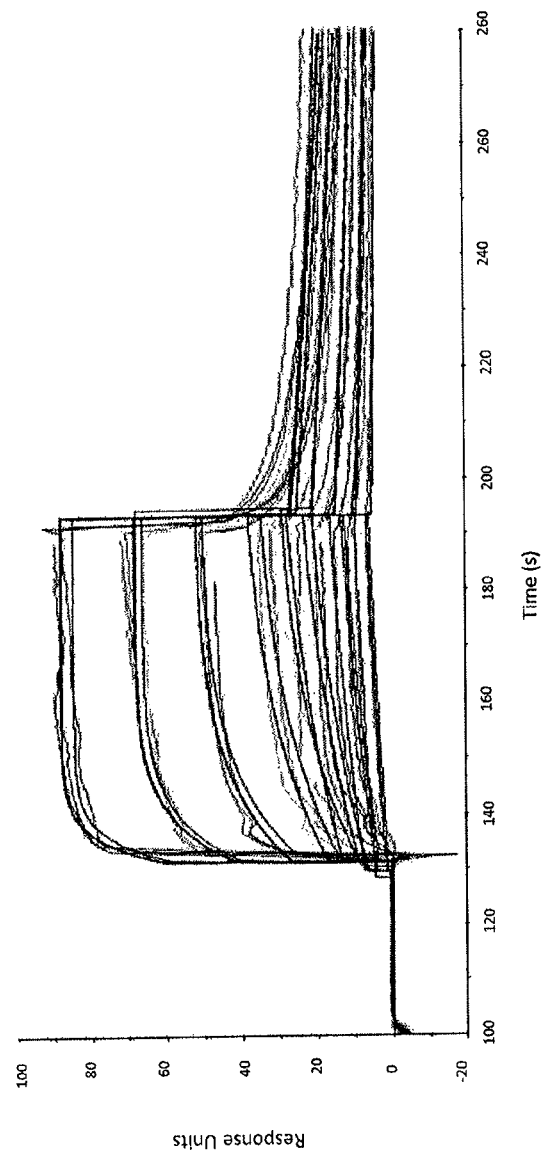
FIG. 3. Surface Plasmon Resonance scan in association mode and dissociation mode of peptide RRANAALKAGE-LYKSILYGC [SEQ ID NO: 1] (SILY) binding to collagen bound to CM-3 plates. SILY was dissolved in 1×HBS-EP buffer at varying concentrations from 100 μM to 1.5 μm in 2-fold dilutions.

To determine peptide binding affinity, SILY was dissolved in 1×HBS-EP buffer (Biacore) at varying concentrations from 100 uM to 1.5 µm in 2-fold dilutions. The flow rate was held at 90 µL/min which is in the range suggested by Myska for determining binding kinetics (Myska, 1997). The first 10 injections were buffer injections, which help to prime the system, followed by randomized sample injections, run in triplicate. Analysis was performed using BIAevaluation software (Biacore). Representative association/disassociation curves are shown in FIG. 3 demonstrating that the SILY peptide binds reversibly with collagen. $K_D$=1.2 µM was calculated from the on-off binding kinetics.

Example 13

Z-SILY Binding to Collagen

Figure 4:
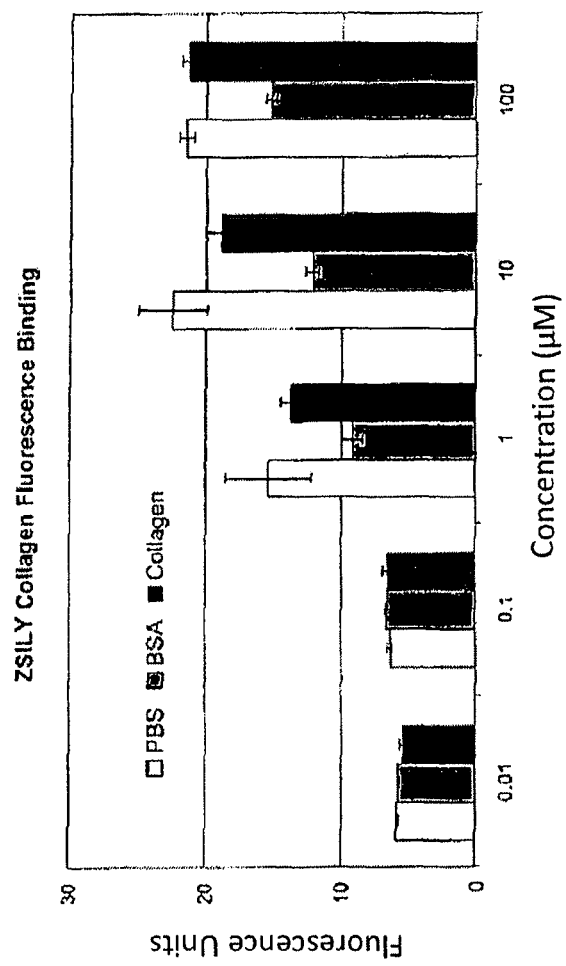
FIG. 4. Binding of dansyl-modified peptide SILY to collagen measured in 96-well high-binding plate (black with a clear bottom (Costar)). PBS, buffer only; BSA, BSA-treated well; Collagen, collagen-treated well. Fluorescence readings were taken on an M5 Spectramax Spectrophotometer (Molecular Devices) at excitation/emission wavelengths of 335 nm/490 nm, respectively.
Figure 5:
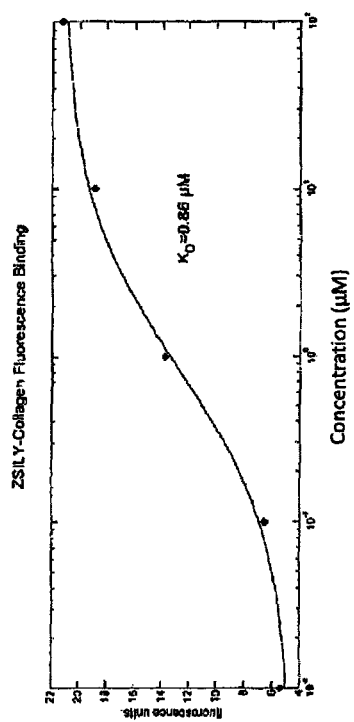
FIG. 5. Collagen-dansyl-modified peptide SILY binding curve derived from fluorescence data described in FIG. 4.
Figure 6:
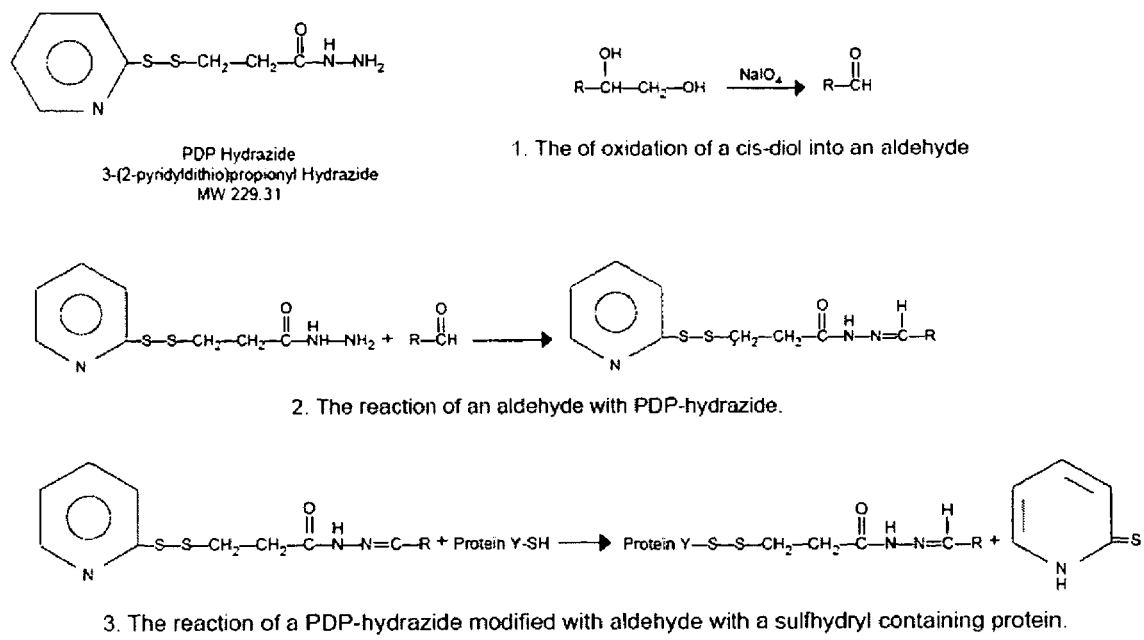
FIG. 6. A schematic description of the reagent, 3-(2-pyridyldithio)propionyl hydrazide (PDPH), and the chemistry of the two-step conjugation of a cysteine-containing peptide with an oxidized glycosylaminoglycoside showing the release of 2-pyridylthiol in the final step.

Binding assays were done in a 96-well high-binding plate, black with a clear bottom (Costar). Collagen was compared to untreated wells and BSA coated wells. Collagen and BSA were immobilized at 37° C. for 1 hr by incubating 90 µL/well at concentrations of 2 mg/mL in 10 mM HCl and 1×PBS, respectively. Each well was washed 3× with 1×PBS after incubating. Z-SILY was dissolved in 1×PBS at concentrations from 100 µM to 10 nM in 10-fold dilutions. Wells were incubated for 30 min at 37° C. and rinsed 3× with PBS and then filled with 90 µL of 1×PBS. Fluorescence readings were taken on an M5 Spectramax Spectrophotometer (Molecular Devices) at excitation/emission wavelengths of 335 nm/490 nm respectively. The results are shown in FIGS. 4 and 5. $K_D$=0.86 µM was calculated from the equilibrium kinetics.

Example 14

Charaterizing DS-SILY

To determine the number of SILY molecules conjugated to DS, the production of pyridine-2-thione was measured using a modified protocol provided by Pierce. Dermatan sulfate with 1.1 PDPH molecules attached was dissolved in coupling buffer (0.1M sodium phosphate, 0.25M sodium chloride) at a concentration of 0.44 mg/mL and absorbance at 343 nm was measured using a SpectraMax M5 (Molecular Devices). SILY was reacted in 5-fold molar excess and absorbance measurements were repeated immediately after addition of SILY and after allowing to react for 2 hours. To be sure SILY does not itself absorb at 343 nm, coupling buffer containing 0.15 mg/mL SILY was measured and was compared to absorbance of buffer alone.

The number of SILY molecules conjugated to DS was calculated by the extinction coefficient of pyridine-2-thione using the following equation $(Abs_{343}/8080) \times (MW_{DS}/DS_{mg/mL})$. The results are shown in FIG. 26.

Example 15

Collagen Binding, Fluorescence Data—DS-SILY

In order to determine whether the peptide conjugate maintained its ability to bind to collagen after its conjugation to DS, a fluorescent binding assay was performed. A fluorescently labeled version of SILY, Z-SILY, was synthesized by adding dansylglycine to the amine terminus. This peptide was conjugated to DS and purified using the same methods described for SILY.

Binding assays were done in a 96-well high binding plate, black with a clear bottom (Costar). Collagen was compared to untreated wells and BSA coated wells. Collagen and BSA were immobilized at 37° C. for 1 hr by incubating 90 µL/well at concentrations of 2 mg/mL in 10 mM HCl and 1×PBS respectively. Each well was washed 3× with 1×PBS after incubating.

Wells were preincubated with DS at 37° C. for 30 min to eliminate nonspecific binding of DS to collagen. Wells were rinsed 3× with 1×PBS before incubating with DS-Z-SILY. DS-Z-SILY was dissolved in 1×PBS at concentrations from 100 µM to 10 nM in 10-fold dilutions. Wells were incubated for 30 min at 37° C. and rinsed 3× and then filled with 90 µL of 1×PBS. Fluorescence readings were taken on an M5 Spectramax Spectrophotometer (Molecular Devices) at excitation/emission wavelengths of 335 nm/490 nm respectively.

Figure 8:
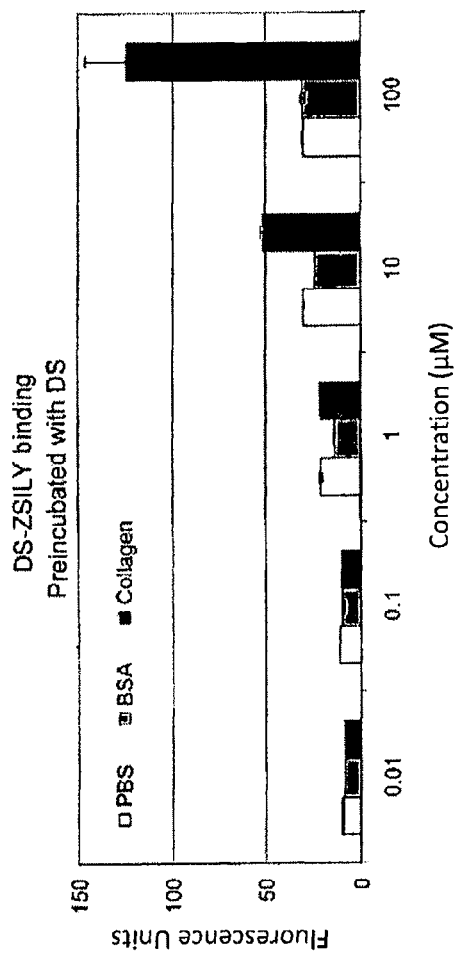
FIG. 8. Binding of dansyl-modified peptide SILY conjugated to dermatan sulfate as described herein to collagen measured in 96-well high-binding plate (black with a clear bottom (Costar)). PBS, buffer only; BSA, BSA-treated well; Collagen, collagen-treated well. Fluorescence readings were taken on an M5 Spectramax Spectrophotometer (Molecular Devices) at excitation/emission wavelengths of 335 nm/490 nm respectively.

Fluorescence binding of DS-Z-SILY on immobilized collagen, BSA, and untreated wells are compared in FIG. 8. Results show that DS-Z-SILY binds specifically to the collagen-treated wells over BSA and untreated wells. The untreated wells of the high bind plate were designed to be a positive control, though little binding was observed relative to collagen treated wells. These results suggest that SILY maintains its ability to bind to collagen after it is conjugated to DS. Preincubating with DS did not prevent binding, suggesting that the conjugate binds separately from DS alone.

Example 16

Preparation Of Type I Collagen Gels

Gels were made with Nutragen collagen (Inamed, Freemont, Calif.) at a final concentration of 4 mg/mL collagen. Nutragen stock is 6.4 mg/mL in 10 mM HCl. Gel preparation was performed on ice, and fresh samples were made before each test. The collagen solution was adjusted to physiologic pH and salt concentration, by adding appropriate volumes of 10×PBS (phosphate buffered saline), 1×PBS, and 1M NaOH. For most experiments, samples of DS, decorin, DS-SILY, or DS-SYIR were added at a 10:1 collagen:sample molar ratio by a final 1×PBS addition (equal volumes across treatments) in which the test samples were dissolved at appropriate concentrations. In this way, samples are constantly kept at pH 7.4 and physiologic salt concentration. Collagen-alone samples received a 1×PBS addition with no sample dissolved. Fibrillogenesis will be induced by incubating neutralized collagen solutions at 37° C. overnight in a humidified chamber to avoid dehydration. Gel solutions with collagen:sample molar ratios of other than 10:1 were prepared similarly.

Example 17

Viscoelastic Characterization of Gels

Collagen gels were prepared as described in EXAMPLE 16 and prior to heating, 200 µl of each treatment were pipetted onto the wettable surface of hydrophobically printed slides (Tekdon). The PTFE printing restricted gels to the 20 mm diameter wettable region. Gels were formed in a humidified incubator at 37° C. overnight prior to mechanical testing.

Figure 9:
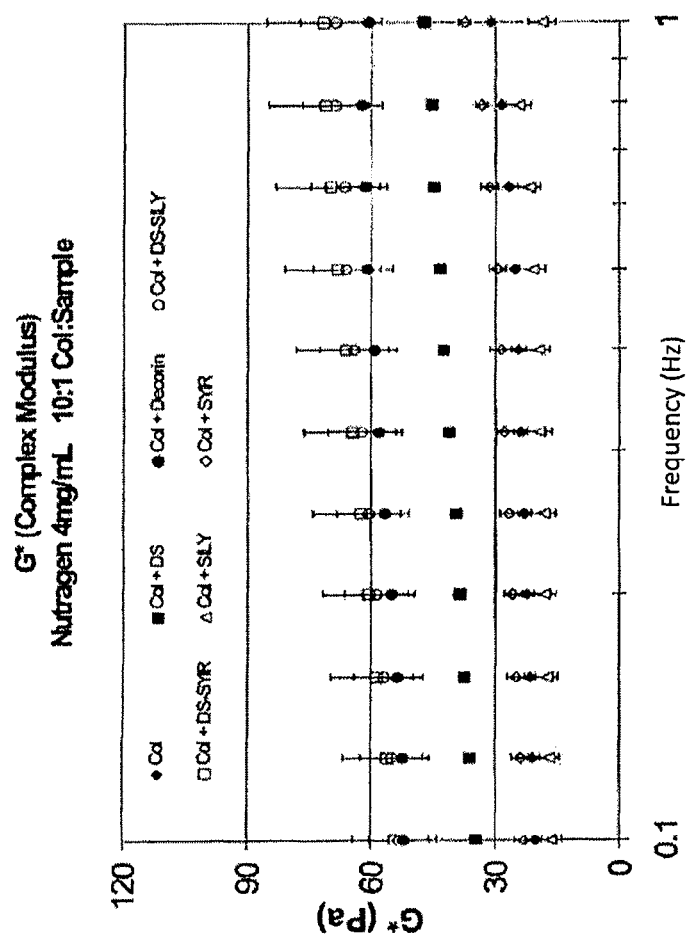
FIG. 9. Measurement of Shear modulus of gel samples (4 mg/mL collagen, 10:1 collagen:treatment) on a AR-G2 rheometer with 20 mm stainless steel parallel plate geometry (TA Instruments, New Castle, Del.), and the 20 mm stainless steel parallel plate geometry was lowered to a gap distance of 600 μm using a normal force control of 0.25N. Col, no treatment, i.e. collagen alone; Col+DS, collagen+dermatan sulfate; Col+decorin, collagen+decorin; Col+DS-SYIR, collagen+dermatan sulfate-SYIR; Col+DS-SILY, collagen+dermatan sulfate-SILY conjugate; Col+SILY, collagen+SILY peptide; Col+SYIR, collagen+SYIRIADTNIT [SEQ ID NO: 10] (SYIR) peptide.
Figure 10:
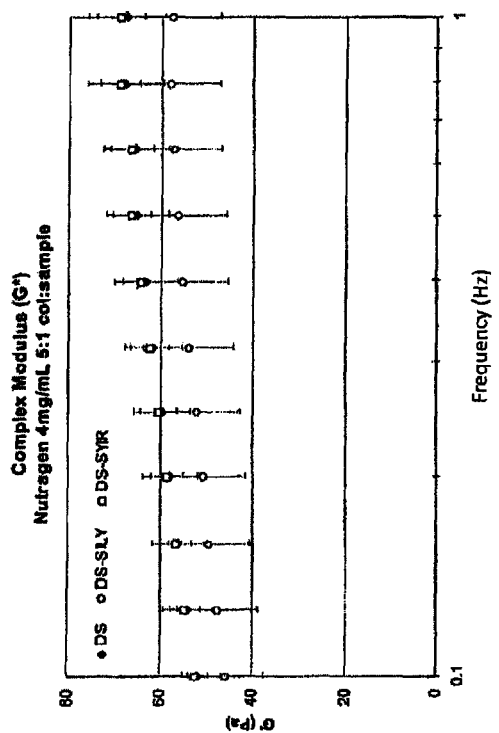
FIG. 10. Measurement of Shear modulus of gel samples (4 mg/mL collagen, 5:1 collagen:treatment) on a AR-G2 rheometer with 20 mm stainless steel parallel plate geometry (TA Instruments, New Castle, Del.), and the 20 mm stainless steel parallel plate geometry was lowered to a gap distance of 600 μm using a normal force control of 0.25N. Col, no treatment, i.e. collagen alone; Col+DS, collagen+dermatan sulfate; Col+decorin, collagen+decorin; Col+DS-SYIR, collagen+dermatan sulfate-SYIR; Col+DS-SILY, collagen+dermatan sulfate-SILY conjugate; Col+SILY, SILY peptide; Col+SYIR, collagen+SYIR peptide.
Figure 11:
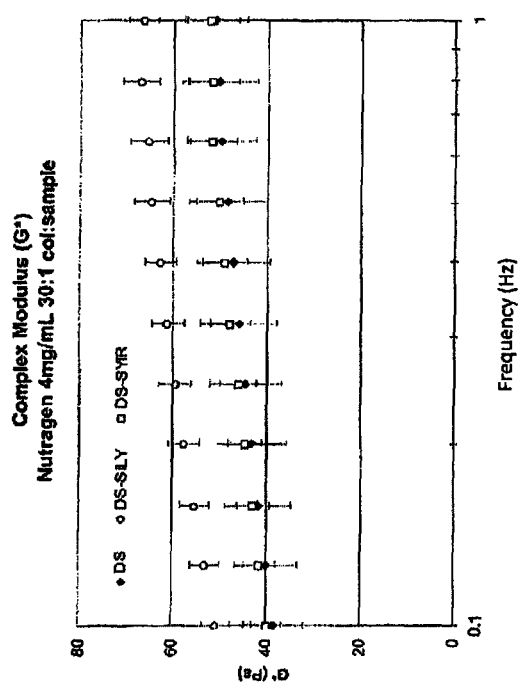
FIG. 11. Measurement of Shear modulus of gel samples (4 mg/mL collagen, 30:1 collagen:treatment) on a AR-G2 rheometer with 20 mm stainless steel parallel plate geometry (TA Instruments, New Castle, Del.), and the 20 mm stainless steel parallel plate geometry was lowered to a gap distance of 600 μm using a normal force control of 0.25N. Col, no treatment, i.e. collagen alone; Col+DS, collagen+dermatan sulfate; Col+decorin, collagen+decorin; Col+DS-SYIR, collagen+dermatan sulfate-SYIR conjugate; Col+DS-SILY, collagen+dermatan sulfate-SILY conjugate; Col+SILY, collagen+SILY peptide; Col+SYIR, collagen+SYIR peptide.

Slides were clamped on the rheometer stage of a AR-G2 rheometer with 20 mm stainless steel parallel plate geometry (TA Instruments, New Castle, Del.), and the 20 mm stainless steel parallel plate geometry was lowered to a gap distance of 600 µm using a normal force control of 0.25N to avoid excessive shearing on the formed gel. An iterative process of stress and frequency sweeps was performed on gels of collagen alone to determine the linear range. All samples were also tested over a frequency range from 0.1 Hz to 1.0 Hz and a controlled stress of 1.0 Pa. Statistical analysis using Design Expert software (StatEase, Minneapolis, Minn.) was performed at each frequency and a 5-way ANOVA used to compare samples. The results shown in FIG. 9, 10:1; FIG. 10, 5:1; and FIG. 11, 30:1 demonstrate that treatment with synthetic peptidoglycans can modify the viscoelastic behavior of collagen type I gels.

Example 18

Viscoelastic Characterization of Collagen III Containing Gels

Figure 12:
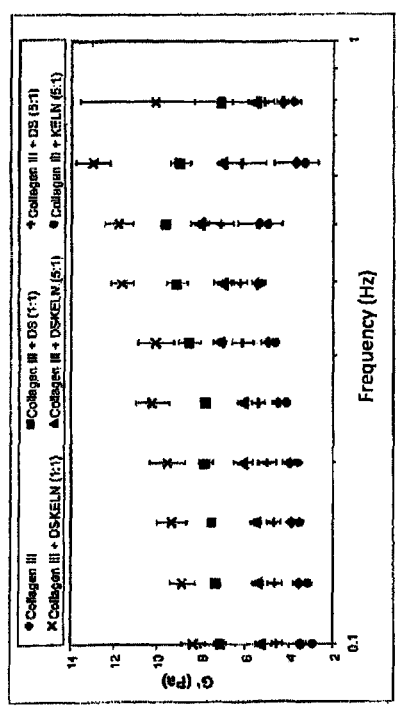
FIG. 12. Measurement of Shear modulus of gel samples (1.5 mg/mL collagen III, 5:1 collagen:treatment) on a AR-G2 rheometer with 20 mm stainless steel parallel plate geometry (TA Instruments, New Castle, Del.), and the 20 mm stainless steel parallel plate geometry was lowered to a gap distance of 500 μm using a normal force control of 0.25N. ♦–no treatment, i.e. collagen III alone; ■–collagen+dermatan sulfate (1:1); +–collagen+dermatan sulfate (5:1); x–collagen+dermatan sulfate-KELNLVYTGC [SEQ ID NO: 12] (DS-KELN) conjugate (1:1); ▲–collagen+dermatan sulfate-KELN conjugate (5:1); ●–collagen+KELNLVYTGC [SEQ ID NO: 12] (KELN) peptide.
Figure 13:
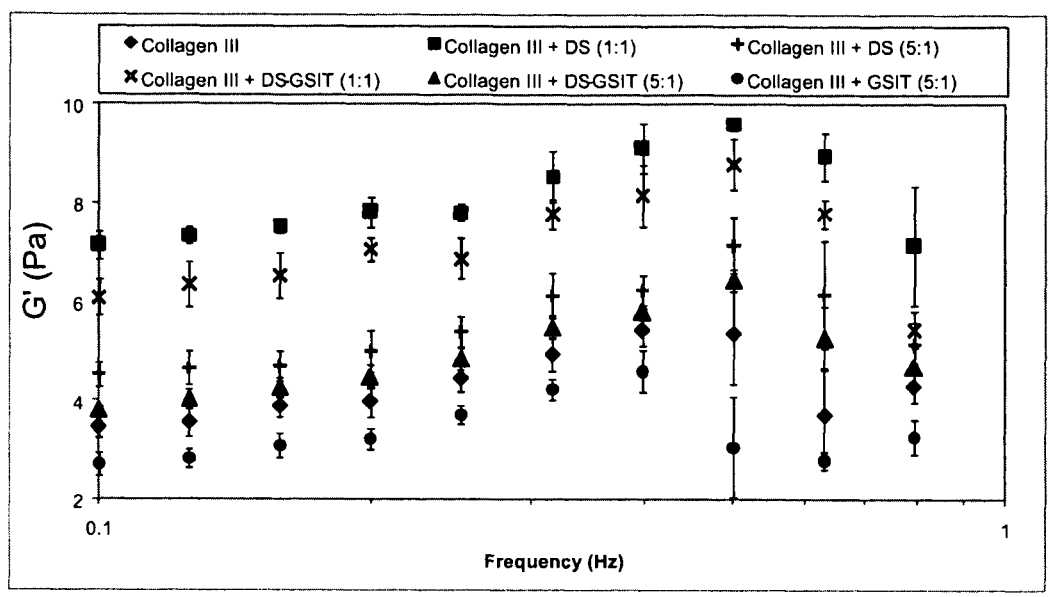
FIG. 13. Measurement of Shear modulus of gel samples (1.5 mg/mL collagen III, 5:1 collagen:treatment) on a AR-G2 rheometer with 20 mm stainless steel parallel plate geometry (TA Instruments, New Castle, Del.), and the 20 mm stainless steel parallel plate geometry was lowered to a gap distance of 500 μm using a normal force control of 0.25N. ♦–no treatment, i.e. collagen III alone; ■–collagen+dermatan sulfate (1:1); +–collagen+dermatan sulfate (5:1); x–collagen+dermatan sulfate-GSIT conjugate (DS-GSIT) (1:1); ▲–collagen+dermatan sulfate-GSIT conjugate (5:1); ●–collagen+GSITTIDVPWNVGC [SEQ ID NO: 14] (GSIT) peptide.

Gels containing type III collagen were prepared as in EXAMPLE 16 with the following modifications: treated and untreated gel solutions were prepared using a collagen concentration of 1.5 mg/mL (90% collagen III (Millipore), 10% collagen I), 200 µL samples were pipetted onto 20 mm diameter wettable surfaces of hydrophobic printed slides. These solutions were allowed to gel at 37° C. for 24 hours. Gels were formed from collagen alone, collagen treated with dermatan sulfate (1:1 and 5:1 molar ratio), and collagen treated with the collagen III-binding peptides alone (GSIT and KELN, 5:1 molar ratio) served as controls. The treated gels contained the peptidoglycans (DS-GSIT or DS-KELN at 1:1 and 5:1 molar ratios. All ratios are collagen:treatment compound ratios. The gels were characterized as in EXAMPLE 17, except the samples were tested over a frequency range from 0.1 Hz to 1.0 Hz at a controlled stress of 1.0 Pa. As shown in FIGS. 12 and 13, the dermatan sulfate-GSIT conjugate and the dermatan sulfate-KELN conjugate (synthetic peptidoglycans) can influence the viscoelastic properties of gels formed with collagen type III.

Example 19

Fibrillogenesis

Figure 14:
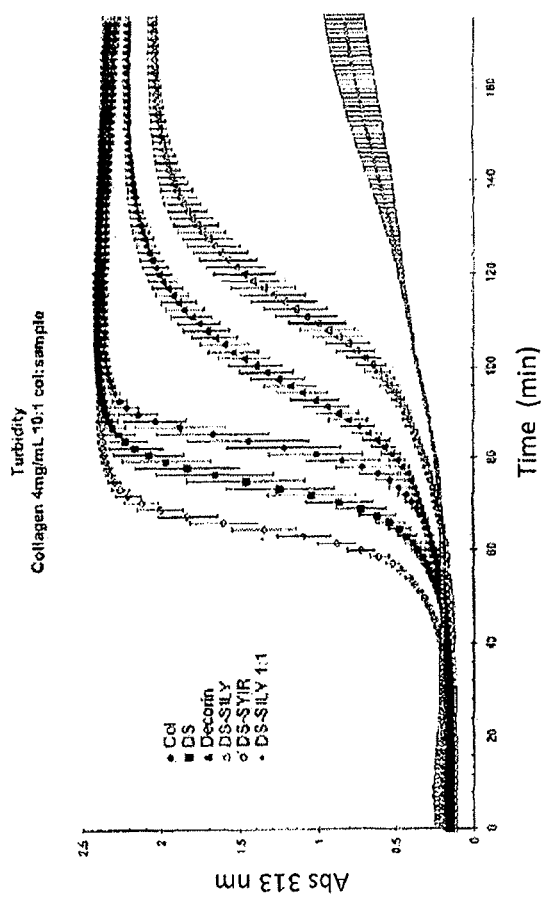
FIG. 14. Turbidity measurement. Gel solutions were prepared as described in EXAMPLE 16 (collagen 4 mg/mL and 10:1 collagen to treatment, unless otherwise indicated) and 50 μL/well were added at 4° C. to a 384-well plate. The plate was kept at 4° C. for 4 hours before initiating fibril formation. A SpectraMax M5 at 37° C. was used to measure absorbance at 313 nm at 30 s intervals for 6 hours. Col, no treatment, i.e., collagen alone; DS, collagen+dermatan sulfate; decorin, collagen+decorin; DS-SILY, collagen+dermatan sulfate-SILY conjugate; DS-SYIR, collagen+dermatan sulfate-SYIR conjugate.
Figure 15:
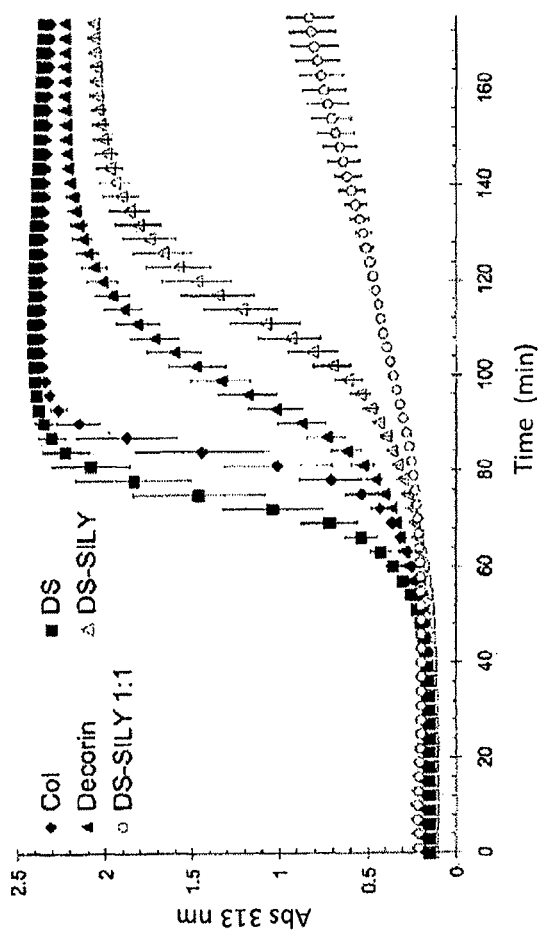
FIG. 15. Turbidity measurement. Gel solutions were prepared as described in EXAMPLE 16 (collagen 4 mg/mL and 10:1 collagen to treatment, unless otherwise indicated) and 50 μL/well were added at 4° C. to a 384-well plate. The plate was kept at 4° C. for 4 hours before initiating fibril formation. A SpectraMax M5 at 37° C. was used to measure absorbance at 313 nm at 30 s intervals for 6 hours. Col, no treatment, i.e., collagen alone; DS, collagen+dermatan sulfate; decorin, collagen+decorin; DS-SILY, collagen+dermatan sulfate-SILY conjugate.
Figure 16:
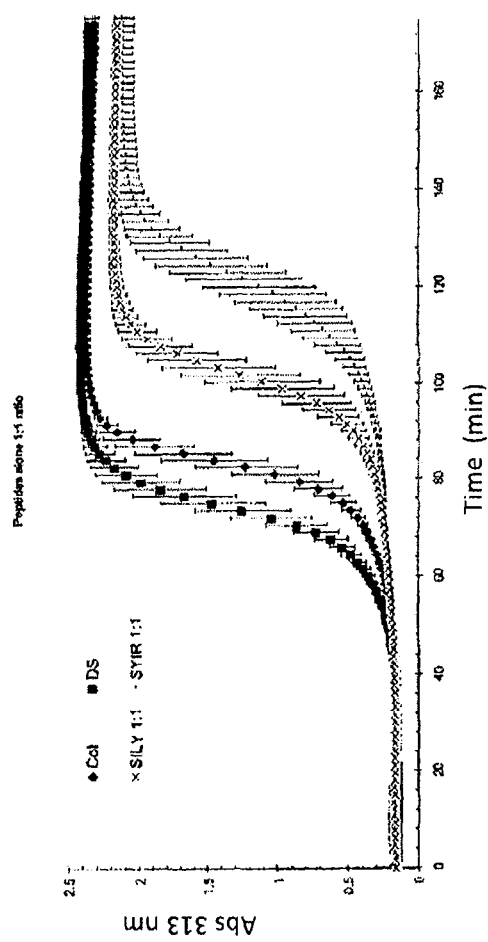
FIG. 16. Turbidity measurement. Gel solutions were prepared as described in EXAMPLE 16 (collagen 4 mg/mL and 1:1 collagen to treatment, unless otherwise indicated) and 50 μL/well were added at 4° C. to a 384-well plate. The plate was kept at 4° C. for 4 hours before initiating fibril formation. A SpectraMax M5 at 37° C. was used to measure absorbance at 313 nm at 30 s intervals for 6 hours. Col, no treatment, i.e., collagen alone; DS, collagen+dermatan sulfate 10:1; SILY, collagen+SILY peptide; SYIR, collagen+SYIR peptide.
Figure 17:
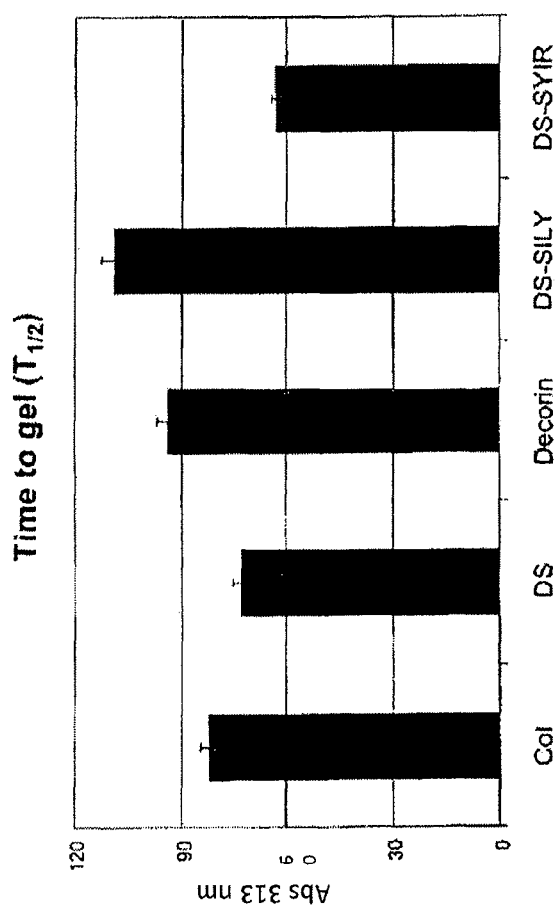
FIG. 17. Half-life of fibrillogenesis measured from the data presented in FIG. 14. Col, no treatment, i.e., collagen alone; DS, collagen+dermatan sulfate; decorin, collagen+decorin; DS-SILY, collagen+dermatan sulfate-SILY conjugate; DS-SYIR, collagen+dermatan sulfate-SYIR conjugate.

Collagen fibrillogenesis was monitored by measuring turbidity related absorbance at 313 nm providing information on rate of fibrillogenesis and fibril diameter. Gel solutions were prepared as described in EXAMPLE 16 (4 mg/mL collagen, 10:1 collagen:treatment, unless otherwise indicated) and 50 uL/well were added at 4° C. to a 384-well plate. The plate was kept at 4° C. for 4 hours before initiating fibril formation. A SpectraMax M5 at 37° C. was used to measure absorbance at 313 nm at 30 s intervals for 6 hours. The results are shown in FIGS. 14, 15, and 16. The $T_{1/2}$ for gel formation of the 10:1 molar ratio samples is shown in FIG. 17. Dermatan sulfate-SILY decreases the rate of fibrillogenesis.

Example 20

Confocal Reflection Microscopy

Figure 18:
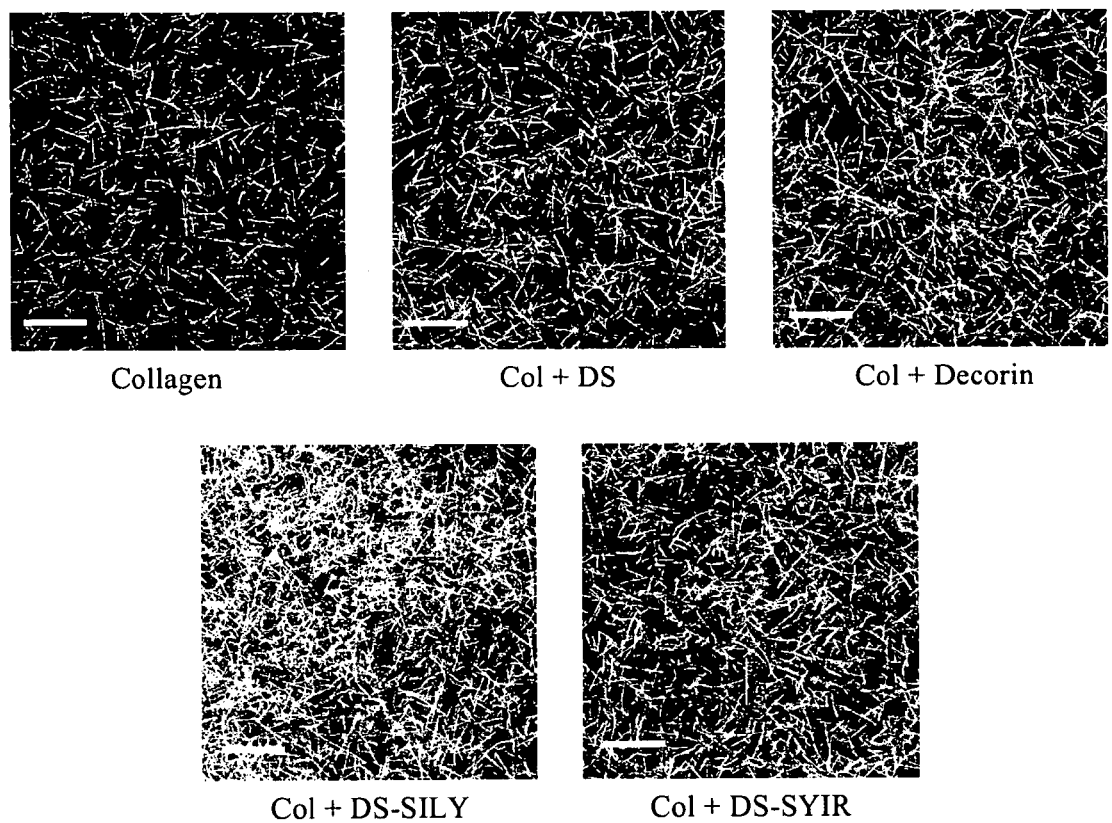
FIG. 18. Confocal Reflection Microscopy images of gels prepared according to EXAMPLE 16 (4 mg/mL collagen, 10:1 collagen:treatment) recorded with an Olympus FV1000 confocal microscope using a 60×, 1.4 NA water immersion lens. Samples were illuminated with 488 nm laser light and the reflected light was detected with a photomultiplier tube using a blue reflection filter. Each gel was imaged 100 μM from the bottom of the gel, and three separate locations were imaged to ensure representative sampling. Collagen, no treatment, i.e., collagen alone; Col+DS, collagen+dermatan sulfate; Col+Decorin, collagen+decorin; Col+DS-SILY, collagen+dermatan sulfate-SILY conjugate; Col+DS-SYIR, collagen+dermatan sulfate-SYIR conjugate.

Gels were formed and incubated overnight as described above in EXAMPLE 16, the gels were imaged with an Olympus FV1000 confocal microscope using a 60×, 1.4 NA water immersion lens. Samples were illuminated with 488 nm laser light and the reflected light was detected with a photomultiplier tube using a blue reflection filter. Each gel was imaged 100 μM from the bottom of the gel, and three separate locations were imaged to ensure representative sampling. Results are shown in FIG. 18.

Example 21

Cryo-SEM Measurements on Collagen I

Figure 19:
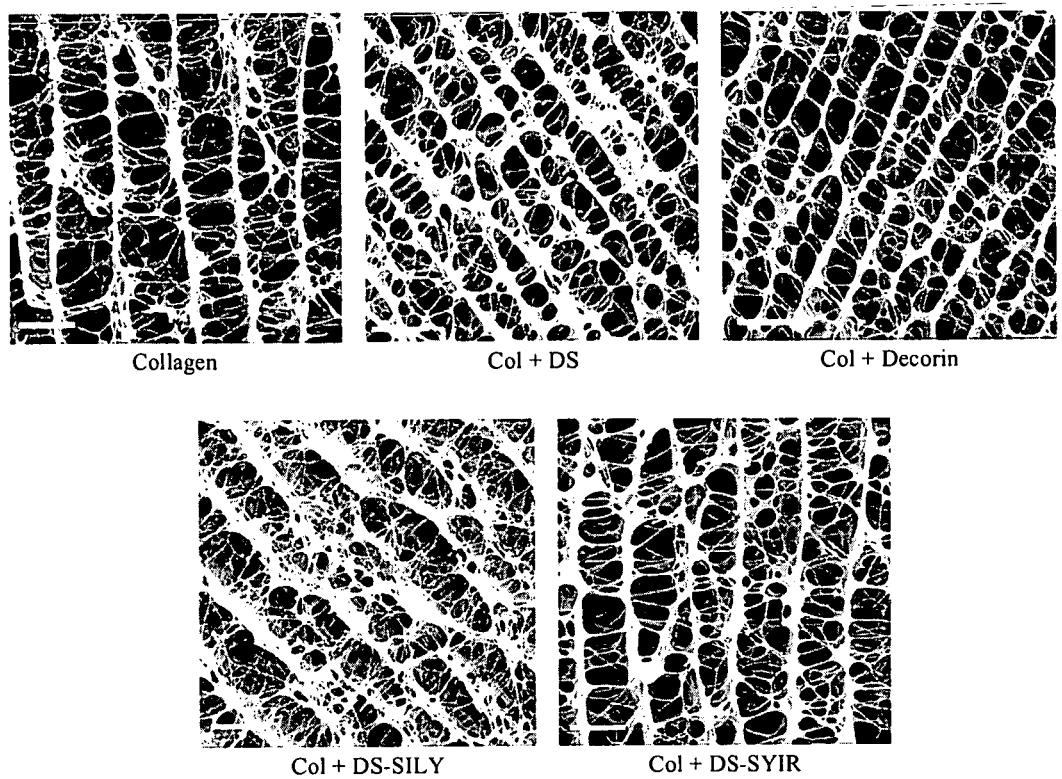
FIG. 19. Cryo-Scanning Electron Microscopy images of gel structure at a magnification of 5000. Gels for cryo-SEM were formed, as in EXAMPLE 16 (4 mg/mL collagen, 10:1 collagen:treatment), directly on the SEM stage and incubated at 37° C. overnight. Each sample evaporated under sublimation conditions for 20 min. The sample was coated by platinum sputter coating for 120 s. Samples were transferred to the cryo-stage at −130° C. and regions with similar orientation were imaged for comparison across treatments. Collagen, no treatment, i.e., collagen alone; Col+DS, collagen+dermatan sulfate; Col+Decorin, collagen+decorin; Col+DS-SILY, collagen+dermatan sulfate-SILY conjugate; Col+DS-SYIR, collagen+dermatan sulfate-SYIR conjugate.
Figure 22:
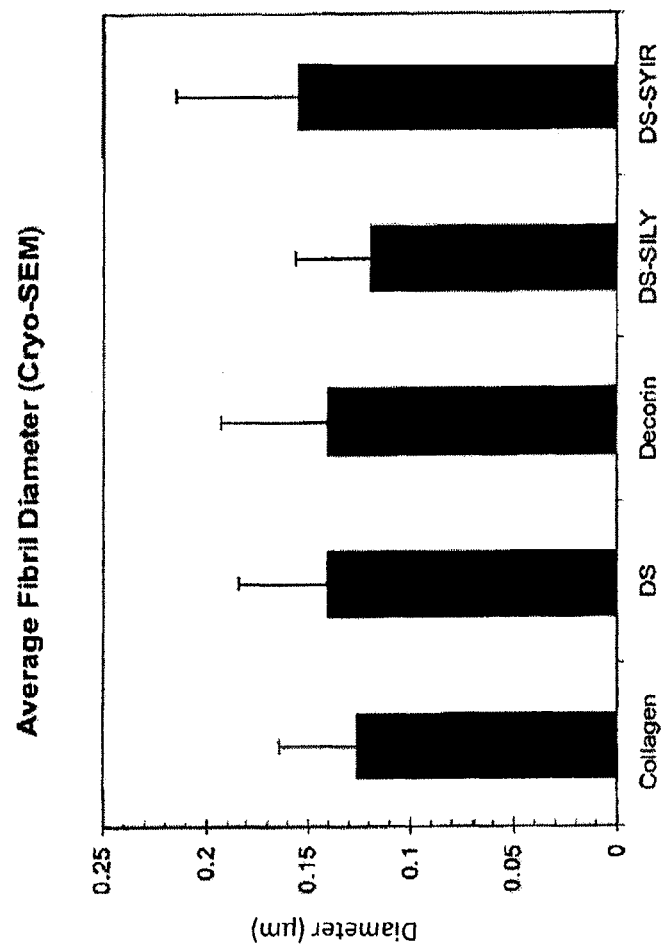
FIG. 22. The average fibril diameter measured from the Cryo-SEM images shown in FIG. 19. Collagen, no treatment, i.e., collagen alone; Col+DS, collagen+dermatan sulfate; Col+Decorin, collagen+decorin; Col+DS-SILY, collagen+dermatan sulfate-SILY conjugate; Col+DS-SYIR, collagen+dermatan sulfate-SYIR conjugate.
Figure 23:
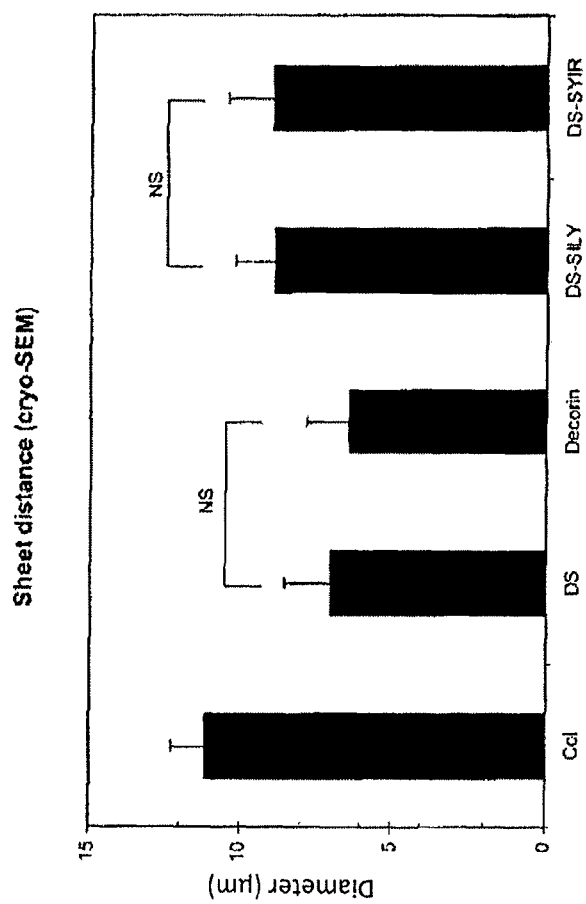
FIG. 23. The average distance between collagen sheets measured from the Cryo-SEM images shown in FIG. 19. Collagen, no treatment, i.e., collagen alone; Col+DS, collagen+dermatan sulfate; Col+Decorin, collagen+decorin; Col+DS-SILY, collagen+dermatan sulfate-SILY conjugate; Col+DS-SYIR, collagen+dermatan sulfate-SYIR conjugate.

Gels for cryo-SEM were formed, as in EXAMPLE 16, directly on the SEM stage and incubated at 37° C. overnight. The stages were then secured in a cryo-holder and plunged into liquid nitrogen slush. Samples were then transferred to a Gatan Alto 2500 pre-chamber cooled to −170° C. under vacuum. A free-break surface was created with a cooled scalpel, and each sample evaporated under sublimation conditions for 20 min. The sample was coated by platinum sputter coating for 120 s. Samples were transferred to the cryo-stage at −130° C. and regions with similar orientation were imaged for comparison across treatments. Representative samples imaged at 5,000× are shown in FIG. 19. Analysis of the images was performed to determine the average fibril diameter, FIG. 22; and the average distance between collagen sheets, FIG. 23. Fibril diameter was calculated using ImageJ software (NIH) measuring individual fibrils by hand (drawing a line across fibrils and measuring its length after properly setting the scale). There were 3 observers, 3 separate images per treatment, 10 fibrils recorded per image giving a total of 90 measurements per treatment. Sheet distance was calculated using ImageJ, again measuring by hand. One observer and 15 measurements per treatment. Fibril diameter and distance between collagen sheets decreased in the gels treated with the dermatan sulfate-SILY synthetic peptidoglycan.

Example 22

Cryo-SEM Measurements on Collagen III

Figure 20:
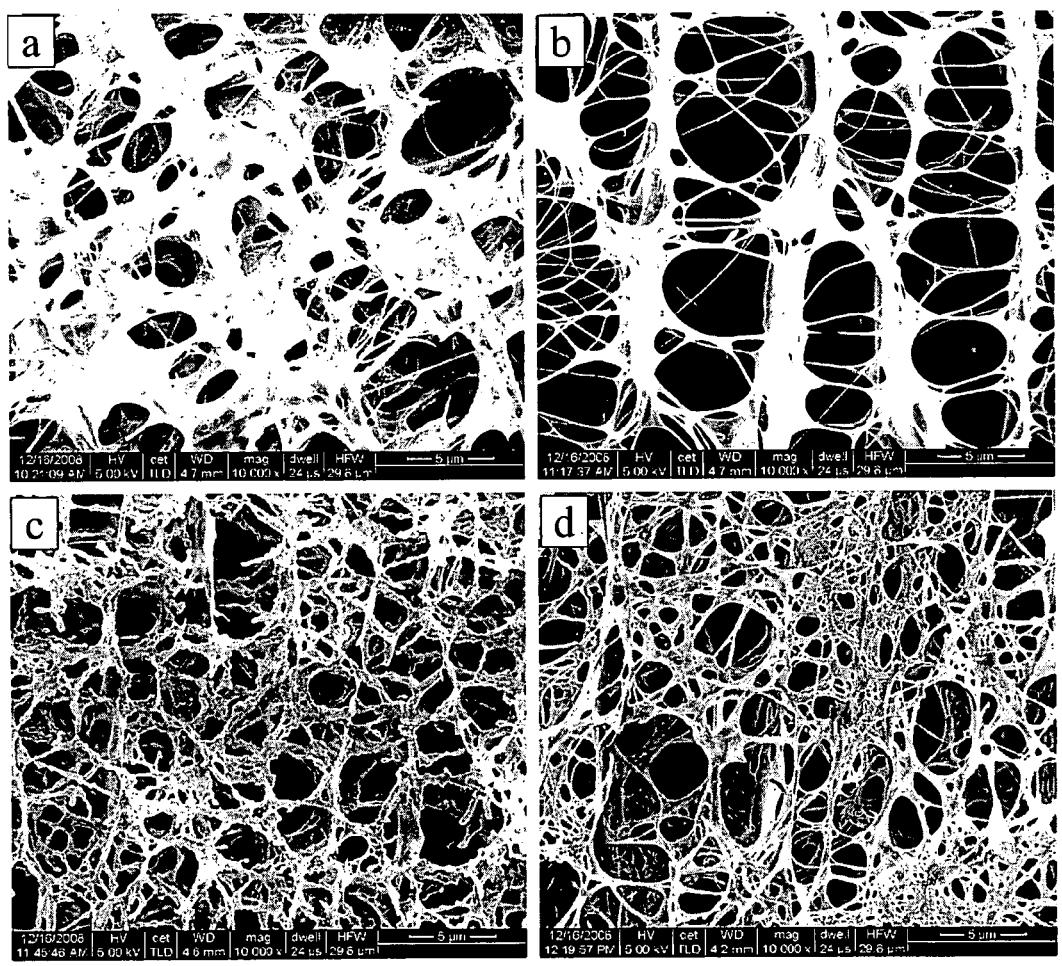
FIG. 20. Cryo-Scanning Electron Microscopy images of gel structure at a magnification of 5000. Gels for cryo-SEM were formed, as described in EXAMPLE 22 (1 mg/mL collagen (Type III), 1:1 collagen:treatment), directly on the SEM stage. Regions with similar orientation were imaged for comparison across treatments. Panel a, Collagen, no treatment, i.e., collagen alone; Panel b, collagen+dermatan sulfate; Panel c, collagen+dermatan sulfate-KELN conjugate; Panel d, collagen+dermatan sulfate-GSIT conjugate.
Figure 21:
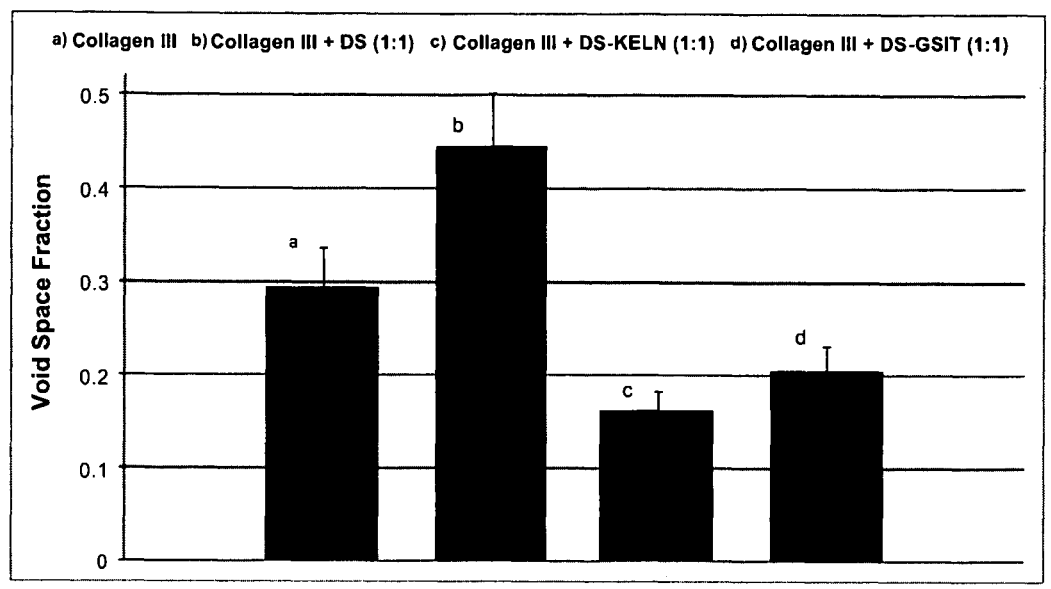
FIG. 21. The average void space fraction measured from the Cryo-SEM images shown in FIG. 20. a) Collagen, no treatment, i.e., collagen alone; b) collagen+dermatan sulfate; c) collagen+dermatan sulfate-KELN conjugate; d) collagen+dermatan sulfate-GSIT conjugate. All differences are significant with p=0.05.

Gels for cryo-SEM were formed, as in EXAMPLE 16, directly on the SEM stage and incubated at 37° C. overnight with the following modifications. The collagen concentration was 1 mg/mL (90% collagen III, 10% collagen I). The collagen:DS ratio was 1:1 and the collagen:peptidoglycan ratio was 1:1. The images were recorded as in EXAMPLE 21. The ratio of void volume to fibril volume was measured using a variation of the method in EXAMPLE 21. The results are shown in FIGS. 20 and 21. Dermatan sulfate-KELN and dermatan sulfate-GSIT decrease void space (increase fibril diameter and branching) in the treated collagen gels.

Example 23

AFM Confirmation of D-Banding

Figure 2:
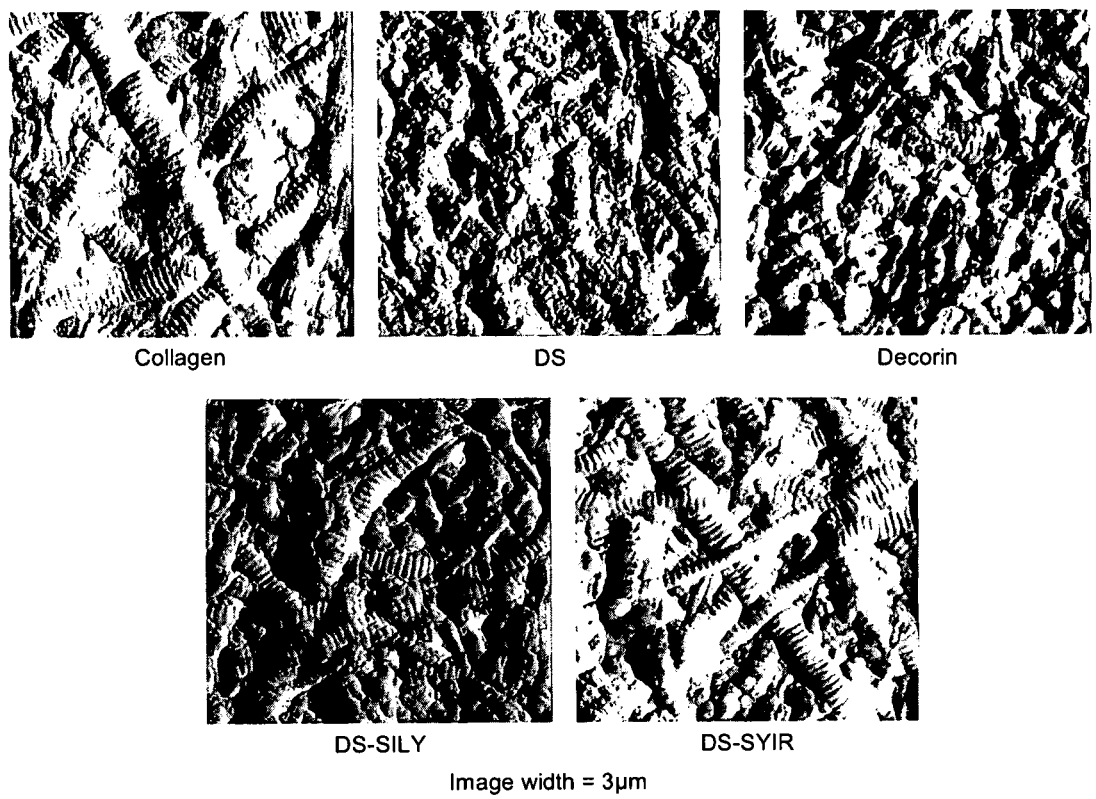
FIG. 2. AFM images made in contact mode, with a scan rate of 2 Hz with Silicon Nitride contact mode tip k=0.05N/m tips and deflection setpoint: 0-1 Volts, of gel samples prepared as in EXAMPLE 16 (10:1 collagen:treatment) after dehydration with ethanol. Samples are for collagen alone (Collagen), and for collagen with dermatan sulfate (DS), with decorin (Decorin), dermatan sulfate-RRANAALKAGELYKSI-LYGC [SEQ ID NO: 1] conjugate (DS-SILY) and dermatan sulfate-SYIRIADTNIT [SEQ ID NO: 10] conjugate (DS-SYIR).
Figure 38:
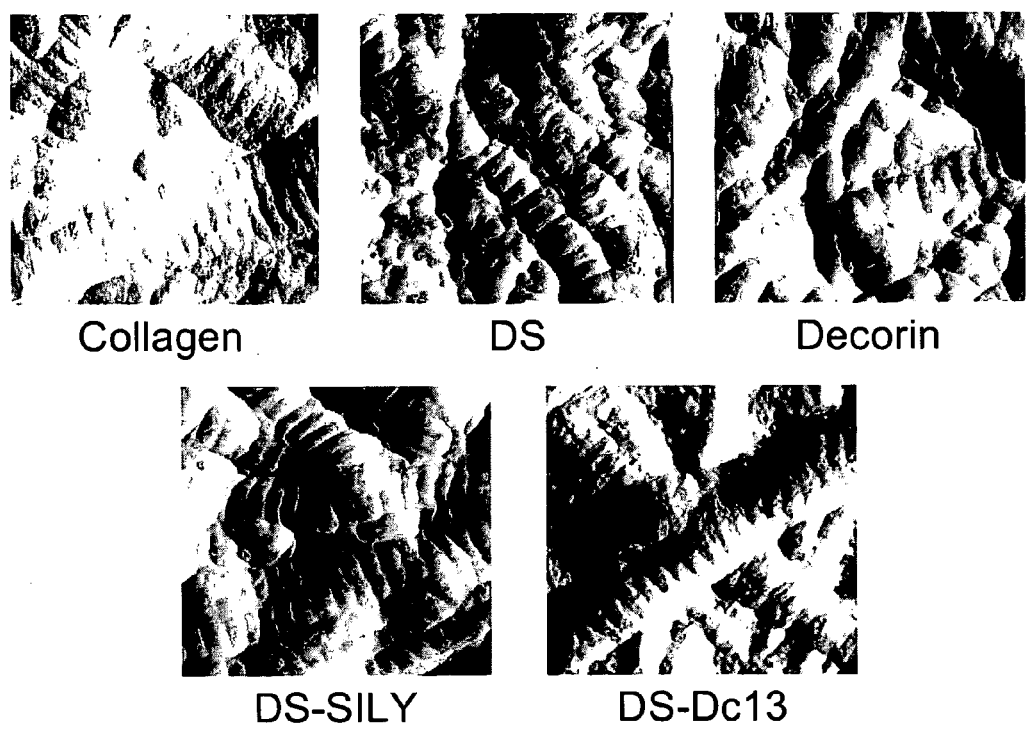
FIG. 38. AFM Images of Collagen Gels. Collagen gels were formed in the presence of each additive at a 10:1 molar ratio of collagen:additive. D-banding is observed for all additives. Images are 1 µm².

Gel solutions were prepared as described in EXAMPLE 16 and 20 μL of each sample were pipetted onto a glass coverslip and allowed to gel overnight in a humidified incubator. Gels were dehydrated by treatment with graded ethanol solutions (35%, 70%, 85%, 95%, 100%), 10 min in each solution. AFM images were made in contact mode, with a scan rate of 2 Hz (Multimode SPM, Veeco Instruments, Santa Barbara, Calif., USA, AFM tips Silicon Nitride contact mode tip k=0.05N/m, Veeco Instruments) Deflection setpoint: 0-1 Volts. D-banding was confirmed in all treatments as shown in FIGS. 2 and 38.

Example 24

Collagen Remodeling

Tissue Sample Preparation

Figure 53:
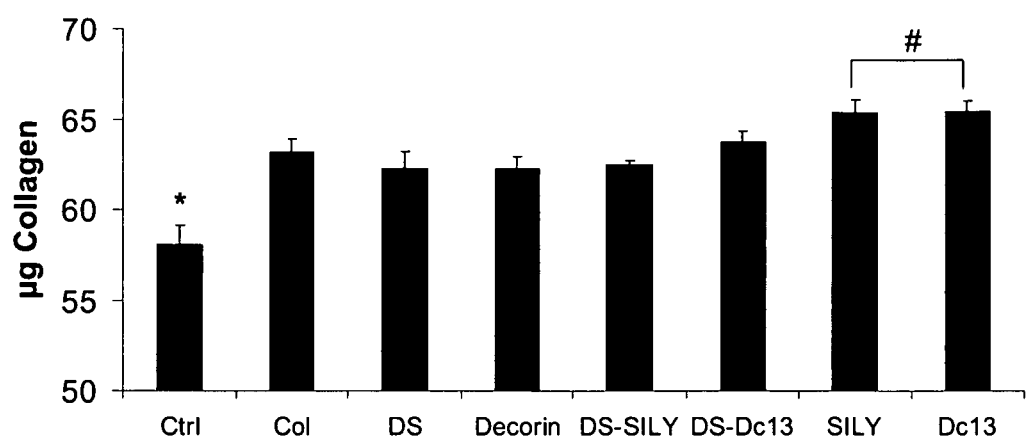
FIG. 53. Collagen Degradation Determined by Hydroxyproline. Treatments: Ctrl, no cells added; Col, collagen without added treatment; DS, dermatan sulfate; Decorin; DS-SILY, dermatan sulfate-SILY conjugate; DS-Dc13, dermatan sulfate-Dc13 conjugate; SILY, SILY peptide; Dc13, Dc13 peptide.

Following a method by Grassi, et al. (Grassi, et al., *Journal of Biomedical Materials Research* 2002, 60, (4), 607-612), which is herein incorporated in its entirety, collagen gels with or without synthetic PG mimics were formed as described in EXAMPLE 16. Human aortic smooth muscle cells (Cascade Biologics, Portland, Oreg.) were seeded within collagen gels by adding $4 \times 10^6$ cells/mL to the neutralized collagen solution prior to incubation. The cell-collagen solutions were pipetted into an 8-well Lab-Tek chamber slide and incubated in a humidified 37° C. and 5% $CO_2$ incubator. After gelation, the cell-collagen gels will be covered with 1 mL Medium 231 as prescribed by Cascade. Every 3-4 days, the medium was removed from the samples and the hydroxyproline content measured by a standard hydroxyproline assay (Reddy, 1996).
Hydroxyproline Content To measure degraded collagen in the supernatant medium, the sample was lyophilized, the sample hydrolyzed in 2M NaOH at 120° C. for 20 min After cooling, free hydroxyproline was oxidized by adding chloramine-T (Sigma) and reacting for 25 min at room temperature. Ehrlich's aldehyde reagent (Sigma) was added and allowed to react for 20 min at 65° C. and followed by reading the absorbance at 550 nm on an M-5 spectrophotometer (Molecular Devices). Hydroxyproline content in the medium is an indirect measure degraded collagen and tissue remodeling potential. Cultures were incubated for up to 30 days and three samples of each treatment measured. A gels incubated without added cells were used as a control. Free peptides SILY and Dc13 resulted in greater collagen degradation compared to collagen alone as measured by hydroxyproline content in cell medium as shown in FIG. 53.

Cell Viability

Cell viability was determined using a live/dead violet viability/vitality kit (Molecular Probes. The kit contains calcein-violet stain (live cells) and aqua-fluorescent reactive dye (dead cells). Samples were washed with 1×PBS and incubated with 300 μL of dye solution for 1 hr at room temperature. To remove unbound dye, samples were rinsed with 1×PBS. Live and dead cells were counted after imaging a 2-D slice with filters 400/452 and 367/526 on an Olympus FV1000 confocal microscope with a 20× objective. Gels were scanned for representative regions and 3 image sets were taken at equal distances into the gel for all samples.

Example 25

Cell Proliferation in Gels

Figure 25:
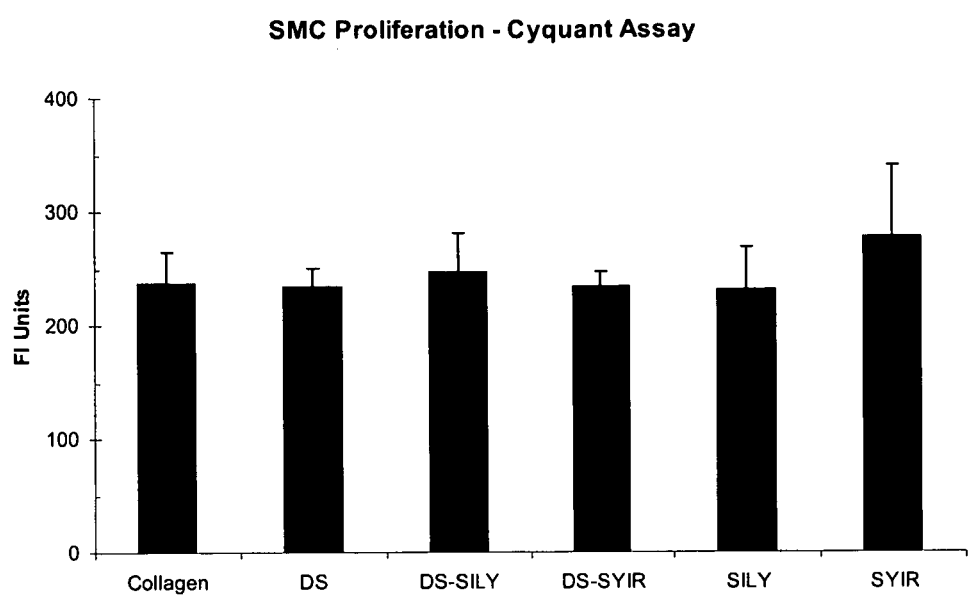
FIG. 25. Measuring Human Coronary Artery Smooth Muscle Cell Proliferation in Collagen Gels Prepared with Collagen-binding synthetic peptidoglycans. Collagen, no treatment, i.e., collagen alone; DS, collagen+dermatan sulfate; DS-SILY, collagen+dermatan sulfate-SILY conjugate; DS-SYIR, collagen+dermatan sulfate-SYIR conjugate; SILY, collagen+SILY peptide; and SYIR, collagen+SYIR peptide.

Gel samples were prepared as in EXAMPLE 16 (4 mg/mL collagen, 10:1 collagen:treatment) Cells were seeded at 1.5× $10_4$ cells/cm$^2$ and were incubated in growth medium for 4 hrs to adhere the cells to the gel. The growth medium was then aspirated and the cells were treated for 24 hrs. Treatment concentrations were equal to those in gels at 10:1 molar ratio collagen: treatment. The cells were incubated in growth medium for 4 hrs to adhere to the gel. The growth medium was removed by aspiration and replaced with fresh growth medium. The samples were incubated for 24 h. The number of cells in each sample was measured using the CyQuant Cell Proliferation Assay (Invitrogen, Carlsbad, Calif., USA). The results shown in FIG. 25 indicate that the synthetic peptidoglycans and peptides do not adversely affect cell proliferation.

Example 26

Preparation of DS-Dc13

Figure 27:
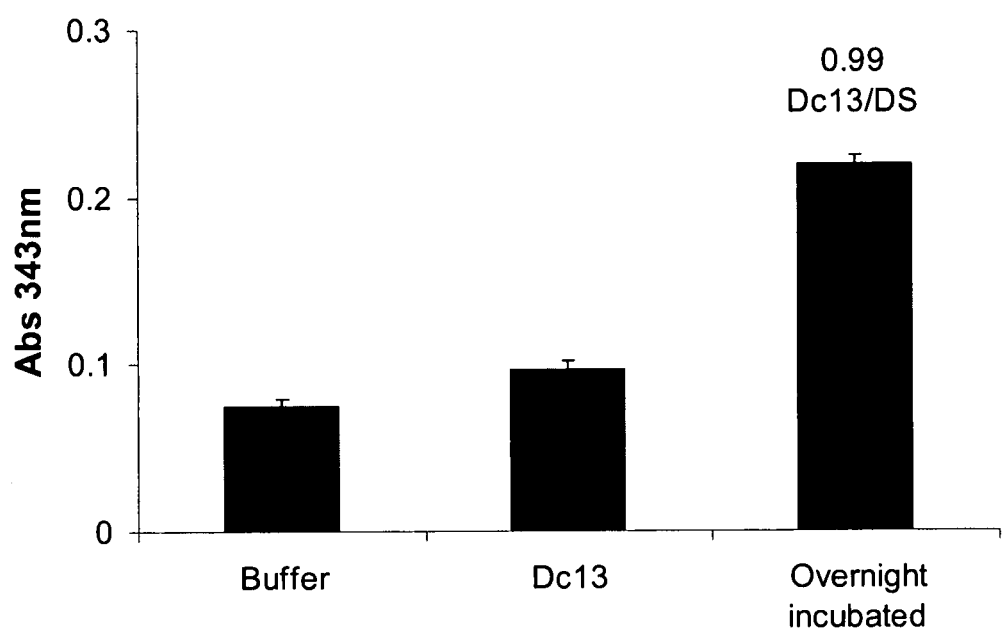
FIG. 27. Conjugation of Dc13 to DS. Production of pyridine-2-thione measured by an increase in absorbance at 343 nm indicates 0.99 Dc13 peptides per DS polymer chain.

The Dc 13 peptide sequence is SYIRIADTNITGC and its fluorescently labeled form is ZSYIRIADTNITGC, where Z designates dansylglycine. Conjugation to dermatan sulfate using the heterobifunctional crosslinker PDPH is performed as described for DS-SILY in EXAMPLE 3. As shown in FIG. 27, the molar ratio of Dc13 to dermatan sulfate in the conjugate (DS-Dc13) was about 1.

Example 27

Fluorescence Binding Assay for DS-ZSILY

Figure 28:
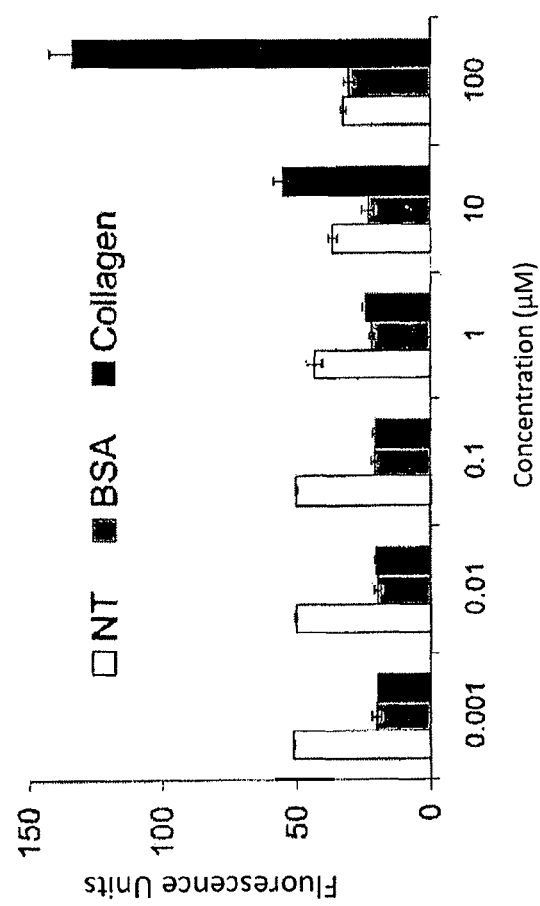
FIG. 28. Microplate Fluorescence Binding of DS-ZDc13 to Collagen. DS-ZDc13 bound specifically to the collagen surface in a dose-dependent manner.

The fluorescence binding assays described for DS-ZSILY was performed with peptide sequence ZSYIRIADTNITGC (ZDc13). The results appear in FIG. 28, showing that DS-ZDc13 binds specifically to the collagen surface in a dose-dependent manner, though saturation was not achieved at the highest rate tested.

Example 28

Fibrillogenesis Assay for DS-Dc13

Figure 29:
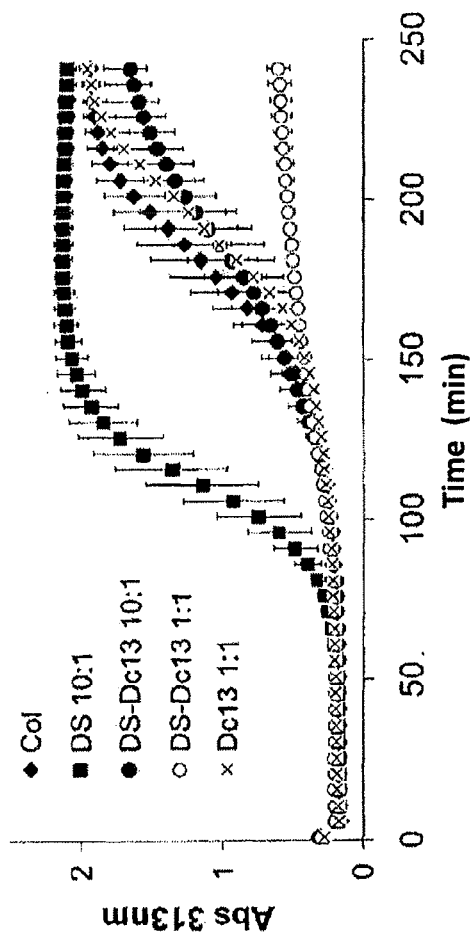
FIG. 29. Collagen Fibrillogenesis by Turbidity Measurements. DS-Dc13 delays fibrillogenesis and decreases overall absorbance in a dose-dependent manner. Free Dc13 peptide, in contrast, appears to have little effect on fibrillogenesis compared to collagen alone at the high 1:1 collagen:additive molar ratio.

A fibrillogenesis assay as described for DS-SILY, EXAMPLE 19, performed with the conjugate DS-Dc13. The results shown in FIG. 29 indicate that the DS-Dc13 delays fibrillogenesis and decreases overall absorbance in a dose-dependent manner. Free Dc13 peptide in contrast has little effect on fibrillogenesis compared to collagen alone at the high 1:1 collagen:additive molar ratio.

Example 29

Use of Cryo-SEM to Measure Fibril Diameters

Figure 30:
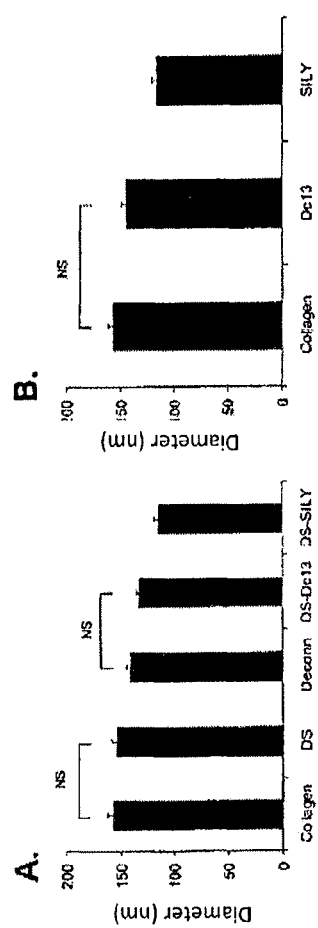
FIG. 30. Average Fibril Diameter from Cryo-SEM. A. Decorin and synthetic peptidoglycans significantly decrease fibril diameter over collagen or collagen+DS. B. Compared to collagen alone, free peptide Dc13 does not affect fibril diameter while SILY results in a decrease in fibril diameter.

Using a modification of EXAMPLE 21 fibril diameters were measured by cryo-SEM. Fibril diameters from cryo-SEM images taken at 20,000× were measured using ImageJ software (NIH). At least 45 fibrils were measured for each treatment. Results are presented as Avg.±S.E. Statistical analysis was performed using DesignExpert software (StatEase) with α=0.05. The results are shown in FIG. 30. Decorin and synthetic peptidoglycans significantly decrease fibril diameter over collagen or collagen+dermatan sulfate. Compared to collagen alone, free peptide Dc13 does not affect fibril diameter while free SILY results in a decrease in fibril diameter.

Example 30

Cell Culture and Gel Compaction

Human coronary artery smooth muscle cells (HCA SMC) (Cascade Biologics) were cultured in growth medium (Medium 231 supplemented with smooth muscle growth factor). Cells from passage 3 were used for all experiments. Differentiation medium (Medium 231 supplemented with 1% FBS and 1× pen/strep) was used for all experiments unless otherwise noted. This medium differs from manufacturer protocol in that it does not contain heparin.

Figure 31:
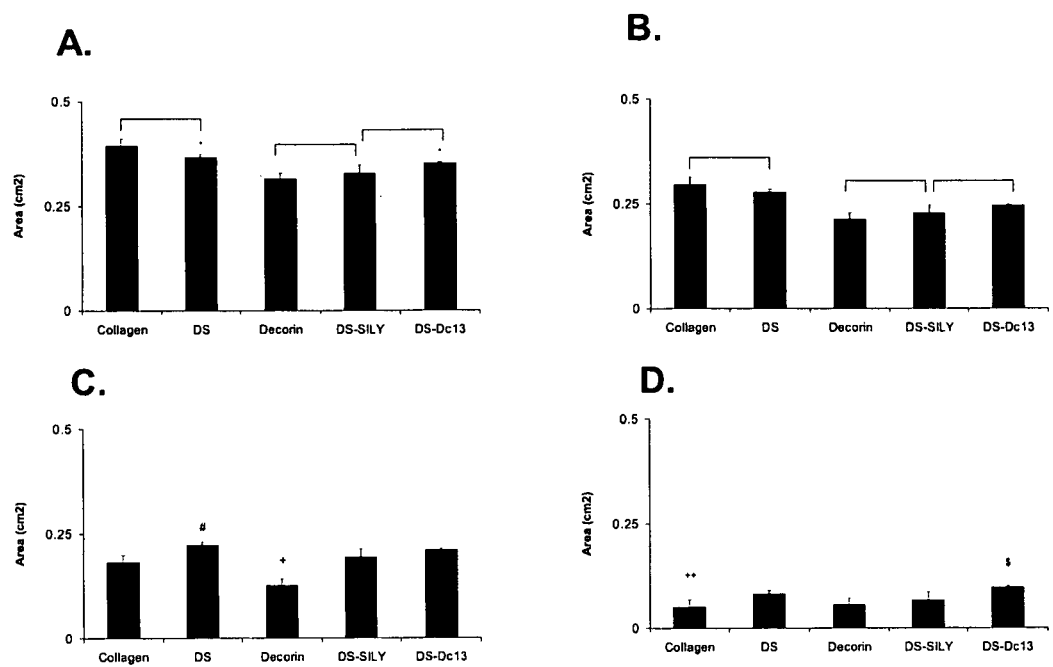
FIG. 31. Gel Compaction. A. and B. Days 3 and 5 respectively: Decorin and peptidoglycans are significant relative to collagen and DS, *indicates DS-Dc13 and DS are not significant at day 3. Bars indicate no significance. C. Day 7: +Decorin is significant against all samples, #DS is significant compared to collagen. D. Day 10: ++collagen and DS are significant, *DS-Dc13 is significant compared to decorin and collagen.

Collagen gels were prepared with each additive as described with the exception that the 1×PBS example addition was omitted to accommodate the addition of cells in media. After incubating on ice for 30 min, HCA SMCs in differentiation medium were added to the gel solutions to a final concentration of 1×10$^6$ cells/mL. Gels were formed in quadruplicate in 48-well non-tissue culture treated plates (Costar) for 6 hrs before adding 500 μL/well differentiation medium. Gels were freed from the well edges after 24 hrs. Medium was changed every 2-3 days and images for compaction were taken at the same time points using a Gel Doc System (Bio-Rad). The cross-sectional area of circular gels correlating to degree of compaction was determined using ImageJ software (NIH). Gels containing no cells were used as a negative control and cells in collagen gels absent additive were used as a positive control. The results are shown in FIG. 31. By day 10 all gels had compacted to approximately 10% of the original gel area, and differences between additives were small. Gels treated with DS-Dc13 were slightly, but significantly, less compact than gels treated with decorin or collagen but compaction was statistically equivalent to that seen with DS and DS-SILY treated gels.

Example 31

Measurement of Elastin

Figure 32:
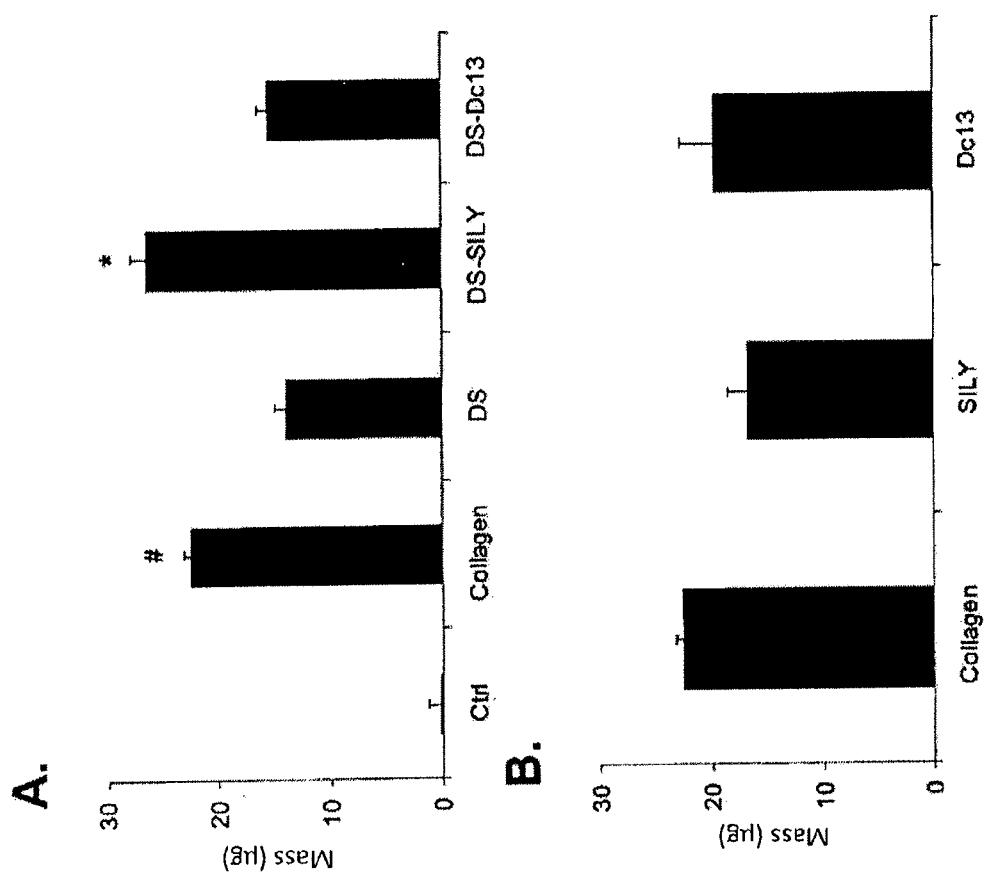
FIG. 32. Elastin Estimate by Fastin Assay. A. DS-SILY significantly increased elastin production over all samples. DS and DS-Dc13 significantly decreased elastin production over collagen. Control samples of collagen gels with no cells showed no elastin production. B. Free peptides resulted in a slight decrease in elastin production compared to collagen, but no points were significant.

Collagen gels seeded with HCA SMCs were prepared as described in EXAMPLE 30. Differentiation medium was changed every three days and gels were cultured for 10 days. Collagen gels containing no cells were used as a control. Gels were rinsed in 1×PBS overnight to remove serum protein, and gels were tested for elastin content using the Fastin elastin assay per manufacturers protocol (Biocolor, County Atrim, U.K.). Briefly, gels were solubilized in 0.25 M oxalic acid by incubating at 100° C. for 1 hr. Elastin was precipitated and samples were then centrifuged at 11,000×g for 10 mM The solubilized collagen supernatant was removed and the elastin pellet was stained by Fastin Dye Reagent for 90 mM at room temperature. Samples were centrifuged at 11,000×g for 10 min and unbound dye in the supernatant was removed. Dye from the elastin pellets was released by the Fastin Dye Dissociation Reagent, and 100 µL samples were transferred to a 96-well plate (Costar). Absorbance was measured at 513 nm, and elastin content was calculated from an α-elastin standard curve. The results of these assays are shown in FIG. 32. Treatment with DS-SILY significantly increased elastin production over all samples. Treatment with DS and DS-Dc13 significantly decreased elastin production over untreated collagen. Control samples of collagen gels with no cells showed no elastin production.

Example 32

Effect of Heparin or Heparin-SILY on Platelet Interaction

Collagen was immobilized on glass cover slides (18 mm) by incubating slides with collagen at 2 mg/mL in 10 mM HCl for 1 hr at 37° C. Slides were then washed with 1×PBS and stored at 4° C. in 1×PBS for 24 hrs until further testing. Untreated glass cover slides were used as a negative control. Slides were placed into a 48-well non tissue-culture treated plate (Costar) with the collagen surface facing up. Heparin or Heparin-SILY were dissolved in 1×PBS to a concentration of 100 µM and incubated at 100 µL/well for 30 mM at 37° C. Unbound heparin or Heparin-SILY were aspirated and the surfaces were washed with 1 mL 1×PBS. Collagen immobilized slides incubated with 1×PBS containing no additive were used as a positive control.

Figure 33:
FIG. 33. SEM Images of Platelet-Rich Plasma Incubated Slides. Arrows in Heparin-SILY treatment indicate fibril-like structures unique to this treatment. Scale bar=100 µm.
Figure 33:
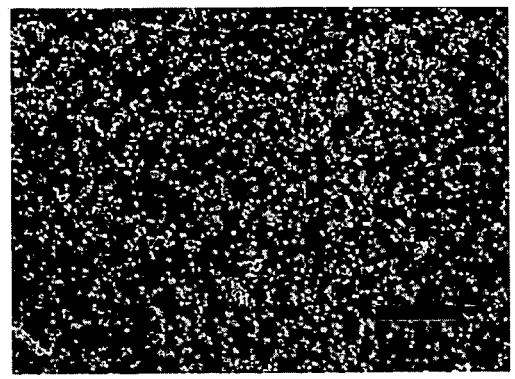
Figure 33:
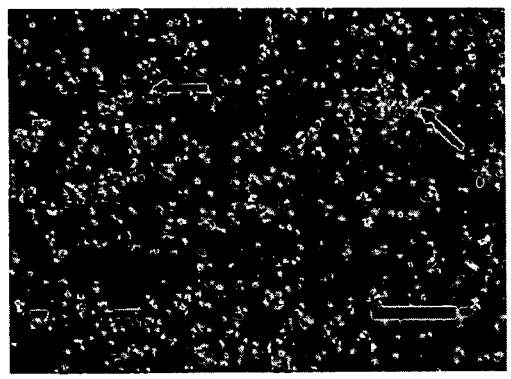
Figure 33:
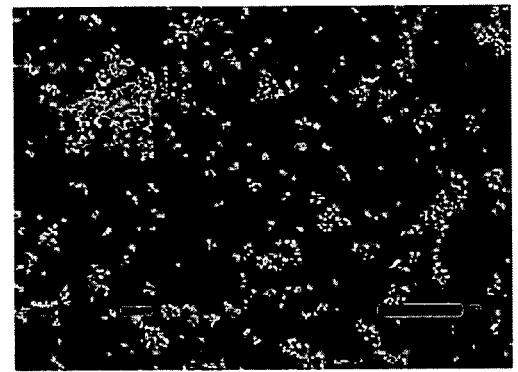

Whole human blood was centrifuged at 800×g for 15 min and 100 µL of platelet-rich plasma was removed from the buffy coat layer and added to each well. After incubating for 1 hr at 37° C., platelet-rich plasma was removed from the wells and the wells were gently washed with 1×PBS to remove unbound cells. Slides were fixed with 5% glutaraldehyde for 1 hr at room temperature, rinsed, and lyophilized before imaging. Slides were gold sputter coated for 3 min and imaged at 200× on a JEOL 840 SEM. The results are shown in FIG. 33. This images show that treatment with the heparin-SILY conjugate affects platelet cell binding to collagen.

Example 33

Cryo-SEM Measurement of Fibril Density

Figure 34:
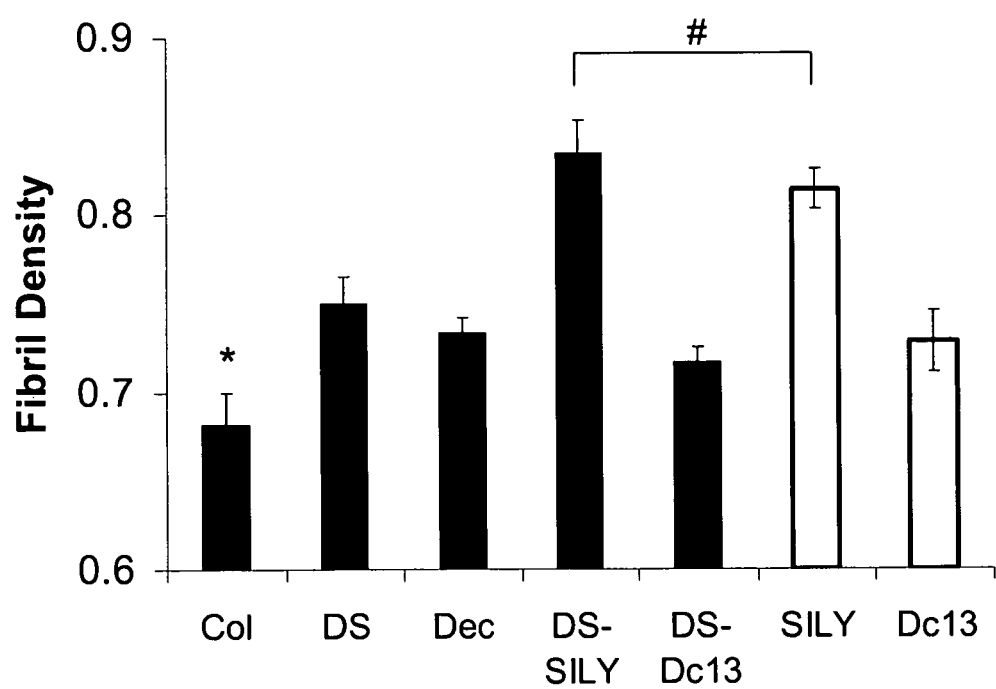
FIG. 34. Fibril Density from Cryo-SEM. Fibril density, defined as the ratio of fibril containing area to void space. DS-SILY and free SILY peptide had significantly greater fibril density, while collagen had significantly lower fibril density. DS-Dc13 was not significant compared to collagen.
Figure 37:
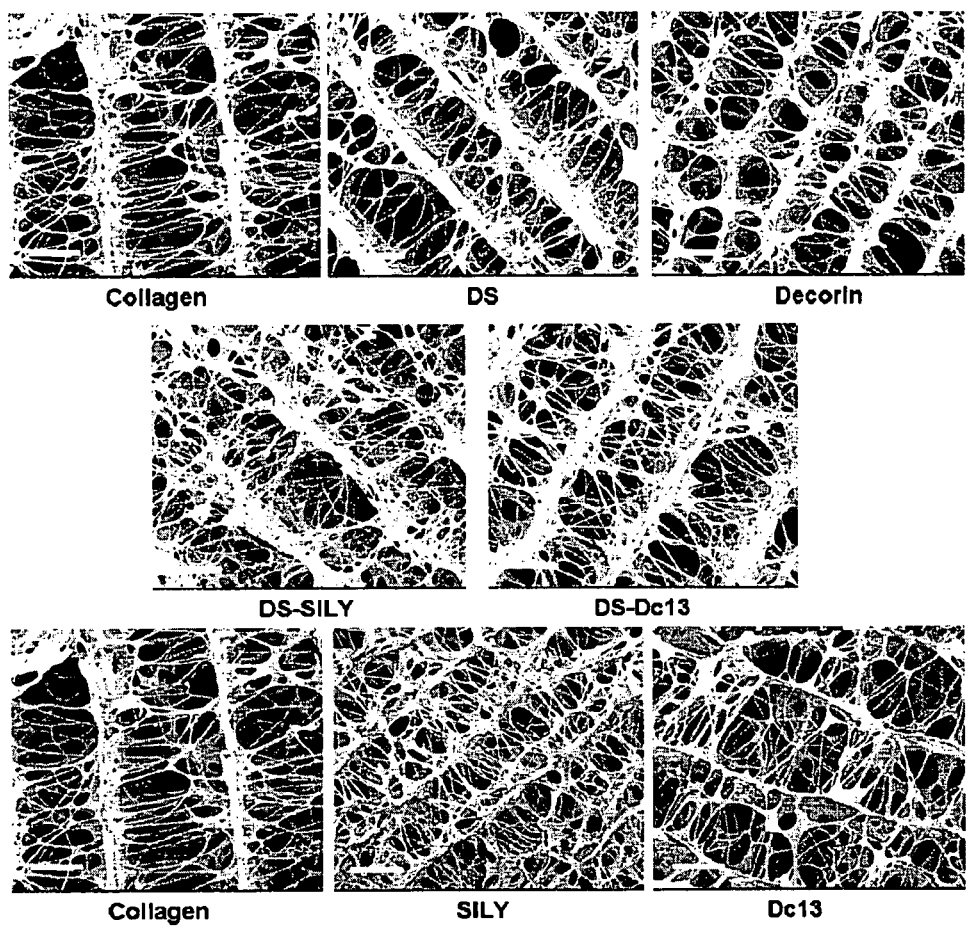
FIG. 37. Cryo-SEM Images for Fibril Density. Collagen gels formed in the presence of each additive at a 10:1 molar ratio of collagen:additive. A. DS, Decorin, or peptidoglycans. B. Free Peptides. Images are taken at 10,000×, Scale bar=5 µm.

Collagen gels were formed in the presence of each additive at a 10:1 molar ratio, as described in EXAMPLE 16, directly on the SEM stage, processed, and imaged as described. Images at 10,000× were analyzed for fibril density calculations. Images were converted to 8-bit black and white, and threshold values for each image were determined using ImageJ software (NIH). The threshold was defined as the value where all visible fibrils are white, and all void space is black. The ratio of white to black area was calculated using MatLab software. All measurements were taken in triplicate and thresholds were determined by an observer blinded to the treatment. Images of the gels are shown in FIG. 37 and the measured densities are shown in FIG. 34.

Example 34

Viscoelastic Characterization of Gels containing Dc13 or DS-Dc13

Figure 35:
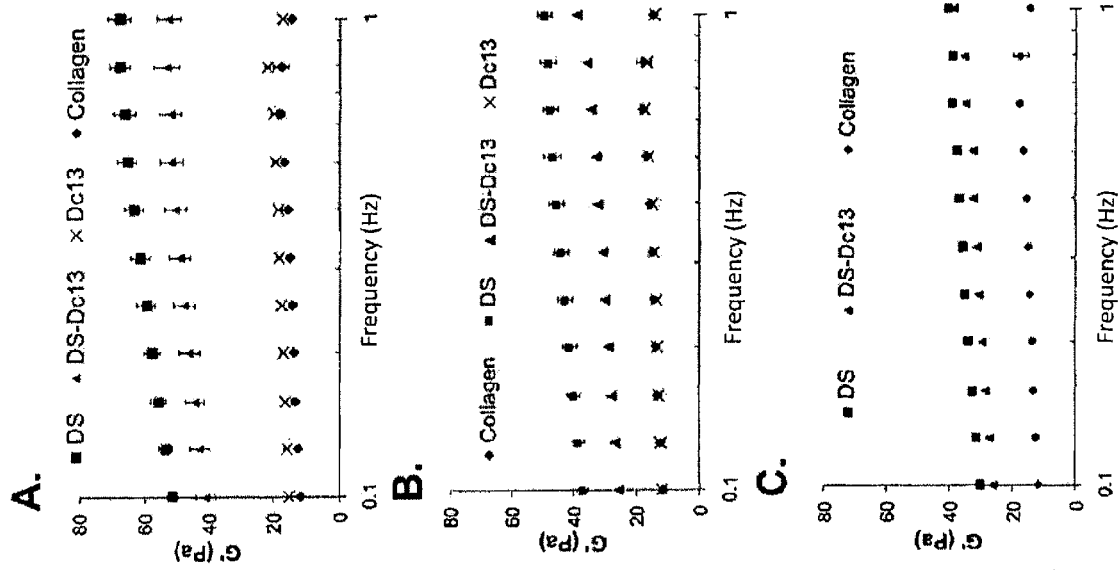
FIG. 35. Storage Modulus (G') of Collagen Gels. Rheological mechanical testing of collagen gels formed with each additive at A. 5:1 B. 10:1 and C. 30:1 molar ratio of collagen: additive. Frequency sweeps from 0.1 Hz to 1.0 Hz with a controlled stress of 1.0 Pa were performed. G'avg±S.E. are presented.

Collagen gels were prepared, as in EXAMPLE 16. Viscoelastic characterization was performed as described in EXAMPLE 17 on gels formed with varying ratios of collagen to additive (treatment). Treatment with dermatan sulfate or dermatan-Dc13 conjugate increase the stiffness of the resulting collagen gel over untreated collagen as shown in FIG. 35.

Example 35

Cell Proliferation and Cytotoxicity Assay

Figure 36:
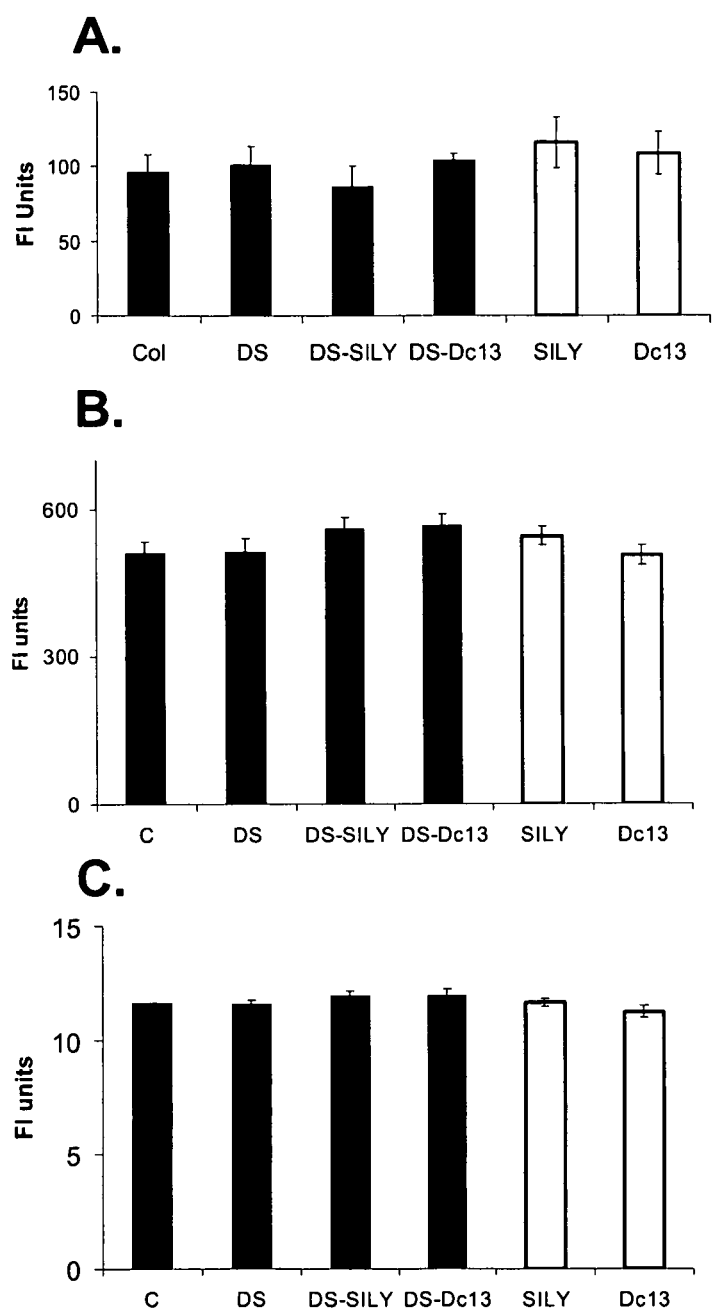
FIG. 36. Cell Proliferation and Cytotoxicity Assays. No significant differences were found between all additives in A. CyQuant B. Live and C. Dead assays.

HCA SMCs, prepared as in EXAMPLE 30, were seeded at $4.8 \times 10^4$ cells/mL in growth medium onto a 96-well tissue-culture black/clear bottom plate (Costar) and allowed to adhere for 4 hrs. Growth medium was aspirated and 600 µL of differentiation medium containing each additive at a concentration equivalent to the concentration within collagen gels ($1.4 \times 10^{-6}$ M) was added to each well. Cells were incubated for 48 hrs and were then tested for cytotoxicity and proliferation using Live-Dead and CyQuant (Invitrogen) assays, respectively, according to the manufacturer's protocol. Cells in differentiation medium containing no additive were used as control. The results are shown in FIG. 36 indicating that none of the treatments demonstrated significant cytotoxic effects.

Example 36

Inhibition of Platelet Binding and Platelet Activation to Collagen Type I

Microplate Preparation

Type I fibrillar collagen (Chronolog, Havertown, Pa.) was diluted in isotonic glucose to a concentration of 20-100 µg/mL. 50 µL of collagen solution was added to each well of a high bind 96-well plate. The plate was incubated overnight at 4 C, and then rinsed 3× with 1×PBS.

Peptidoglycan was diluted in 1×PBS at concentrations of 25 µM to 50 µM and 50 µL solution was added to the collagen coated wells. Controls of GAG, peptide, or PBS were also added to collagen coated wells as controls. Treatments were incubated at 37° C. with shaking at 200 rpm for 30 mM Wells were then rinsed 3× with 1×PBS, including a 20 mM rinse with 200 rpm shaking to remove unbound treatment molecule.

Platelet Preparation and Activation

Human whole blood was collected from healthy volunteers by venipuncture following the approved Purdue IRB protocol and with informed consent. The first 5 mL of blood was discarded as it can be contaminated with collagen and other proteins, and approximately 15 mL was then collected into citrated glass vacutainers (BD Bioscience). Blood was centrifuged in the glass tube for 20 min at 200×g at 20° C. The top layer of the centrifuged blood, the platelet rich plasma (PRP), was used for platelet experiments. PRP (50 µL/well) was added to the microplate and allowed to incubate for 1 hr at room temperature without shaking.

After 1 hour of incubation, the PRP was removed from each well and added to a microcentrifuge tube containing 5 µL ETP (107 mM EDTA, 12 mM theophylline, and 2.8 µM prostaglandin E1) to inhibit further platelet activation. These tubes were spun at 4° C. for 30 mM at 1900×g to pellet the platelets. The supernatant (platelet serum) was collected for ELISA studies to test for the presence of platelet activation markers PF-4 and Nap-2.

Platelet Adherence

After the PRP was removed from the wells of the collagen/treatment coated plates, the wells were rinsed 3× with 0.9% NaCl for 5 min each shaking at 200 rpm. Platelet adherence was quantified colormetrically or visualized fluorescently.

Colormetric Assay

Figure 41:
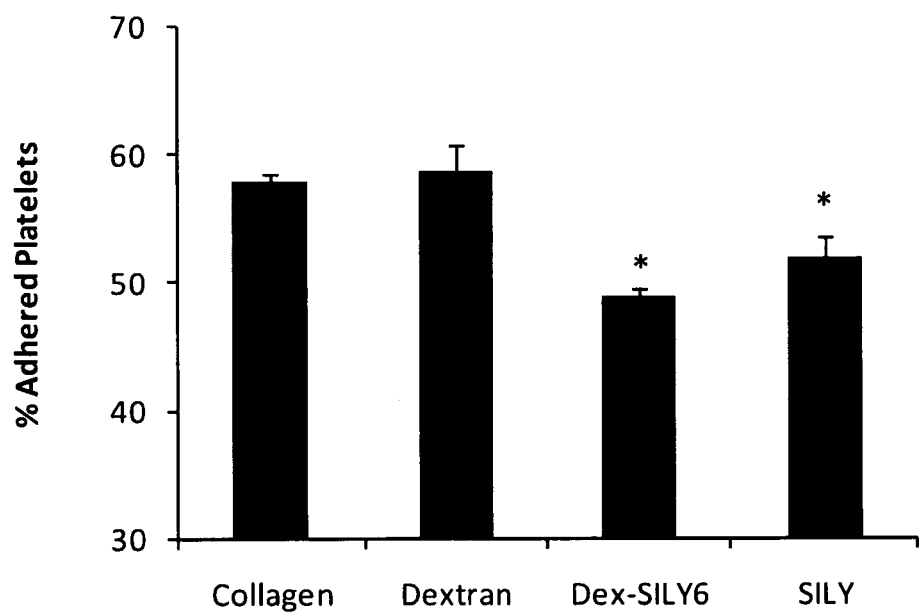
FIG. 41 Inhibition of Platelet Binding to Collagen by Colorimetric Assay. Collagen immobilized on the surface of a 96-well plate was pre-incubated with each treatment and subsequently incubated with platelet rich plasma (PRP). Microplate assay prepared as described was pre-incubated with treatments Collagen, PBS only; Dextran; Dex-SILY6, dextran-(SILY)$_6$; SILY, SILY peptide. *Significant vs. collagen (no treatment).
Figure 42:
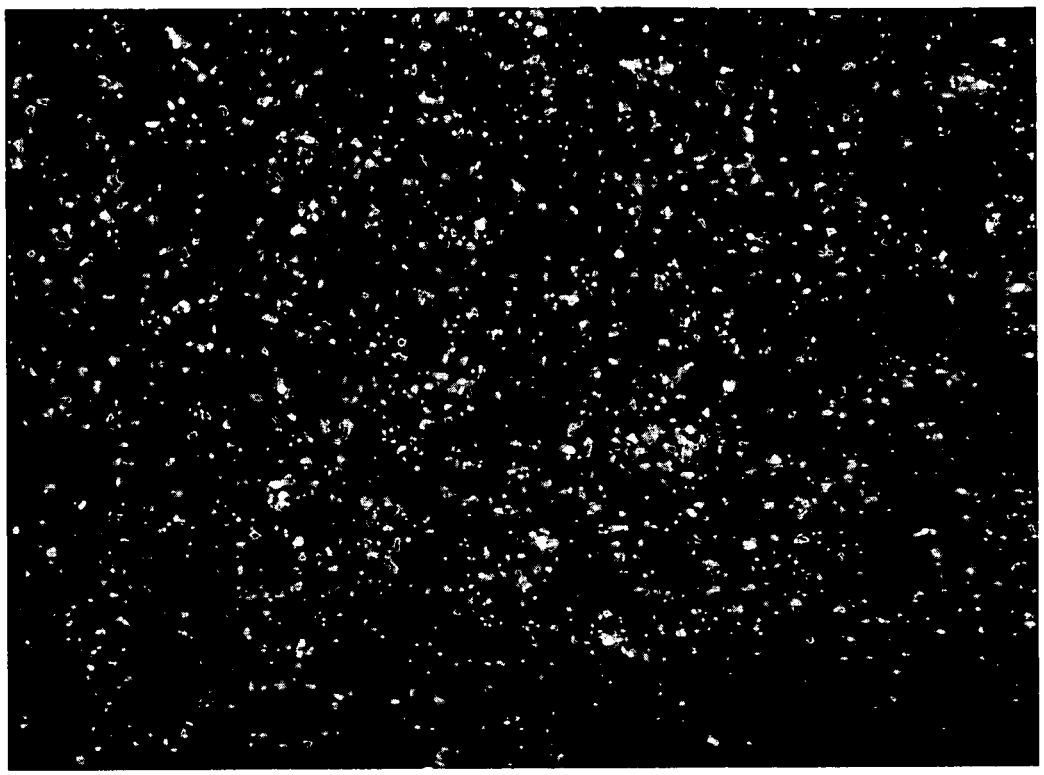
FIG. 42. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescent microscope using a DAPI filter. No treatment, i.e. collagen treated with PBS.
Figure 43:
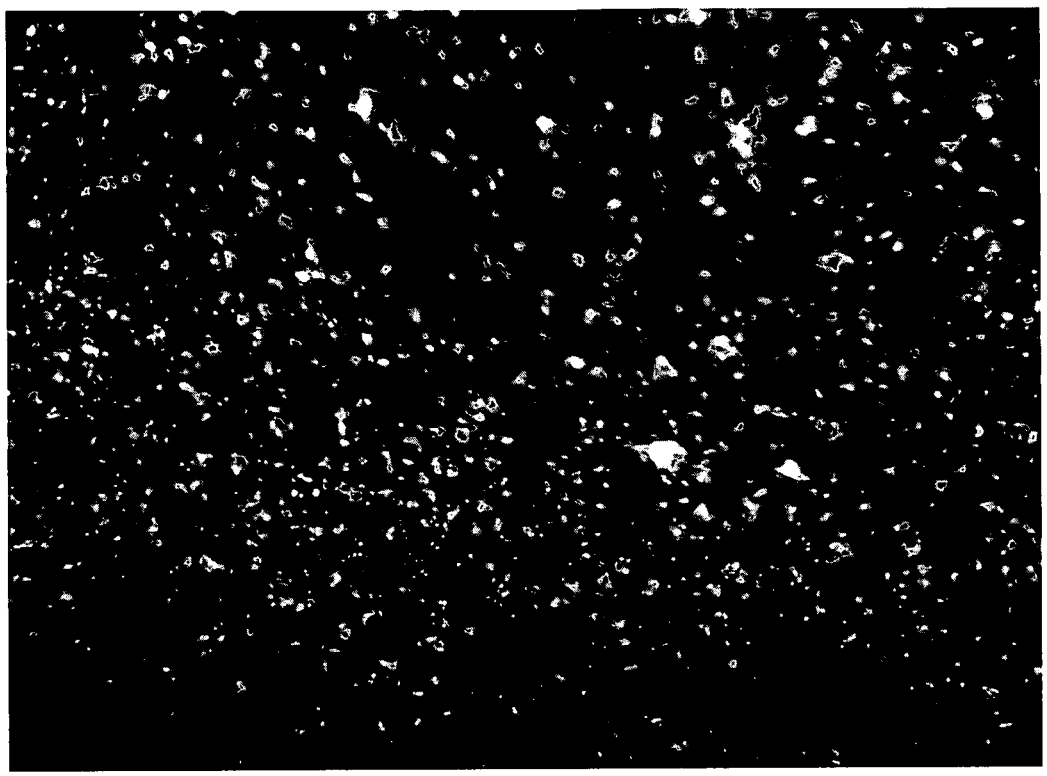
FIG. 43. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: dextran.
Figure 44:
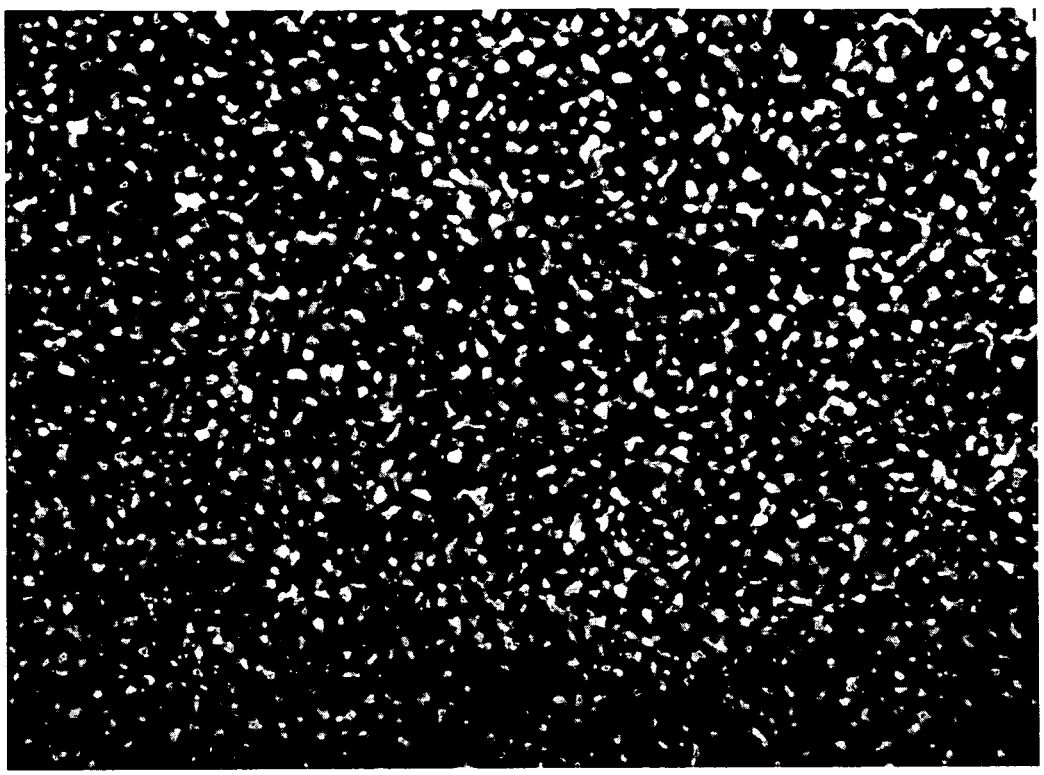
FIG. 44. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: dextran-SILY9 conjugate.
Figure 45:
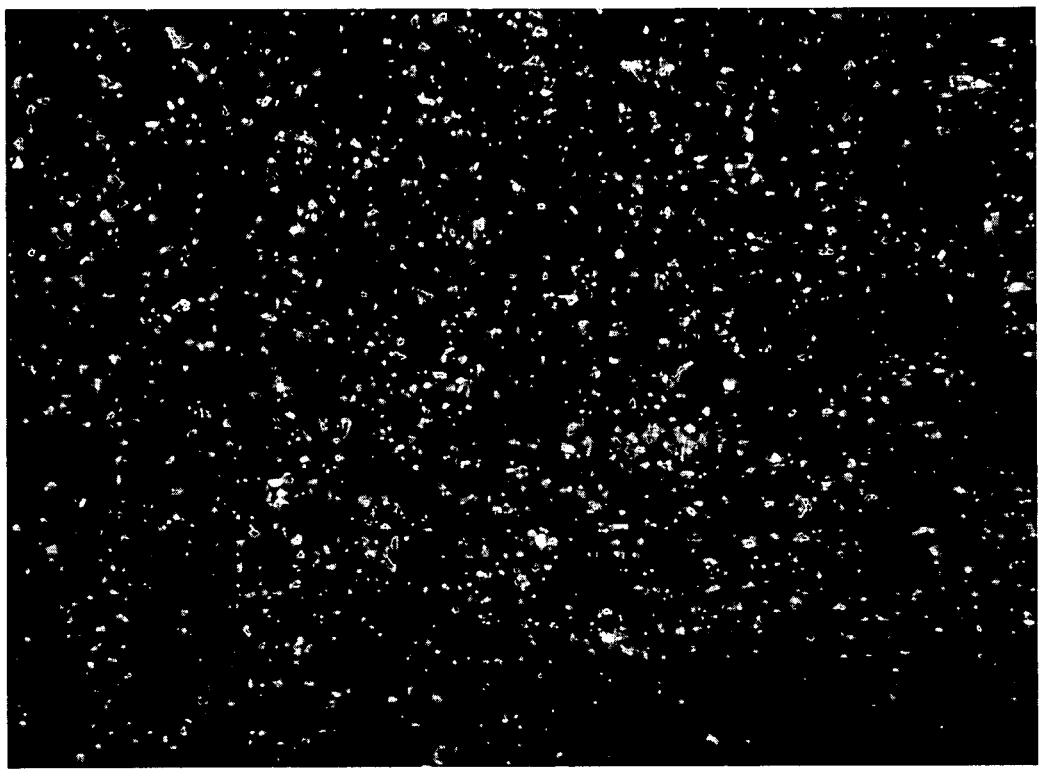
FIG. 45. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. No treatment, i.e. collagen treated with PBS.
Figure 46:
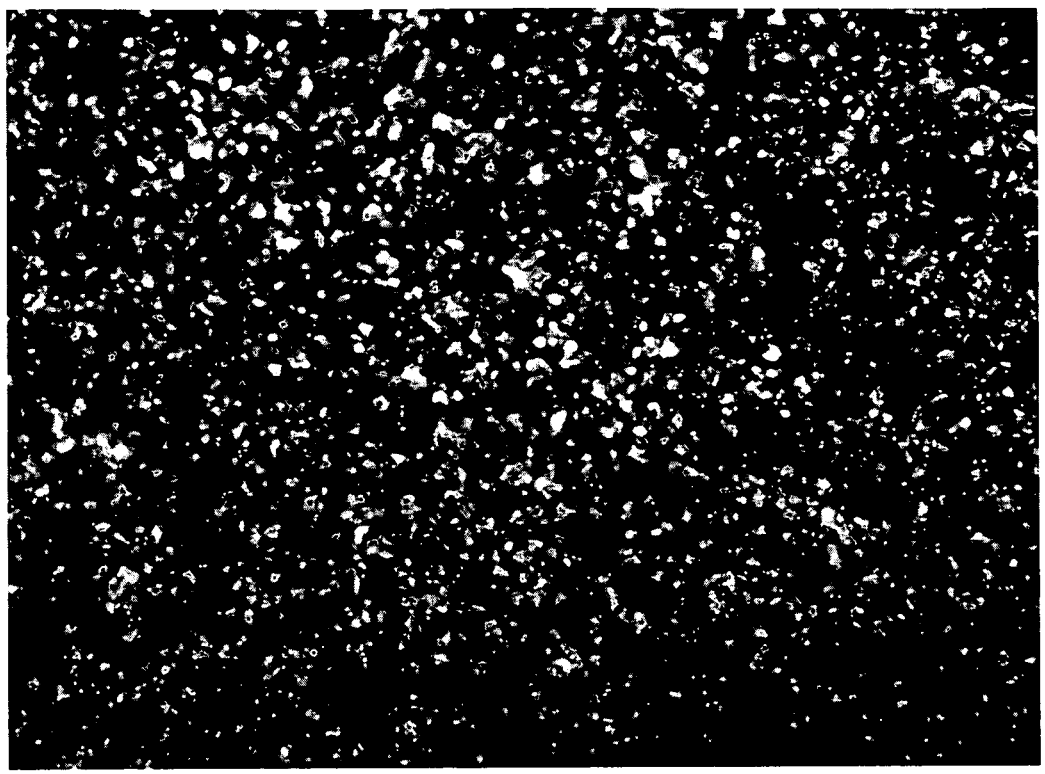
FIG. 46. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: hyaluronan.
Figure 47:
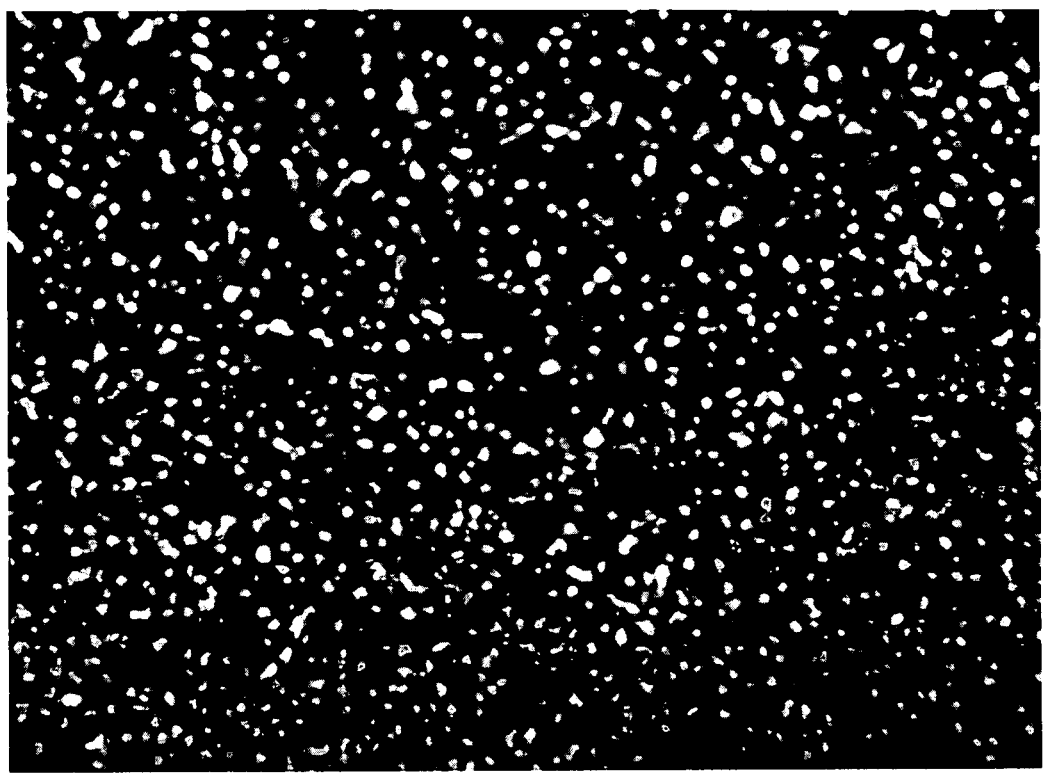
FIG. 47. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: hyaluronan-SILY conjugate.
Figure 48:
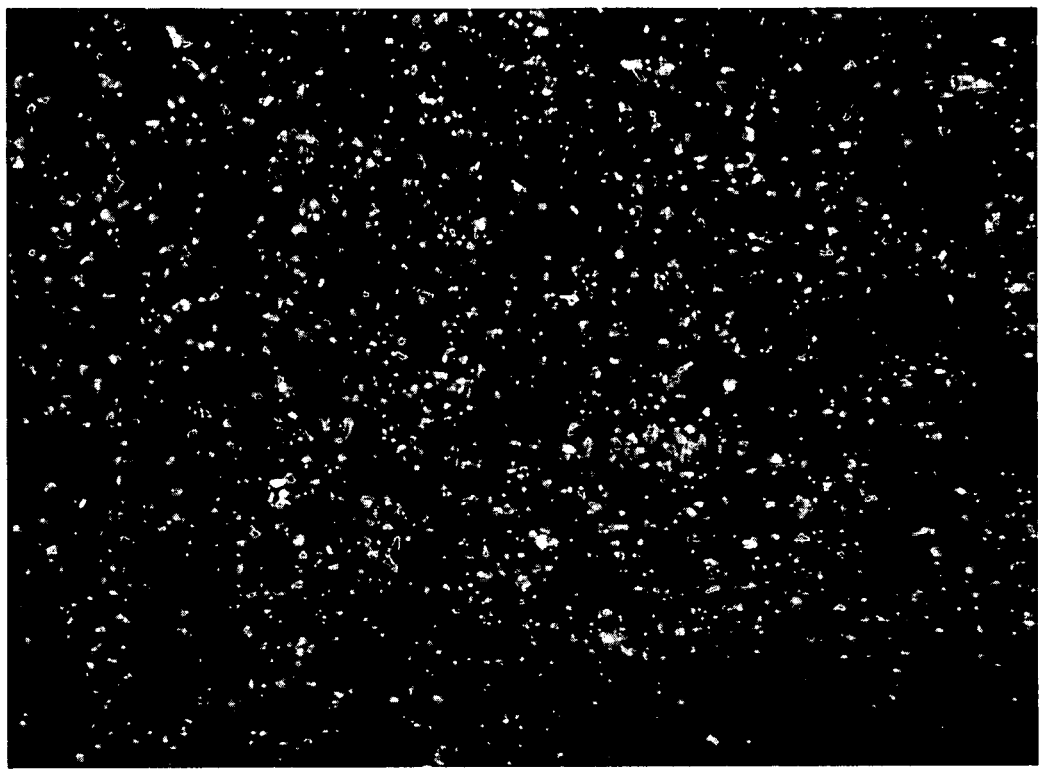
FIG. 48. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. No treatment, i.e. collagen treated with PBS.
Figure 49:
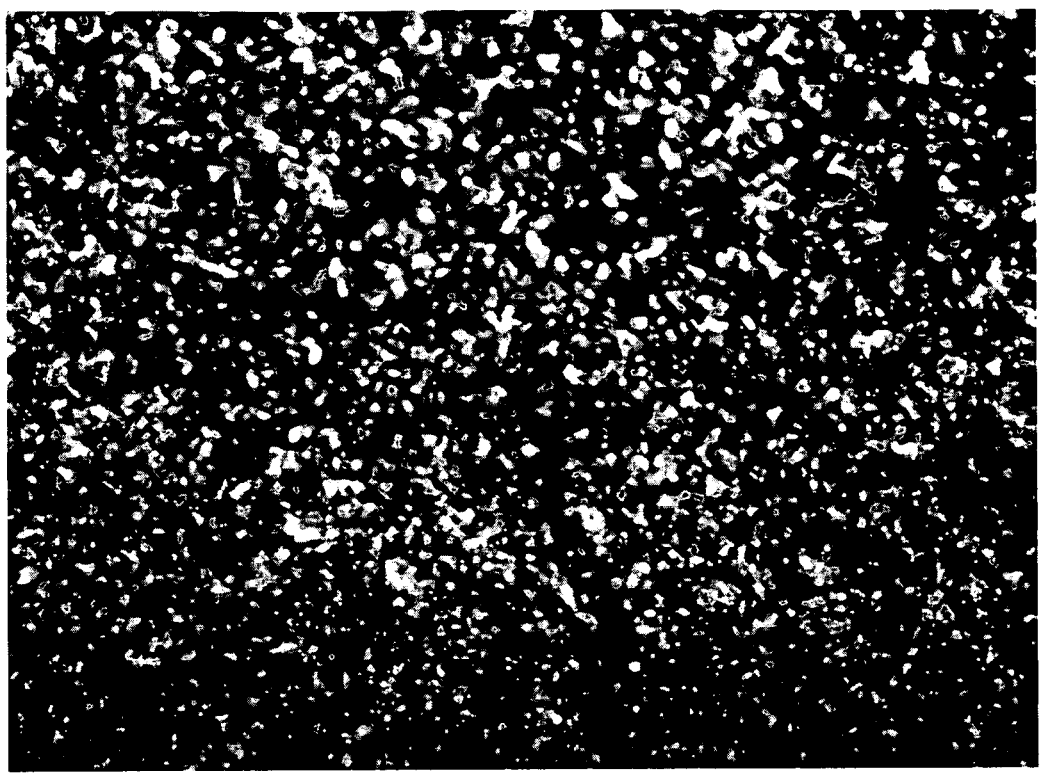
FIG. 49. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: heparin.
Figure 50:
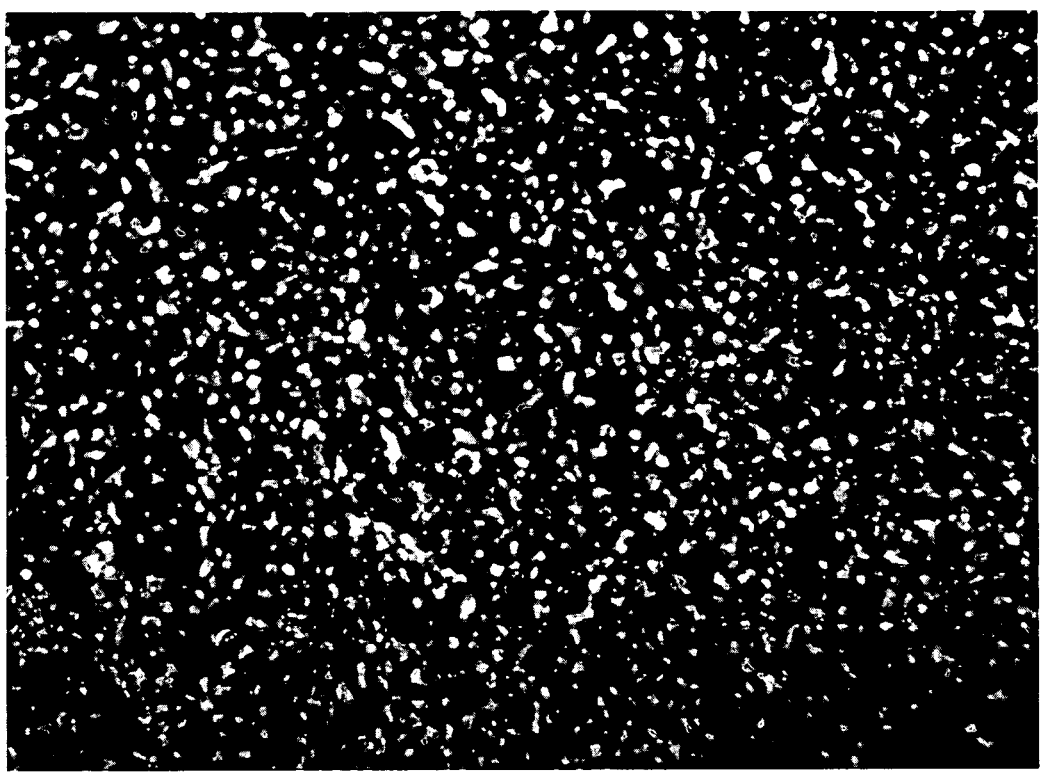
FIG. 50. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: heparin-SILY conjugate.
Figure 51:
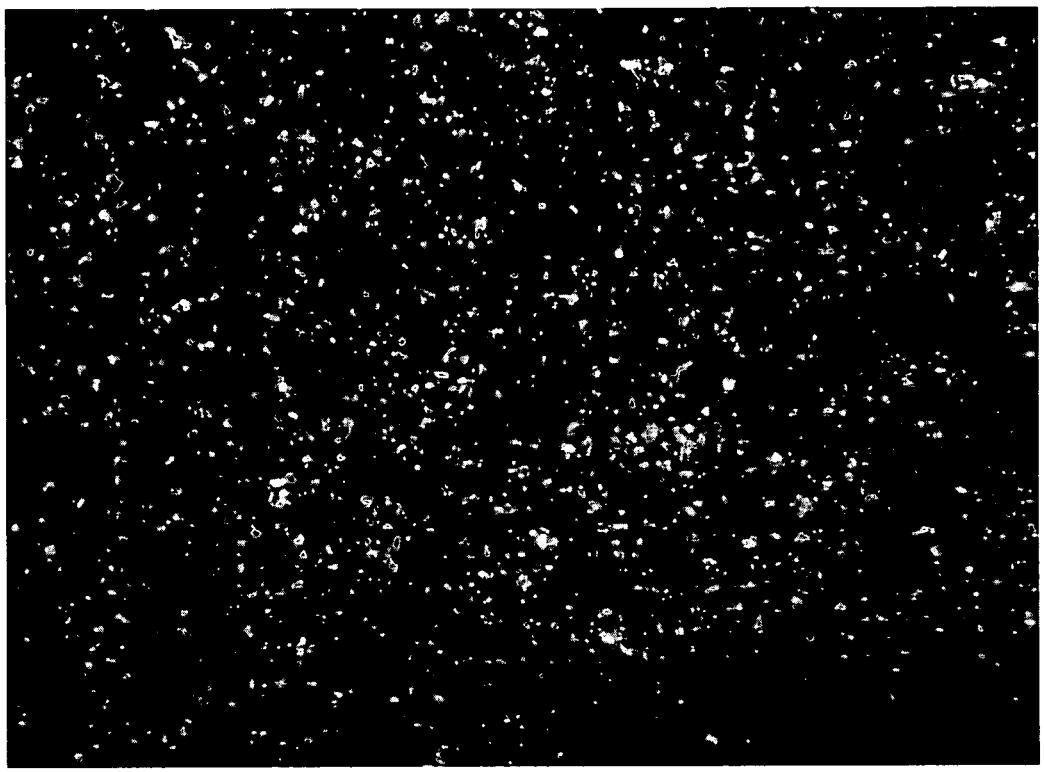
FIG. 51. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. No treatment, i.e. collagen treated with PBS.
Figure 52:
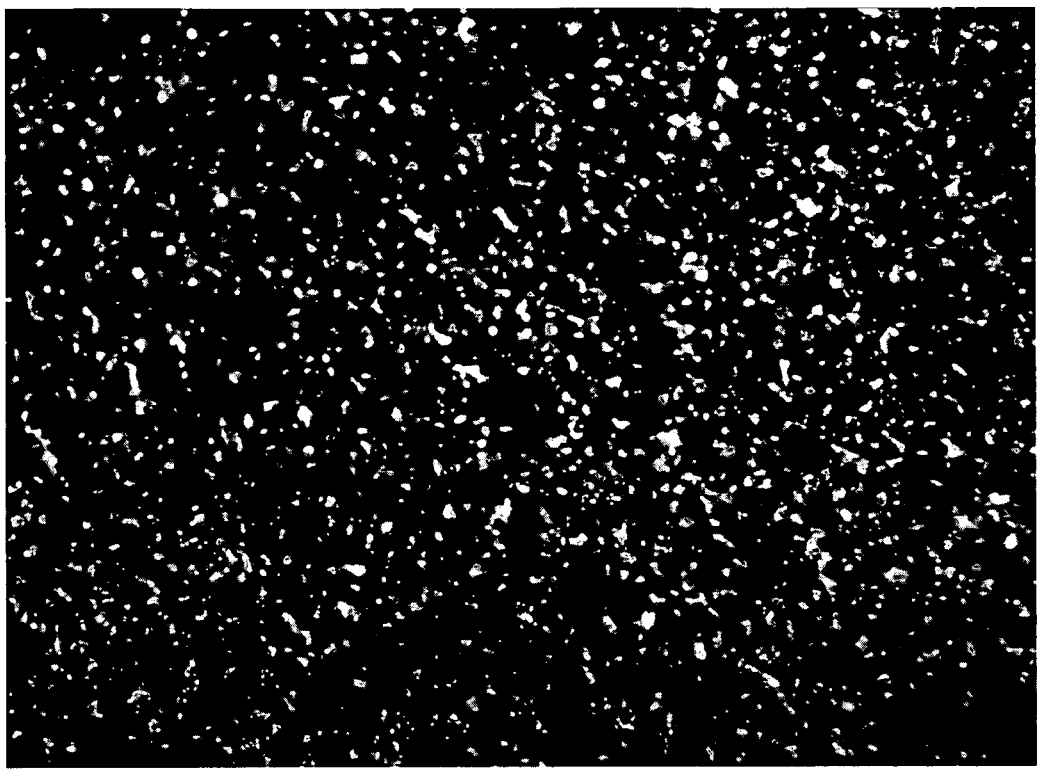
FIG. 52. Fluorescence image of adhered platelets. Adhered platelets were fixed with 4% paraformaldehyde, permeabilized with 0.1% Triton X-100, and platelet actin was labeled with phalloidin-AlexaFluor 488. The adhered platelets were imaged using an upright fluorescence microscope using a DAPI filter. Treatment: SILY peptide.

140 µL of a sodium citrate/citric acid buffer (0.1M, pH 5.4) containing 0.1% Triton X-100 and 1 mg/mL p-nitrophenyl phosphate was added to each well. The background absorbance was measured at 405 nm. The plate was then incubated for 40 min at room temperature with shaking at 200 rpm. The Triton X-100 creates pores in the cells, allowing p-nitrophenyl phosphate to interact with acid phosphatase in the platelets to produce p-nitrophenol. After 40 min of incubation, 100 µL of 2M NaOH was added to each well. The pH change stops the reaction by inactivating acid phosphatase, and also transforms the p-nitrophenol to an optically active compound. The absorbance was then read at 405 nm and correlated to the number of adhered platelets. The results are shown in FIG. 41.

Fluorescent Assay

Adhered platelets were fixed by incubation with 4% paraformaldehyde for 10 min at room temperature. The platelets were permeabilized with 0.1% Triton X-100 for 5 min. Platelet actin was labeled by incubation with phalloidin-AlexaFluor 488 (Invitrogen) containing 1% BSA for 30 min. The wells were rinsed 3× with 1×PBS, and the adhered platelets were imaged using an upright fluorescent microscope using a DAPI filter.

Figure 39:
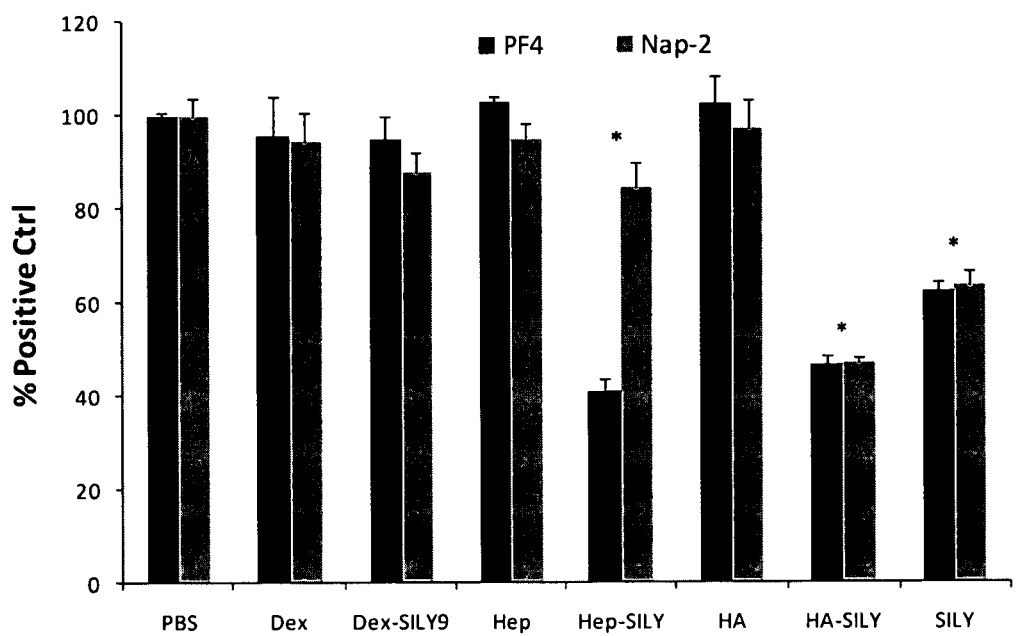
FIG. 39. Inhibition of Platelet Activation. Measured by determining the release of activation factors Platelet Factor 4 (PF-4) and β-thromboglobulin (Nap-2). Collagen immobilized on the surface of a 96-well plate was pre-incubated with each treatment and subsequently incubated with platelet rich plasma (PRP). Values are reported as a percentage of activation factor released by the treatment compared to the amount of activation factor released by the control treatment (phosphate buffered saline, PBS). The * indicates that the difference is significant vs. collagen surface with no treatment (phosphate buffered saline, PBS). Dex, dextran; Dex-SILY9, dextran-(SILY)$_9$ conjugate; Hep, heparin; Hep-SILY, heparin-SILY conjugate; HA, hyaluronan; HA-SILY, hyaluronan-SILY conjugate; SILY, SILY peptide. Due to solubility limits, Hep, Hep-SILY, HA, and HA-SILY were incubated at 25 µM. All other treatments were at 50 µM (after the treatment was removed, the plates were washed with PBS<1 min, before addition of PRP). Hep and HA (hyaluronic acid) conjugates contained approximately 4 peptides per polysaccharide.
Figure 40:
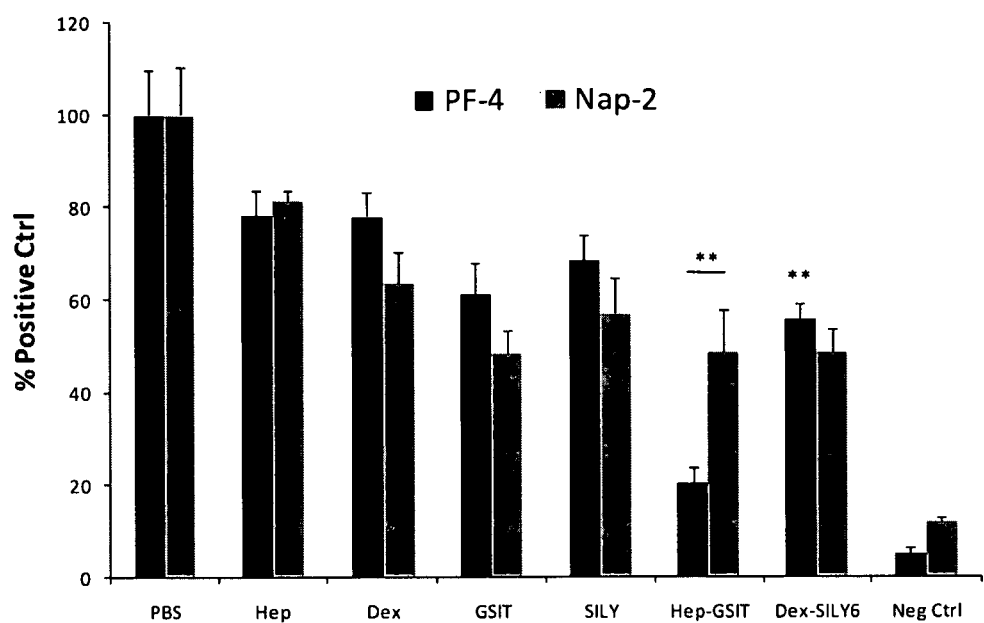
FIG. 40. Inhibition of Platelet Activation. Measured by determining the release of activation factors Platelet Factor 4 (PF-4) and β-thromboglobulin (Nap-2). Collagen immobilized on the surface of a 96-well plate was pre-incubated with each treatment and subsequently incubated with platelet rich plasma (PRP). Values are reported as a percentage of activation factor released by the treatment compared to the amount of activation factor released by the control treatment (phosphate buffered saline, PBS). Dex, dextran; Dex-SILY6, dextran-(SILY)$_6$ conjugate; Hep, heparin; Hep-GSIT, heparin-GSIT conjugate; GSIT, GSIT peptide; SILY, SILY peptide. The values measured for all treatments are significant vs. PBS. Dex, SILY, and Dex-SILY6 are at 25 µM, all other treatments are at 50 µM. The **indicates that the value for the Hep-GSIT treatment was significant vs. the values for the Hep treatment, similarly the value for the Dex-SILY6 treatment was significant vs. the value for the Dex treatment for PF4. (After the treatment was removed the plates were rinsed for 20 min) Hep conjugates contained approximately 4 peptides per polysaccharide.

See FIGS. 42 to 52 for results. Platelet aggregation on untreated collagen surfaces is indicated by blurred images resulting from clumped platelets. Without being bound by theory, it is believed that clumping of platelets in the z-direction (perpendicular to the plate surface) prevents image capture in one focal plane. On treated surfaces, reduced platelet aggregation results in less clumping (fewer platelets in the z-direction), and focused images can be captured at the plate surface. These images show that treatment with the synthetic peptidoglycans reduces adhesion of platelet cells to collagen, Detection of Platelet Activation Markers The supernatant (platelet serum) obtained after pelleting the platelets was used to determine released activation factors. Platelet factor 4 (PF-4) and β-thromboglobulin (Nap-2) are two proteins contained within alpha granules of platelets which are released upon platelet activation. Sandwich ELISAs were utilized in order to detect each protein. The components for both sandwich ELISAs were purchased from (R&D Systems) and the provided protocols were followed. The platelet serum samples were diluted 1:10,000-1:40,000 in 1% BSA in 1×PBS so the values fell within a linear range. The results shown in FIGS. 39 and 40 show that treatment with synthetic peptidoglycans decreases platelet activation by collagen I.

Example 37

Inhibition of Platelet Binding and Platelet Activation to Collagen Type III and Type I The method according to EXAMPLE 36 was used with the following modification.

Microplate Preparation

Type I collagen (rat tail collagen, BD Biosciences) and type III collagen (Millipore) were combined on ice with NaOH, 1×PBS, and 10×PBS to physiological conditions. The total collagen concentration was 1 mg/mL with 70% type I collagen and 30% type III collagen. 30 µL of the collagen solution was pipetted into each well of a 96-well plate. The plate was incubated at 37° C. in a humidified incubator for one hour, allowing a gel composed of fibrillar collagen to form in the wells. The wells were rinsed 3× with 1×PBS.

Peptidoglycan was diluted in 1×PBS at concentrations of 25 µM and 50 µL solution was added to the collagen coated wells. Controls of GAG, peptide, or PBS were also added to collagen coated wells as controls. Combinations of peptidoglycan or peptide were composed of 25 µM of each molecule in 1×PBS. Treatments were incubated at 37° C. with shaking at 200 rpm for 30 min Wells were then rinsed 3× with 1×PBS, including a 10 min rinse with 200 rpm shaking to remove unbound treatment molecule.

Figure 54:
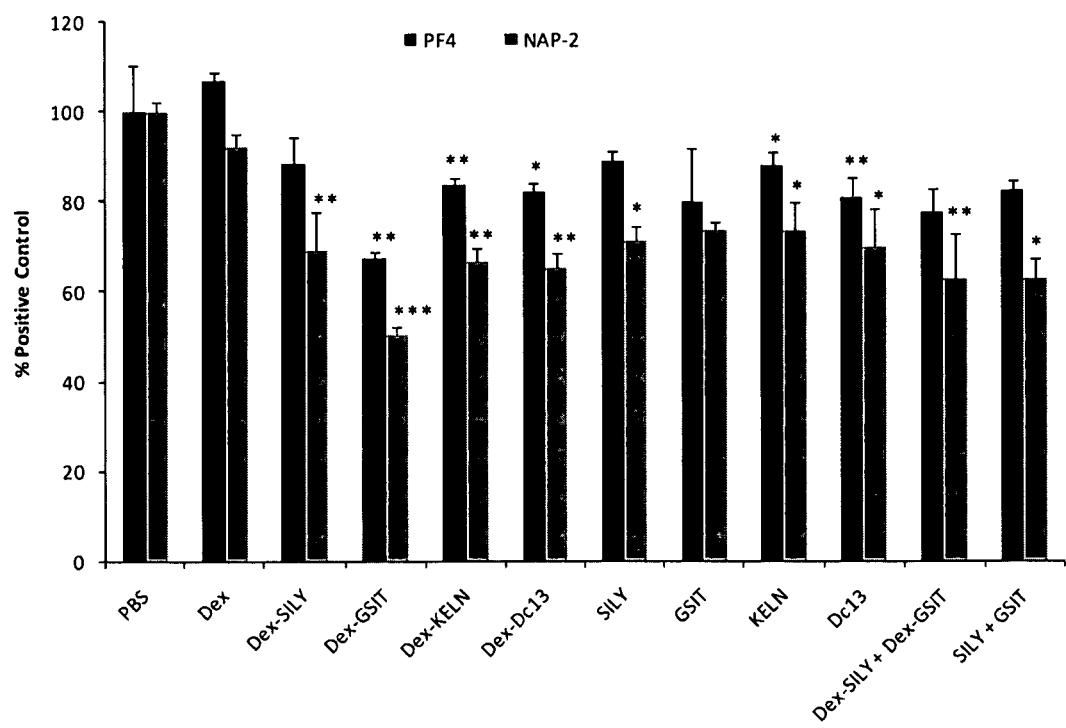
FIG. 54. Inhibition of Platelet Activation. Measured by determining the release of activation factors Platelet Factor 4 (PF-4) and β-thromboglobulin (Nap-2). Type I and III collagen gels on the surface of a 96-well plate were pre-incubated with each treatment and subsequently incubated with PRP. Platelet activation was measured by the release of activation factors PF-4 and Nap-2. Treatments: PBS, buffer alone; Dex, dextran; Dex-SILY, dextran-SILY conjugate; Dex-GSIT, dextran-GSIT conjugate; Dex-KELN, dextran-KELN conjugate; Dex-Dc13, dextran-Dc13 conjugate; SILY, SILY peptide; GSIT, GSIT peptide; KELN, KELN peptide; Dc13, Dc13 peptide; Dex-SILY+Dex-GSIT; combination of dextran-SILY conjugate and dextran-GSIT conjugate; SILY+GSIT; combination of SILY peptide and GSIT peptide. *Indicates the results are significant vs. collagen surface with no treatment (PBS). Indicates the results are also significant vs. collagen surface with Dex. *Indicates the results are also significant vs. collagen surface with corresponding peptide control. All peptidoglycans caused significant decrease in NAP-2 release compared to no treatment (PBS) or dextran treatment, while Dex-GSIT additionally decreased release over its peptide control (GSIT). Dex-GSIT and Dex-KELN significantly decreased PF-4 release relative to no treatment (PBS) and dextran treatment, while Dex-Dc13 significantly decreased PF-4 release over no treatment (PBS).

The results of the platelet activation inhibition measurements shown in FIG. 54 demonstrate that the synthetic peptidoglycans inhibit platelet cell activation by a mixture of collagen Type I and Type III.

Figure 55:
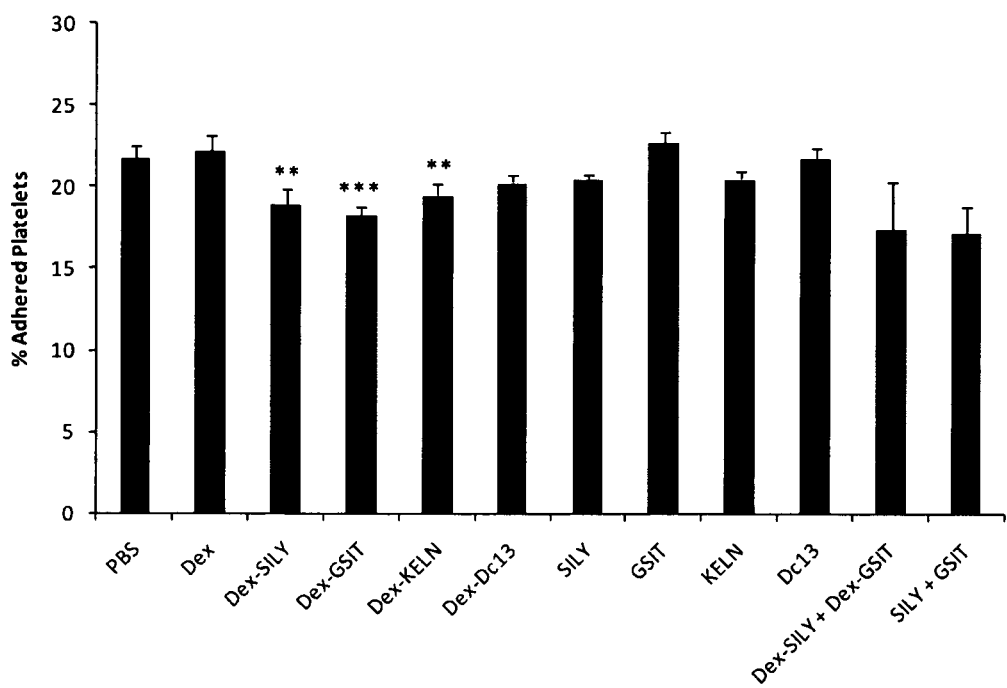
FIG. 55 Inhibition of Platelet Binding to Collagen (Adhesion) by Colorimetric Assay. Treatments: PBS, buffer alone; Dex, dextran; Dex-SILY, dextran-SILY conjugate; Dex-GSIT, dextran-GSIT conjugate; Dex-KELN, dextran-KELN conjugate; Dex-Dc13, dextran-Dc13 conjugate; SILY, SILY peptide; GSIT, GSIT peptide; KELN, KELN peptide; Dc13, Dc13 peptide; Dex-SILY+Dex-GSIT; combination of dextran-SILY conjugate and dextran-GSIT conjugate; SILY+GSIT; combination of SILY peptide and GSIT peptide. *Significant vs. Collagen surface with no treatment (PBS). Also significant vs. collagen surface with Dex. *Also significant vs. collagen surface with corresponding peptide control. Dex-SILY and Dex-KELN had significantly decreased platelet adherence as compared to no treatment (PBS) or Dextran treatment, while Dex-GSIT additionally decreased platelet adherence over its peptide control treatment (GSIT).

The results shown in FIG. 55 demonstrate that the peptidoglycans inhibit platelet cell binding to collagen Type I and Type III mixtures.

What is claimed is:

1. A compound of formula $(P_nL)_XG$ wherein n is 1 to 5;
X is 1 to 10;
P is a synthetic peptide of up to about 40 amino acids comprising the amino acid sequence RRANAALKAGELYKSILYGC (SEQ ID NO: 1) wherein the amino acid sequence comprises a collagen-binding domain;
L is a linker which links "P" and "G" in said formula; and
G is a glycan, wherein P is linked to G via the linker.

2. The compound of claim 1 wherein the glycan is a glycosaminoglycan or a polysaccharide.

3. The compound of claim 1 wherein the glycan is selected from the group consisting of alginate, agarose, dextran, chondroitin, dermatan, dermatan sulfate, heparan, heparin, keratin, and hyaluronan.

4. The compound of claim 1 wherein the glycan is selected from the group consisting of dermatan sulfate, dextran, and heparin.

5. The compound of claim 1 wherein the linker is —SCH$_2$CH$_2$C(O)NHN=.

6. A composition comprising the compound of claim 1 and one or more pharmaceutically acceptable excipient, or diluent, or a combination thereof.

7. The composition of claim 6 in a form adapted for topical use.

8. The composition of claim 7 wherein the topical form is selected from the group consisting of a powder, a gel, a cream, an ointment, a plaster, and a topical liquid.

9. The composition of the claim 6 adapted for parenteral administration.

10. The composition of claim 9 wherein the parenteral administration is intravenous or intra-arterial.

11. The composition of claim 6 wherein the glycan is a glycosaminoglycan or a polysaccharide.

12. The composition of claim 6 wherein the glycan is selected from the group consisting of alginate, agarose, dextran, chondroitin, dermatan, dermatan sulfate, heparan, heparin, keratin, and hyaluronan.

13. The composition of claim 6 wherein the compound is formulated in a dose from 1 µg/kg to 10 mg/kg patient body weight for administration to a patient.

14. The composition of claim 6 wherein the compound is formulated in a dose from 100 µg/kg to about 1 mg/kg patient body weight for administration to a patient.

15. The composition of claim 6 wherein the compound is formulated in a dose from 1 µg/kg to about 500 µg/kg patient body weight for administration to a patient.

16. The composition of claim 6 wherein the compound is formulated in a dose from 100 µg/kg to about 400 µg/kg patient body weight for administration to a patient.

* * * * *

UNITED STATES PATENT AND TRADEMARK OFFICE
CERTIFICATE OF CORRECTION

| | | |
|---|---|---|
| PATENT NO. | : 8,846,003 B2 | Page 1 of 1 |
| APPLICATION NO. | : 12/934551 | |
| DATED | : September 30, 2014 | |
| INVENTOR(S) | : Alyssa Panitch et al. | |

It is certified that error appears in the above-identified patent and that said Letters Patent is hereby corrected as shown below:

In the Specification

Column 1, Lines 17-23, please replace:
"Part of the work during the development of this invention was made with government support from the National Institutes of Health under grant application number K25HL074968. The U.S. Government has certain rights in the invention."
With:
-- The United States Government has certain rights in the disclosure under HL074968 awarded by the National Institutes of Health. --

Signed and Sealed this
Twenty-second Day of September, 2020

Andrei Iancu
*Director of the United States Patent and Trademark Office*